(12) United States Patent
Meiron

(10) Patent No.: US 9,393,273 B2
(45) Date of Patent: Jul. 19, 2016

(54) METHODS OF TREATING INFLAMMATORY COLON DISEASES

(75) Inventor: Moran Meiron, Zikhron-Yaakov (IL)

(73) Assignee: Pluristem Ltd., Haifa (IL)

( * ) Notice: Subject to any disclaimer, the term of this patent is extended or adjusted under 35 U.S.C. 154(b) by 262 days.

(21) Appl. No.: 12/994,603

(22) PCT Filed: May 26, 2009

(86) PCT No.: PCT/IL2009/000527
§ 371 (c)(1),
(2), (4) Date: Feb. 1, 2011

(87) PCT Pub. No.: WO2009/144720
PCT Pub. Date: Dec. 3, 2009

(65) Prior Publication Data
US 2011/0129486 A1    Jun. 2, 2011

Related U.S. Application Data

(60) Provisional application No. 61/071,944, filed on May 27, 2008.

(51) Int. Cl.
*A61K 35/00*     (2006.01)
*A61K 35/50*     (2015.01)
*C12N 5/073*     (2010.01)
*A61K 35/12*     (2015.01)

(52) U.S. Cl.
CPC .............. *A61K 35/50* (2013.01); *C12N 5/0605* (2013.01); *A61K 2035/122* (2013.01)

(58) Field of Classification Search
USPC ........................................................ 424/93.7
See application file for complete search history.

(56) References Cited

U.S. PATENT DOCUMENTS

| | | |
|---|---|---|
| 6,911,201 B1 | 6/2005 | Merchav et al. |
| 7,534,609 B2 | 5/2009 | Merchav et al. |
| 7,678,573 B2 | 3/2010 | Merchav et al. |
| 8,524,496 B2 | 9/2013 | Meiron et al. |
| 8,529,888 B2 | 9/2013 | Meiron et al. |
| 9,096,827 B2 | 8/2015 | Meiron et al. |
| 2003/0091542 A1 | 5/2003 | Eberhardt et al. |
| 2005/0176143 A1 | 8/2005 | Merchav et al. |
| 2005/0181504 A1 | 8/2005 | Merchav et al. |
| 2005/0244421 A1* | 11/2005 | Strittmatter et al. ........ 424/185.1 |
| 2006/0045872 A1* | 3/2006 | Miguel et al. ................ 424/93.7 |
| 2006/0182724 A1 | 8/2006 | Riordan |
| 2009/0004738 A1 | 1/2009 | Merchav et al. |
| 2010/0209403 A1 | 8/2010 | Meiron et al. |
| 2011/0129447 A1 | 6/2011 | Meretski et al. |
| 2011/0171182 A1 | 7/2011 | Meiron et al. |
| 2011/0256108 A1 | 10/2011 | Meiron et al. |
| 2011/0256159 A1 | 10/2011 | Meiron et al. |
| 2011/0256160 A1 | 10/2011 | Meiron et al. |
| 2011/0293583 A1 | 12/2011 | Aberman |
| 2012/0122220 A1 | 5/2012 | Perski et al. |
| 2013/0004465 A1 | 1/2013 | Aberman |
| 2013/0039892 A1 | 2/2013 | Aberman |
| 2013/0259843 A1 | 10/2013 | Duda et al. |
| 2013/0323213 A1 | 12/2013 | Meiron et al. |
| 2013/0337558 A1 | 12/2013 | Meiron et al. |
| 2014/0017209 A1 | 1/2014 | Aberman et al. |
| 2014/0030805 A1 | 1/2014 | Kasuto et al. |
| 2014/0242039 A1 | 8/2014 | Meiron et al. |
| 2015/0125138 A1 | 5/2015 | Duda et al. |
| 2015/0216907 A1 | 8/2015 | Chajut et al. |
| 2015/0232797 A1 | 8/2015 | Kasuto et al. |

FOREIGN PATENT DOCUMENTS

| | | | |
|---|---|---|---|
| EA | 009073 B1 | 10/2007 | |
| RU | 2252252 C1 | 5/2005 | |
| RU | 2301667 C1 | 6/2007 | |
| RU | 2322984 C2 | 4/2008 | |
| WO | WO03/030823 | 4/2003 | |
| WO | WO 2007047468 A2 * | 4/2007 | ............. A61K 35/50 |
| WO | WO 2007108003 A2 * | 9/2007 | |
| WO | WO2008/150368 | 12/2008 | |
| WO | WO2009/037690 | 3/2009 | |

OTHER PUBLICATIONS

Banas et al. "Adipose tissue-derived mesenchymal stem cells as a source of human hepatocytes" Hepatology 46: 219-228, 2007.*
Banas et al. "Adipose tissue-derived mesenchymal stem cells as a source of human hepatocytes" Hepatology 46: 219-228, 2007).*
Kern et al. "Comparative analysis of mesenchymal stem cells from bone marrow, umbilical cord blood, or adipose tissue", Stem Cells 24: 1294-1301, 2006.*
Garcia-Olma et al. A phase I clinical trial of the treatment of Crohn's fistula by adipose mesenchymal stem cell transplant, Diseases of the Colon and Rectum 48(7): 1416-23, 2005.*
Snook "Are the inflammatory bowel diseases autoimmune disorders?", Gut 31: 961-3, 1990.*
Kang et al. "Neurogenesis of Rhesus adipose stromal cells", J. of Cell Science 117: 4289-99, 2004.*
Van Montfrans et al. "Immunotherapy of Crohn's disease", Mediators of Inflammation 7: 149-52, 1998.*
American Autoimmune Related Diseases Association "List of autoimmune and autoimmune-related diseases" Association webpage, available online 2012.*
Kmiecik et al. "Current view on osteogenic differentiation potential of mesenchymal stromal cells derived from placental tissues", Stem Cell Reviews and Reports 11: 570-585, 2015.*
European Patent Office, European Search Report, European Patent Application No. 13168957, Aug. 8, 2013, 5 pages.
Brooke et al., "Therapeutic Applications of Mesenchymal Stromal Cells," *Seminars in Cell & Developmental Biology* (Sep. 18, 2007 18:846-58.
Tyndall et al., "Multipotent Mesenchymal Stromal Cells for Autoimmune Diseases: Teaching New Dogs Old Tricks," *Bone Marrow Transplantation* (Mar. 23, 2009), 43:821-28.
Pluristem Therapeutics, Inc., Press Release, "Pluristem Demonstrates the Potential of Its PLX Cells to Treat Crohn's Disease and Ulcerative Colitis," May 28, 2008, available at http://www.pluristem.com/old_press/28_05_2008.htm.

(Continued)

*Primary Examiner* — Emily Cordas
(74) *Attorney, Agent, or Firm* — Wolf, Greenfield & Sacks, P.C.

(57) ABSTRACT

A method of treating ulcerative colitis or Crohn's disease in a subject in need thereof is disclosed. The method comprising administering to the subject a therapeutically effective amount of adherent cells from a placenta or adipose tissue, thereby treating the ulcerative colitis or Crohn's disease.

14 Claims, 16 Drawing Sheets

(56) References Cited

OTHER PUBLICATIONS

Zhang et al., "Comparison of Mesenchymal Stem Cells from Human Placenta and Bone Marrow," Chinese Medical Journal (Jun. 1, 2004), 117(6):882-87.

Musina et al., "Differentiation Potential of Mesenchymal Stem Cells of Different Origin," *Cell Technologies in Biology & Medicine* (Jan. 2006), 2(1):147-51.

Sakaguchi et al., "Comparison of Human Stem Cells Derived From Various Mesenchymal Tissues," *Arthritis & Rheumatism* (Aug. 2005), 52(8)2521-29.

Mariotti et al., "Comparative Characteristics of Mesenchymal Stem Cells from Human Bone Marrow and Placenta: CD10, CD49d, and CD56 Make a Difference," *Stem Cells and Development* (Dec. 2008), 17:1039-42.

National Institutes of Health, "View of NCT00294112 on Feb. 29, 2008," Feb. 29, 2008, available at http://clinicaltrials.gov/archive/NCT00294112/2008_02_29.

[No Author Listed] List of autoimmune and autoimmune-related diseases. American autoimmune related diseases association, Inc. Last accessed at https://www.aarda.org/research_display.php?ID=47. On Mar. 21, 2013.

[No Author Listed] Stem cells in the treatment of multiple myeloma. Oncology and Hematology. Nov. 21, 2011. Last accessed at http://www.medlinks.ru/article.php?sid=47654 on Feb. 12, 2015.

Dominici et al., Minimal criteria for defining multipotent mesenchymal stromal cells. The International Society for Cellular Therapy position statement. Cytotherapy. 2006;8(4):315-7.

Lazebnik et al., [Use of allogeneic mesenchymal stem cells in the treatment of intestinal inflammatory diseases]. Ter Arkh. 2010;82(2):38-43. Russian. Abstract only.

[No Author Listed] TMS-008-C | Alizarin-Red Staining Solution. EMD Millipore. 2015. Last accessed from http://www.emdmillipore.com/US/en/product/Alizarin-Red-Staining-Solution,MM_NF-TMS-008-C on Dec. 9, 2015.

Carter et al., Guidelines for the management of inflammatory bowel disease in adults. Gut. Sep. 2004;53 Suppl 5:V1-16.

Portmann-Lanz et al., Placental mesenchymal stem cells as potential autologous graft for pre- and perinatal neuroregeneration. Am J Obstet Gynecol. Mar. 2006;194(3):664-73.

* cited by examiner adipogenesis differentiation medium osteogenesis differentiation medium growth medium adipogenesis differentiation medium osteogenesis differentiation medium growth medium

METHODS OF TREATING INFLAMMATORY COLON DISEASES

CROSS REFERENCE TO RELATED APPLICATIONS

This application is a National Phase Application of International Application Number PCT/IL2009/000527, filed May 26, 2009, and claims the benefit of U.S. Provisional Application No. 61/071,944, filed May 27, 2008, the content of all of which are incorporated herein by reference.

FIELD AND BACKGROUND OF THE INVENTION

The present invention, in some embodiments thereof, relates to methods of treating inflammatory colon diseases using adherent cells from adipose or placenta tissues and, more particularly, but not exclusively, to methods of treating ulcerative colitis or Crohn's disease using the adherent cells.

In the developing medical world a growing need exists for large amounts of adult stem cells for the purpose of cell engraftment and tissue engineering. In addition, adult stem cell therapy is continuously developing for treating and curing various conditions such as hematopoietic disorders, heart disease, Parkinson's disease, Alzheimer's disease, stroke, burns, muscular dystrophy, autoimmune disorders, diabetes and arthritis.

In recent years, considerable activity has focused on the therapeutic potential of mesenchymal stromal cells (MSCs) for various medical applications including tissue repair of damaged organs such as the brain, heart, bone and liver and in support of bone marrow transplantations (BMT). MSCs, a heterogeneous population of cells obtained from e.g. bone marrow, adipose tissue, placenta, and blood, is capable of differentiating into different types of mesenchymal mature cells (e.g. reticular endothelial cells, fibroblasts, adipocytes, osteogenic precursor cells) depending upon influences from various bioactive factors. Accordingly, MSCs have been widely studied in regenerative medicine as the foundation to build new tissues such as bone, cartilage and fat for the repair of injury or replacement of pathologic tissues and as treatment for genetic and acquired diseases. Furthermore, the multipotent ability of MSCs, their easy isolation and culture, as well as their high ex vivo expansion potential make them an attractive therapeutic tool.

Inflammatory bowel disease (IBD), a group of inflammatory conditions of the large intestine and small intestine, includes Crohn's disease and ulcerative colitis and is a chronic, relapsing, and remitting condition of an unknown origin which affects at least 1 in 1,000 people in Western countries.

Crohn's disease (also known as granulomatous colitis and regional enteritis), an autoimmune disease caused by the immune system's attacking the gastrointestinal tract and producing inflammation in the gastrointestinal tract, is an inflammatory disease that may affect any part of the gastrointestinal tract from mouth to anus, causing a wide variety of symptoms. It primarily causes abdominal pain, diarrhea, vomiting and weight loss, but may also cause complications outside of the gastrointestinal tract such as skin rashes, arthritis and inflammation of the eye. There is currently no known drug or surgical cure for Crohn's disease and treatment options are restricted to controlling symptoms, maintaining remission and preventing relapse (e.g. 5-aminosalicylic acid (5-ASA) formulations, corticosteroids such as prednisone and hydrocortisone, and immunomodulators such as azathioprine and mercaptopurine).

Ulcerative colitis, a form of colitis, is a disease of the intestine, specifically the large intestine or colon that includes characteristic ulcers, or open sores, in the colon. The main symptom of active disease is usually constant diarrhea mixed with blood. Current treatment of ulcerative colitis includes anti-inflammatory drugs, immunosuppression, and biological therapy targeting specific components of the immune response. Colectomy (partial or total removal of the large bowel through surgery) is occasionally necessary, and is considered to be a cure for the disease.

Okamoto et al. [Okamoto et al., supra] and Matsumoto et al. [Matsumoto et al., Gastroenterology (2005) 128: 1851-1867] reported that bone-marrow-derived cells (BMDCs) can repopulate the epithelia of the human gastrointestinal tract after graft-versus-host disease or gastric ulcer formation following irradiation and bone marrow transplantation. Komori et al. 2005 [Komori et al., J Gastroenterol (2005) 40: 591-599] also reported transient increases in bone-marrow-derived mucosal epithelial cells and myofibroblasts during the healing process of gastric ulcers and trinitrobenzene sulfonic acid (TNBS)-induced colitis in rats. In addition, Osiris therapeutics (www.osiris.com) is evaluating Prochymal, a product derived from bone marrow MSCs, for the treatment of Crohn's disease. Osiris is currently conducting a multi-center trial to evaluate the safety and efficacy of Prochymal for Crohn's disease.

PCT Publication No. WO 2008/100498 discloses methods of treating immune-related diseases (e.g. inflammatory bowel disease, graft-versus-host disease) using placental stem cells or umbilical cord stem cells. The stem cells disclosed are derived from a mammalian placenta, regardless of morphology, cell surface markers or the number of passages after a primary culture, and adhere to a tissue culture substrate (e.g., tissue culture plastic or a fibronectin-coated tissue culture plate).

U.S. Publication No. 20080213227 discloses methods of treating autoimmune diseases and inflammatory diseases (e.g. inflammatory bowel disease and Crohn's disease) by administering mesenchymal stem cells in an effective amount. The mesenchymal cells disclosed may be obtained from adherent marrow or periosteal cells or alternatively from blood, skin, cord blood, muscle, fat, bone, or perichondrium.

PCT Publication No. WO 2007/108003 discloses methods of cell expansion, which comprise culturing adherent cells from placenta or adipose tissue under three-dimensional culturing conditions, which support cell expansion. Also provided are cells generated thereby and uses of same.

SUMMARY OF THE INVENTION

According to an aspect of some embodiments of the present invention there is provided a method of treating ulcerative colitis or Crohn's disease in a subject in need thereof, the method comprising administering to the subject a therapeutically effective amount of adherent cells from a placenta or adipose tissue, thereby treating the ulcerative colitis or Crohn's disease.

According to an aspect of some embodiments of the present invention there is provided a use of adherent cells from a placenta or adipose tissue for the manufacture of a medicament identified for treating ulcerative colitis or Crohn's disease.

According to an aspect of some embodiments of the present invention there is provided an article of manufacture comprising a packaging material which comprises a label for use in treating ulcerative colitis or Crohn's disease, the packaging material packaging a pharmaceutically effective amount of adherent cells from a placenta or adipose tissue.

According to some embodiments of the invention, the adherent cells comprise a positive marker expression selected from the group consisting of CD73, CD90, CD29 and CD105.

According to some embodiments of the invention, the adherent cells comprise a negative marker expression selected from the group consisting of CD3, CD4, CD45, CD80, HLA-DR, CD11b, CD14, CD19, CD34 and CD79.

According to some embodiments of the invention, the adherent cells are capable of suppressing an immune reaction.

According to some embodiments of the invention, suppressing an immune reaction comprises suppressing a T cell activity.

According to some embodiments of the invention, the adherent cells are obtained from a three-dimensional (3D) culture.

According to some embodiments of the invention, the three-dimensional (3D) culture comprises a 3D bioreactor.

According to some embodiments of the invention, culturing of the adherent cells in the 3D culture is effected under perfusion.

According to some embodiments of the invention, culturing of the adherent cells is effected for at least 3 days.

According to some embodiments of the invention, culturing of the adherent cells is effected until at least 10% of the adherent cells are proliferating.

According to some embodiments of the invention, the adherent cells comprise a gene expression profile as described in Table 11.

According to some embodiments of the invention, the adherent cells comprise cells cultured from the placenta or adipose tissue under 2 dimensional (2D) culturing conditions.

According to some embodiments of the invention, at least 12% of the adherent cells are at a S and/or G2/M proliferative phase.

According to some embodiments of the invention, the adherent cells comprise a gene expression profile as described in Table 8.

According to some embodiments of the invention, the adherent cells are less committed to an osteogenic lineage as compared to adherent cells from bone marrow grown and allowed to differentiate under the same conditions.

According to some embodiments of the invention, the adherent cells are less committed to an adipogenic lineage as compared to adherent cells from bone marrow grown and allowed to differentiate under the same conditions.

According to some embodiments of the invention, the article of manufacture further comprises an additional drug for treatment of colon inflammation.

According to some embodiments of the invention, the article of manufacture further comprises an immunosuppressant agent.

According to some embodiments of the invention, the article of manufacture further comprises an anti-inflammatory agent.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 7A depicts negative expression of the endothelial marker CD31; FIG. 7B depicts negative expression of the endothelial marker KDR; and FIG. 7C depicts positive expression of the human fibroblast marker (D7-FIB). Of note, the red histograms for Isotype IgG1 (FITC) represent the negative control while the blue histograms represent the positively stained cells.

FIG. 8A depicts PLX-C expression of CD80; FIG. 8B depicts PLX-C expression of CD86; FIG. 8C depicts PLX-C expression of CD40; and FIG. 8D depicts PLX-C expression of HLA-A/B/C. Negative controls were prepared with relevant isotype fluorescence molecules. Of note, red histograms indicate PLX-C marker-expressing population of cells, blue histograms indicate bone marrow (BM) marker-expressing population of cells, and green histograms indicate mononuclear cell (MNC) marker expressing population of cells.

FIG. 9A depicts Mixed Lymphocyte Reaction (MLR) tests performed with $2 \times 10^5$ peripheral blood (PB) derived mononuclear cells (MNC, donor A) stimulated with equal amount of irradiated (3000 Rad) PB derived MNCs (donor B) followed by addition of increasing amounts of PLX-C cells to the cultures. Three replicates of each group were seeded in 96-well plates. Proliferation rate was measured by [$^3$H]thymidine incorporation; FIG. 9B depict peripheral blood (PB) derived MNCs stimulated with ConA (1.5 mg/ml). Increasing amounts of PLX-C cells were added to the cultures. Three replicates of each group were seeded in 96-well plates. Proliferation rate was measured by [$^3$H]thymidine incorporation.

FIGS. 10A-B depict secretion of IFNγ (FIG. 10A) and TNFα (FIG. 10B) following co-culture of human derived MNCs (isolated from peripheral blood) stimulated with ConA with PLX-C; FIG. 10C depicts secretion of IFNγ, TNFα and IL-10 following co-culture of human derived MNCs (isolated from peripheral blood) stimulated with LPS with PLX-C. Supernatants were collected and subjected to cytokines analysis using ELISA.

DESCRIPTION OF SPECIFIC EMBODIMENTS OF THE INVENTION

The present invention, in some embodiments thereof, relates to methods of treating inflammatory colon diseases using adherent cells from adipose or placenta tissues and, more particularly, but not exclusively, to methods of treating ulcerative colitis or Crohn's disease using the adherent cells.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventor has surprisingly uncovered that adherent cells from placental tissues may be used effectively to treat uleceritive colitis and Crohn's disease.

Figure 11:
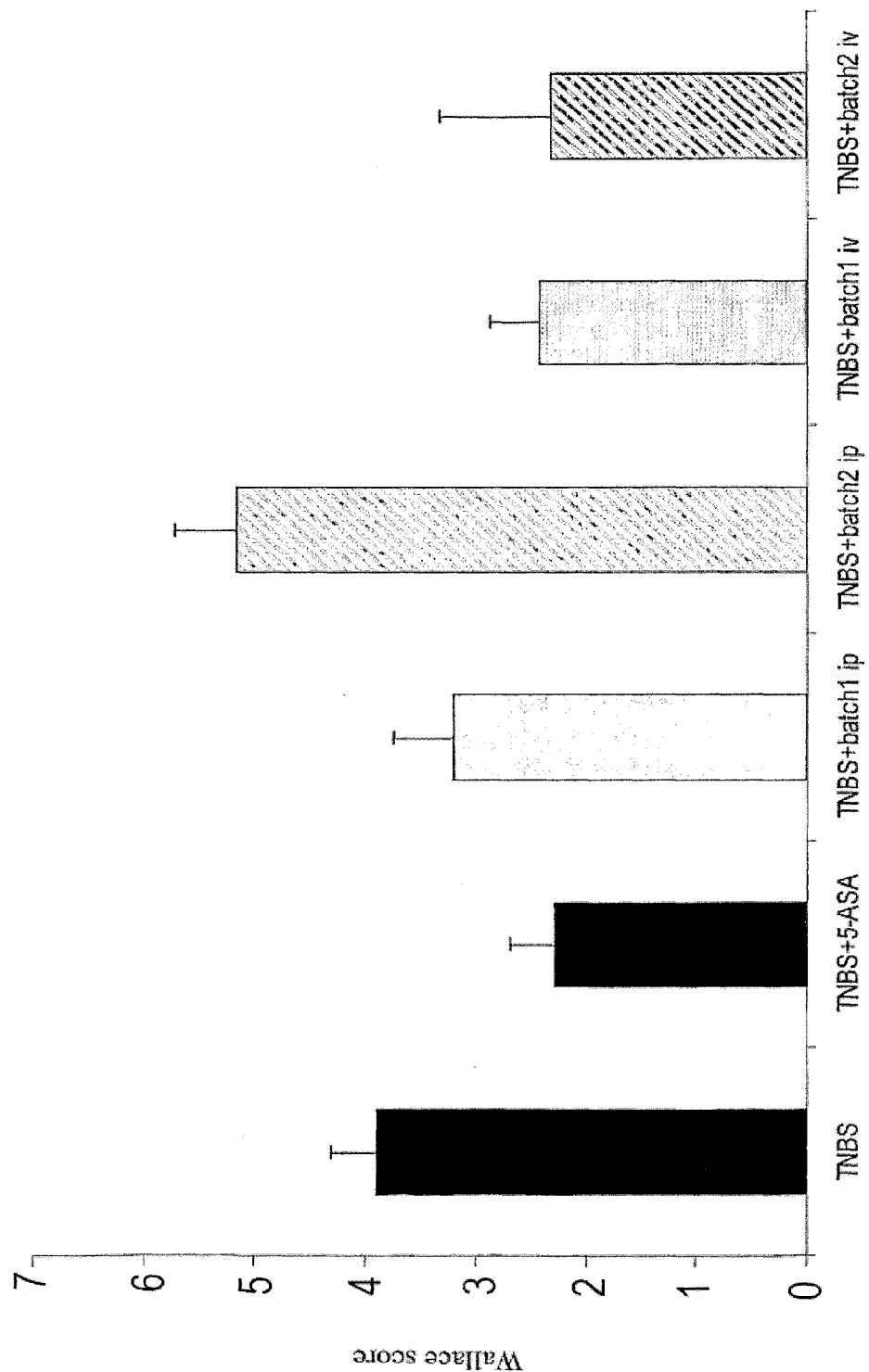
FIG. 11 is a graph depicting macroscopic evaluation of colon tissues of colitic mice as represented by the Wallace score. TNBS (colitis model mice), TNBS+5-ASA (colitic mice who received the gold standard treatment), TNBS+2D adherent cells (batch 1) ip, TNBS+3D adherent cells (PLX-C, batch 2) ip, TNBS+2D adherent cells (batch 1) iv and TNBS+3D adherent cells (PLX-C, batch 2) iv. Macroscopic assessments were conducted blindly by two investigators.
Figure 12:
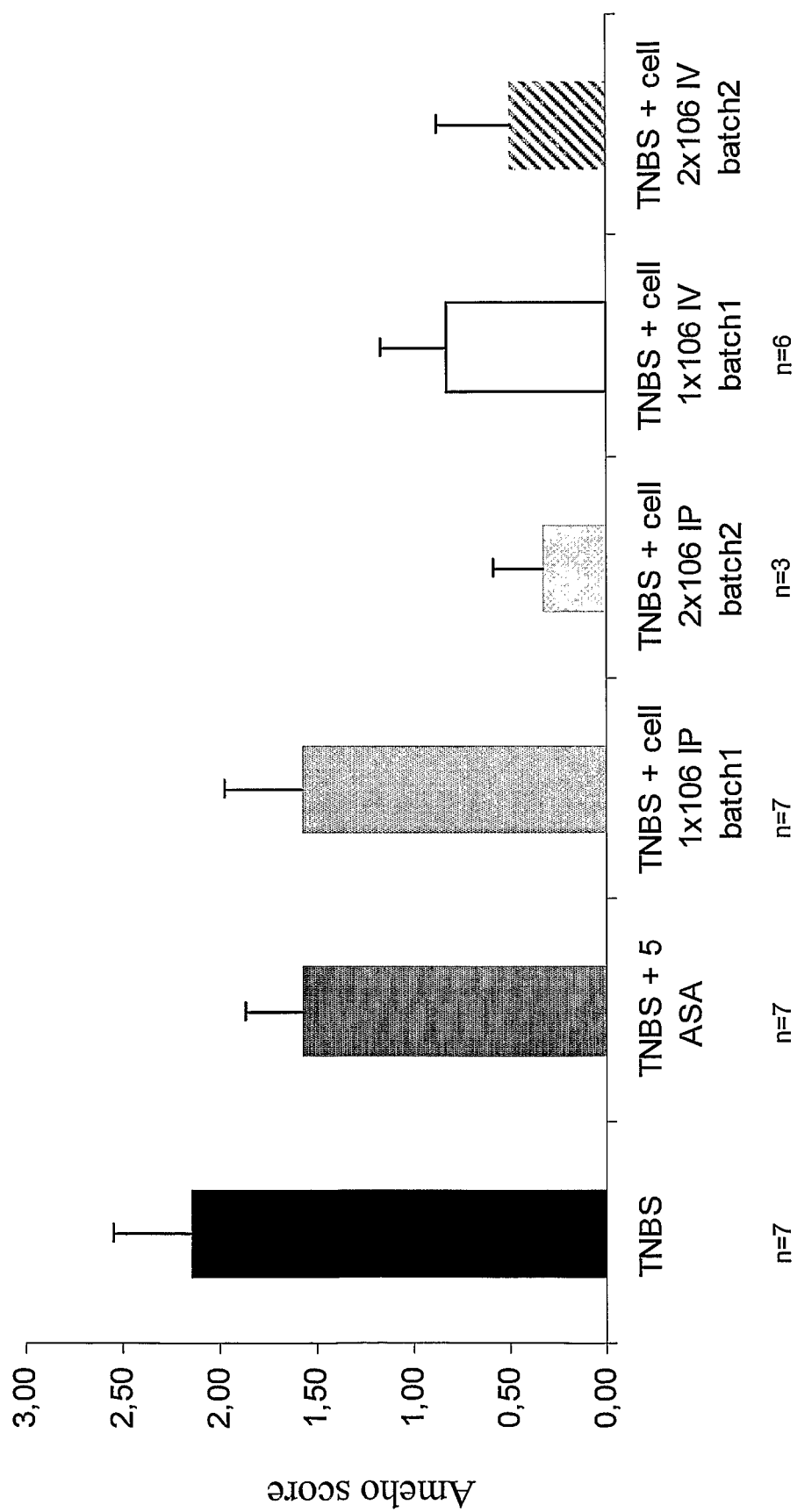
FIG. 12 is a graph depicting microscopic evaluation of colon tissues of colitic mice as represented by the Ameho score. TNBS (colitis model mice), TNBS+5-ASA (colitic mice who received the gold standard treatment), TNBS+2D adherent cells (batch 1) ip, TNBS+3D adherent cells (PLX-C, batch 2) ip, TNBS+2D adherent cells (batch 1) iv and TNBS+3D adherent cells (PLX-C, batch 2) iv. Histological assessments were conducted blindly by two investigators.
Figure 14:
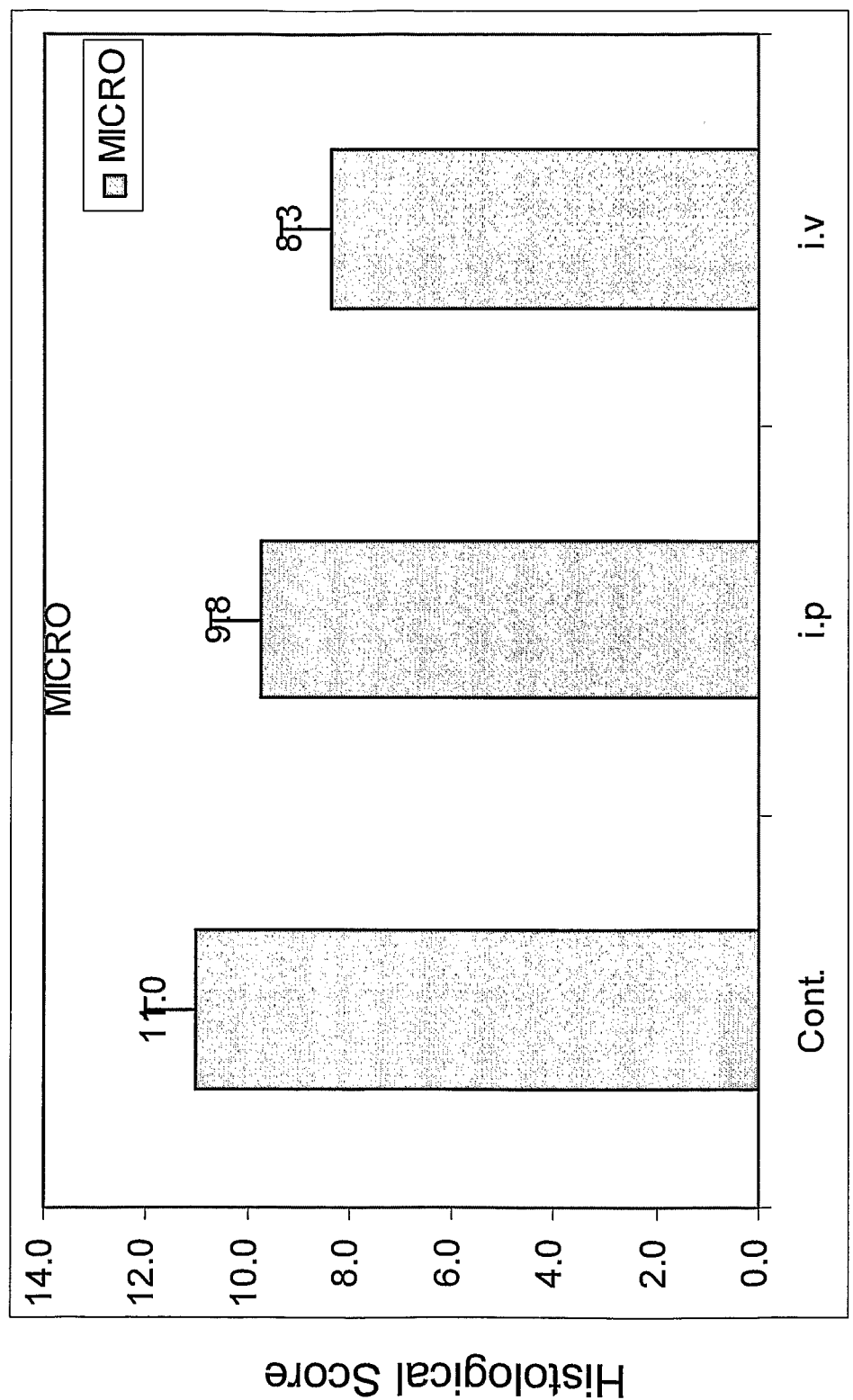
FIG. 14 is a graph depicting microscopic evaluation of colon tissues of colitic rats. Rats were rendered colitic by intracolonic administration of TNBS and were administered PLX-C cells via intraperitoneal (ip) or intravenous (iv) routes.

As is shown hereinbelow and in the Examples section which follows, the present inventor has uncovered through laborious experimentation that adherent cells obtained from placenta or adipose tissues and cultured under 2D (Example 2) or 3D culturing conditions (Examples 1 and 3) may be effectively used to treat colon inflammation, such as ulcerative colitis, as depicted in both mouse (Example 4) and rat (Example 5) experimental models. The present inventor has shown that intravenous (iv) or intraperitoneal (ip) administration of the 2D or 3D adherent cells of the present invention resulted in a major improvement in the inflammatory condition of the colon tissue as determined by both macroscopic and microscopic evaluations of the colon (FIGS. 11, 12 and 14). This anti-inflammatory effect was as efficient as the 5-ASA gold standard treatment. Taken together the present teachings portray an anti-inflammatory value for the adherent cells of the present invention and suggest the use of same for the treatment of inflammatory colon diseases such as ulcerative colitis and Crohn's disease.

Thus, according to one aspect of the present invention there is provided a method of treating ulcerative colitis or Crohn's disease in a subject in need thereof, the method comprising administering to the subject a therapeutically effective amount of adherent cells from a placenta or adipose tissue, thereby treating the ulcerative colitis or Crohn's disease.

As used herein the term "treating" refers to preventing, curing, reversing, attenuating, alleviating, minimizing, suppressing or halting the deleterious effects of ulcerative colitis or Crohn's disease. Those of skill in the art will understand that various methodologies and assays can be used to assess the development of a pathology, and similarly, various methodologies and assays may be used to assess the reduction, remission or regression of a pathology.

The term "ulcerative colitis" as used herein refers to a medical condition of the intestine, a form of inflammatory bowel disease (IBD), specifically of the large intestine or colon, that includes characteristic ulcers, or open sores, in the colon. Ulcerative colitis disease is usually diagnosed following recurrent symptoms of constant diarrhea mixed with blood, of gradual onset. Ulcerative colitis according to the present teachings refers to any stage or severity of ulcerative colitis (e.g. disease remission or acute disease).

The term "Crohn's disease" as used herein refers to an inflammatory condition that may affect any part of the gastrointestinal tract from mouth to anus, also known as granulomatous colitis or regional enteritis, and is a form of inflammatory bowel disease (IBD). Crohn's disease is a type of autoimmune disease and is usually diagnosed following recurrent symptoms of abdominal pain, diarrhea (which may be bloody), vomiting, weight loss, skin rashes, arthritis and inflammation of the eye. Crohn's disease according to the present teachings refers to any stage or severity of Crohn's disease (e.g. disease remission, acute disease, relapse).

As used herein the phrase "a subject in need thereof" refers to a mammal, preferably a human subject, male or female of any age, who has been diagnosed with probable or definite ulcerative colitis or Crohn's disease, e.g., a subject who experienced inflammatory colon disease. The diagnosis of ulcerative colitis or Crohn's disease may include any diagnosis test as, for example, laboratory tests, endoscopic evaluation, biopsies of the mucosa (for ulcerative colitis), barium follow-through x-ray (for Crohn's disease), and CT or MRI scans (for Crohn's disease).

It will be appreciated that the present invention also envision treatment of other colon inflammatory conditions, including, but are not limited to, chronic inflammatory intestinal diseases (Garcia Herola A. et al., Gastroenterol. Hepatol. 2000 January; 23 (1):16), celiac disease (Landau Y E. and Shoenfeld Y. Harefuah 2000 Jan. 16; 138 (2):122) and ileitis using the adherent cells of the present invention.

As mentioned hereinabove, the method, according to this aspect of the present invention, is effected by administering to the subject a therapeutically effective amount of adherent cells from a placenta or adipose tissue.

As used herein the phrase "adherent cells" refers to a homogeneous or heterogeneous population of cells which are anchorage dependent, i.e., require attachment to a surface in order to grow in vitro.

As used herein the phrase "adipose tissue" refers to a connective tissue which comprises fat cells (adipocytes).

As used herein the term "placenta tissue" refers to any portion of the mammalian female organ which lines the uterine wall and during pregnancy envelopes the fetus, to which it is attached by the umbilical cord. Following birth, the placenta is expelled (and is referred to as a post partum placenta). In an exemplary embodiment, placenta refers to whole placenta.

According to the present teachings, placenta or adipose tissue derived adherent cells can be propagated using two dimensional (2D) or three dimensional (3D) culturing conditions.

As used herein the phrase "two dimensional culture" refers to a culture in which the cells are disposed to conditions which are compatible with cell growth while allowing the cells to grow in one plane. The conditions in the two dimensional culture of the invention are designed to enable expansion of the adherent cells.

As used herein the phrase "three dimensional culture" refers to a culture in which the cells are disposed to conditions which are compatible with cell growth while allowing the cells to grow in more than one layer. It is well appreciated that the in situ environment of a cell in a living organism (or a tissue) is in a three dimensional architecture. Cells are surrounded by other cells. They are held in a complex network of extra cellular matrix nanoscale fibers that allows the establishment of various local microenvironments. Their extra cellular ligands mediate not only the attachment to the basal membrane but also access to a variety of vascular and lymphatic vessels. Oxygen, hormones and nutrients are ferried to cells and waste products are carried away. The conditions in the three dimensional culture of the invention are designed to mimic such an environment as is further exemplified below.

It will be appreciated that the conditions of the two-dimensional and three-dimensional cultures are such that enable expansion of the adherent cells.

As used herein the terms "expanding" and "expansion" refer to substantially differentiation-less maintenance of the cells and ultimately cell growth, i.e., increase of a cell population (e.g., at least 2 fold) without differentiation accompanying such increase.

As used herein the terms "maintaining" and "maintenance" refer to substantially differentiation-less cell renewal, i.e., substantially stationary cell population without differentiation accompanying such stationarity.

As mentioned, the adherent cells of this aspect of the invention are retrieved from an adipose or placental tissue.

Placental cells may be obtained from a full-term or preterm placenta. Placenta is preferably collected once it has been ex blooded. The placenta is preferably perfused for a period of time sufficient to remove residual cells. The term "perfuse" or "perfusion" used herein refers to the act of pouring or passaging a fluid over or through an organ or tissue. The placental tissue may be from any mammal; for example, the placental tissue is human. A convenient source of placental tissue is from a post partum placenta (e.g., 1-6 hours), however, the source of placental tissue or cells or the method of isolation of placental tissue is not critical to the invention.

Placenta derived adherent cells may be obtained from both fetal (i.e., amnion or inner parts of the placenta, see Example 1) and maternal (i.e., decidua basalis, and decidua parietalis) parts of the placenta. Tissue specimens are washed in a physiological buffer [e.g., phosphate-buffered saline (PBS) or Hank's buffer]. Single-cell suspensions are made by treating the tissue with a digestive enzyme (see below) or/and mincing and flushing the tissue parts through a nylon filter or by gentle pipetting (Falcon, Becton, Dickinson, San Jose, Calif.) with washing medium.

Adipose tissue derived adherent cells may be isolated by a variety of methods known to those skilled in the art. For example, such methods are described in U.S. Pat. No. 6,153, 432. The adipose tissue may be derived from omental/visceral, mammary, gonadal, or other adipose tissue sites. One source of adipose tissue is omental adipose. In humans, the adipose is typically isolated by liposuction.

Isolated adherent cells from placenta or adipose tissue may be derived by treating the tissue with a digestive enzyme such as collagenase, trypsin and/or dispase; and/or effective concentrations of hyaluronidase or DNAse; and ethylenediaminetetra-acetic acid (EDTA); at temperatures between 25-50° C., for periods of between 10 minutes to 3 hours. The cells may then be passed through a nylon or cheesecloth mesh filter of between 20 microns to 1 mm. The cells are then subjected to differential centrifugation directly in media or over a Ficoll or Percoll or other particulate gradient. Cells are centrifuged at speeds of between 100 to 3000×g for periods of between 1 minutes to 1 hour at temperatures of between 4-50° C. (see U.S. Pat. No. 7,078,230).

In addition to placenta or adipose tissue derived adherent cells, the invention also envisages the use of adherent cells from other cell sources which are characterized by stromal stem cell phenotype (as will be further described herein below). Tissue sources from which adherent cells can be retrieved include, but are not limited to, cord blood, scalp, hair follicles [e.g. as described in Us Pat. App. 20060172304], testicles [e.g., as described in Guan K., et al., Nature. 2006 Apr. 27; 440(7088):1199-203], human olfactory mucosa [e.g., as described in Marshall, C T., et al., Histol Histopathol. 2006 June; 21(6):633-43], embryonic yolk sac [e.g., as described in Geijsen N, Nature. 2004 Jan. 8; 427(6970):148-54] and amniotic fluid [Pieternella et al. (2004) Stem Cells 22:1338-1345], all of which are known to include mesenchymal stem cells. Adherent cells from these tissue sources can be isolated by culturing the cells on an adherent surface, thus isolating adherent cells from other cells in the initial population.

Regardless of the origin (e.g., placenta or adipose tissue), cell retrieval is preferably effected under sterile conditions. Once isolated cells are obtained, they are allowed to adhere to an adherent material (e.g., configured as a surface) to thereby isolate adherent cells. Culturing then proceeds under 2D conditions (as described in Example 2 of the Examples section) and cells may be further transferred to 3D conditions (as described in Examples 1 and 3 of the Examples section).

As used herein "an adherent material" refers to a synthetic, naturally occurring or a combination of same of a non-cytotoxic (i.e., biologically compatible) material having a chemical structure (e.g., charged surface exposed groups) which may retain the cells on a surface.

Examples of adherent materials which may be used in accordance with this aspect of the invention include, but are not limited to, a polyester, a polypropylene, a polyalkylene, a polyfluorochloroethylene, a polyvinyl chloride, a polystyrene, a polysulfone, a cellulose acetate, a glass fiber, a ceramic particle, a matrigel, an extra cellular matrix component (e.g., fibronectin, chondronectin, laminin), a collagen, a poly L lactic acid and an inert metal fiber.

It will be appreciated that seeding of placenta or adipose cells is typically effected at a culture density of $3\pm0.2\times10^3$ cells/cm$^2$. Following seeding, cell cultures are usually cultured in a tissue culture incubator under humidified conditions with 5% CO2 at 37° C.

Further steps of purification or enrichment for stromal stem cells may be effected using methods which are well known in the art (such as by FACS using stromal stem cell marker expression, as further described herein below).

Non-limiting examples of base media useful in culturing according to the invention include Minimum Essential Medium Eagle, ADC-1, LPM (Bovine Serum Albumin-free), F10 (HAM), F12 (HAM), DCCM1, DCCM2, RPMI 1640, BGJ Medium (with and without Fitton-Jackson Modification), Basal Medium Eagle (BME-with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E-with Earle's sale base), Medium M199 (M199H-with Hank's salt base), Minimum Essential Medium Eagle (MEM-E-with Earle's salt base), Minimum Essential Medium Eagle (MEM-H-with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the invention is DMEM. These and other useful media are available from GIBCO, Grand Island, N.Y., USA and Biological Industries, Bet HaEmek, Israel, among others. A number of these media are summarized in Methods in Enzymology, Volume LVIII, "Cell Culture", pp. 62 72, edited by William B. Jakoby and Ira H. Pastan, published by Academic Press, Inc.

The medium may be supplemented such as with serum such as fetal serum of bovine or other species, and optionally or alternatively, growth factors, vitamins (e.g. ascorbic acid), cytokines, salts (e.g. B-glycerophosphate), steroids (e.g. dexamethasone) and hormones e.g., growth hormone, erythropoeitin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor, fibroblast growth factor, nerve growth factor, cilary neurotrophic factor, platelet derived growth factor, and bone morphogenetic protein at concentrations of between picogram/ml to milligram/ml levels.

It is further recognized that additional components may be added to the culture medium. Such components may be antibiotics, antimycotics, albumin, amino acids, and other components known to the art for the culture of cells. Additionally, components may be added to enhance the differentiation process when needed (see further below).

It will be appreciated that in case the adherent cells of the invention are administered to a human subject, the cells and the culture medium (e.g., with the above described medium additives) should be substantially xeno-free, i.e., devoid of any animal contaminants e.g., mycoplasma. For example, the culture medium can be supplemented with a serum-replacement, human serum and/or synthetic or recombinantly produced factors.

As mentioned, once adherent cells are at hand they may be passaged to 2D or 3D settings (see Examples 1, 2 and 3 of the Examples section which follows). It will be appreciated though, that the cells may be transferred to a 3D-configured matrix immediately after isolation or alternatively, may be passaged to 3D settings following 2D conditions (as mentioned hereinabove).

It will be appreciated that during the 2D culturing conditions, the adherent cells may be continuously passaged. According to an embodiment of the present invention, the cells may be passaged for at least 4 passages, at least 5 passages, at least 6 passages, at least 7 passages or at least 8 passages. It will be appreciated that cells are typically passaged when the culture reaches about 70-80% confluence, typically after 3-5 days (1.5-2 doublings). Moreover, under the 2D culturing conditions, the cells may be grown in a culture medium devoid of antibiotic supplements from at least passage 2, at least passage 3, or at least passage 4.

Thus, during the 2D culture, culturing is effected for at least about 2 days, 3 days, 4 days, 5 days, 10 days, 20 days, a month or even more. Passaging may also be effected to increase cell number. It will be appreciated that culture medium may be changed in order to prolong and improve culturing conditions.

The 2D adherent cells can be harvested when at least about 12% of cells are proliferating while avoiding uncontrolled differentiation and senescence.

2D adherent cells of some embodiments of the present invention comprise at least about 10%, 28%, 30%, 50%, 80% or more proliferative cells (as can be assayed by FACS monitoring S and/or G2/M phases).

As mentioned, the adherent cells may be transferred to 3D settings.

Thus, the adherent material of this aspect of the invention is configured for 3D culturing thereby providing a growth matrix that substantially increases the available attachment surface for the adherence of the cells so as to mimic the infrastructure of the tissue (e.g., placenta).

For high scale production, culturing can be effected in a 3D bioreactor.

Examples of such bioreactors include, but are not limited to, a plug flow bioreactor, a continuous stirred tank bioreactor, a stationary-bed bioreactor, a CelliGen Plus® bioreactor system (New Brunswick Scientific (NBS) or a BIOFLO 310 bioreactor system (New Brunswick Scientific (NBS).

As shown Example 3 of the Examples section, the Celligen bioreactor is capable of 3D expansion of adherent cells under controlled conditions (e.g. pH, temperature and oxygen levels) and with constant cell growth medium perfusion. Furthermore, the cell cultures can be directly monitored for concentration levels of glucose, lactate, glutamine, glutamate and ammonium. The glucose consumption rate and the lactate formation rate of the adherent cells enable to measure cell growth rate and to determine the harvest time.

Other 3D bioreactors that can be used with the invention include, but are not limited to, a continuous stirred tank bioreactor, where a culture medium is continuously fed into the bioreactor and a product is continuously drawn out, to maintain a time-constant steady state within the reactor. A stirred tank bioreactor with a fibrous bed basket is available for example at New Brunswick Scientific Co., Edison, N.J.), A stationary-bed bioreactor, an air-lift bioreactor, where air is typically fed into the bottom of a central draught tube flowing up while forming bubbles, and disengaging exhaust gas at the top of the column], a cell seeding perfusion bioreactor with Polyactive foams [as described in Wendt, D. et al., Biotechnol Bioeng 84: 205-214, (2003)] tubular poly-L-lactic acid (PLLA) porous scaffolds in a Radial-flow perfusion bioreactor [as described in Kitagawa et al., Biotechnology and Bioengineering 93(5): 947-954 (2006). Other bioreactors which can be used in accordance with the invention are described in U.S. Pat. Nos. 6,277,151, 6,197,575, 6,139,578, 6,132,463, 5,902,741 and 5,629,186.

Cell seeding is preferably effected 100,000-1,500,000 cells/mm at seeding. In an exemplary embodiment a total of $150\pm30\times10^6$ cells are seeded, $3\text{-}5\times10^6$ cell/gr carrier are seeded, or $0.015\text{-}0.1\times10^6$ cell/ml are seeded.

Culturing is effected for at least about 2 days, 3 days, 4 days, 5 days, 10 days, 20 days, a month or even more. It will be appreciated that culturing in a bioreactor may prolong this period. Culturing of the adherent cells in the 3D culture can be effected under a continuous flow of a culture medium. Passaging may also be effected to increase cell number. It will be appreciated that culture medium may be changed in order to prolong and improve culturing conditions.

According to an embodiment of the present invention, culturing the adherent cells in a 3D culture may be effected under perfusion of the culture medium. Typically, the perfusion rate is determined by the glucose concentration in the culture medium of the adherent cells. Thus, according to the present teachings, the culture medium may be changed when the glucose concentration is about 500 mg/L, about 550 mg/L, or about 600 mg/L.

The 3D adherent cells can be harvested when at least about 10% of cells are proliferating while avoiding uncontrolled differentiation and senescence.

3D adherent cells of some embodiments of the present invention comprise at least about 10%, 28%, 30%, 50%, 80% or more proliferative cells (as can be assayed by FACS monitoring S and/or G2/M phases).

Adherent cells of some embodiments of the invention may comprise at least one "stromal stem cell phenotype".

As used herein "a stromal stem cell phenotype" refers to a structural or functional phenotype typical of a bone-marrow derived stromal (i.e., mesenchymal) stem cell As used herein the phrase "stem cell" refers to a cell which is not terminally differentiated.

Thus for example, the cells may have a spindle shape. Alternatively or additionally the cells may express a marker or a collection of markers (e.g. surface marker) typical to stromal stem cells. Examples of stromal stem cell surface markers (positive and negative) include but are not limited to CD105+, CD29+, CD44+, CD73+, CD90+, CD3−, CD4−, CD34−, CD45−, CD80−, CD19−, CD5−, CD20−, CD11B−, CD14−, CD19−, CD79−, HLA-DR−, and FMC7−. Other stromal stem cell markers include but are not limited to tyrosine hydroxylase, nestin and H—NF.

According to a specific embodiment of the present invention, the adherent cells do not express Oct-4.

It will be appreciated that the 2D adherent cells of placenta tissue generated according to the present teachings have a gene expression profile essentially as described in Table 8 of the Examples section which follows. While, the 3D adherent cells of placenta tissue generated according to the present teachings have a gene expression profile essentially as described in Table 11 of the Examples section which follows.

According to an exemplary embodiment, the 2D and 3D adherent cells of the present invention are less committed to differentiation into osteogenic or adipogenic lineages as compared to adherent cells from the bone marrow grown and differentiated under the same conditions.

Examples of functional phenotypes typical of stromal stem cells include, but are not limited to, T cell suppression activity (they don't stimulate T cells and conversely suppress same) and hematopoietic stem cell support activity.

According to one embodiment of the invention, the adherent cells of the invention are capable of suppressing immune reaction in a subject.

As used herein the phrase "suppressing immune reaction in a subject" refers to decreasing or inhibiting the immune reaction occurring in a subject in response to an antigen (e.g., a foreign cell or a portion thereof). The immune response which can be suppressed by the adherent cells include the humoral immune responses, and cellular immune responses, which involve specific recognition of pathogen antigens via antibodies and T-lymphocytes (proliferation of T cells), respectively.

As is shown in Examples 4-5 of the Examples section which follows, the 2D and 3D adherent cells of the present invention were found to induce an anti-inflammatory effect in colon inflammatory conditions. It will be further appreciated that this effect may be mediated by the cells per se or by a factor secreted thereby having an anti-inflammatory effect even in the absence of cells. Thus, the adherent cells of the present invention may be preferentially used in treating intestinal inflammation, such as in conditions of ulcerative colitis and Crohn's disease.

The phrase "administering to the subject" refers to the introduction of the cells of the invention to target tissue. The cells can be derived from the recipient or from an allogeneic or xenogeneic donor. This phrase also encompasses "transplantation", "cell replacement" or "grafting" of the cells of the invention into the subject.

According to specific embodiments of the invention, the adherent cells may be administered to the subject by any means known to one of ordinary skill in the art, for example, by intravenous (iv), intramuscular (im), or intraperitoneal (ip) administration.

Cells which may be administered in accordance with this aspect of the invention include the above-described adherent cells which may be cultured in three-dimensional or two dimensional settings as well as mesenchymal and-non mesenchymal partially or terminally differentiated derivatives of same.

Methods of deriving lineage specific cells from the stromal stem cells of the invention are well known in the art. See for example, U.S. Pat. Nos. 5,486,359, 5,942,225, 5,736,396, 5,908,784 and 5,902,741.

The cells may be naïve or genetically modified such as to derive a lineage of interest (see U.S. Pat. Appl. No. 20030219423).

The cells may be of autologous or non-autologous source (i.e., allogeneic or xenogeneic) of fresh or frozen (e.g., cryopreserved) preparations.

Since non-autologous cells may induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylidene-acetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents which may be used include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

Depending on the medical condition, the subject may be administered with additional chemical drugs (e.g., immunomodulatory, chemotherapy, anti-inflammatory etc.) or cells.

For the treatment of inflammatory colon conditions, including ulcerative colitis and Crohn's disease, any treatment known to one of ordinary skill in the art may be employed, including for example, Aminosalicylates (e.g. Sulfasalazine, Mesalazine, Balsalazide, Olsalazine), Corticosteroids (e.g. Cortisone, Prednisone, Prednisolone, Cortifoam, Hydrocortisone, Methylprednisolone, Beclometasone, Budesonide), Immunosuppressive drugs (e.g. Mercaptopurine, Azathioprine, Methotrexate, Tacrolimus), Biological treatments (e.g. Infliximab, Visilizumab), Low Molecular Weight Heparin (LMWH), dietary modifications (e.g. fibers) and surgery.

The subject may also be administered an anti-inflammatory agent such as, but not limited to, Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; llonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone;

Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

In any of the methods described herein, the cells can be administered either per se or, preferably as a part of a pharmaceutical composition that further comprises a pharmaceutically acceptable carrier.

As used herein a "pharmaceutical composition" refers to a preparation of the adherent cells of the invention (i.e., adherent cells from placenta or adipose tissue, which are obtained from a 2D or 3D culture), with other chemical components such as pharmaceutically suitable carriers and excipients. The purpose of a pharmaceutical composition is to facilitate administration of the cells to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the invention, the pharmaceutical carrier is an aqueous solution of saline.

Techniques for formulation and administration of drugs may be found in "Remington's Pharmaceutical Sciences," Mack Publishing Co., Easton, Pa., latest edition, which is incorporated herein by reference.

One may administer the pharmaceutical composition in a systemic manner (as detailed hereinabove). Alternatively, one may administer the pharmaceutical composition locally, for example, via injection of the pharmaceutical composition directly into a tissue region of a patient.

Pharmaceutical compositions of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, physiological salt buffer, or freezing medium containing cryopreservents. For transmucosal administration, penetrants appropriate to the barrier to be permeated are used in the formulation. Such penetrants are generally known in the art.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1).

Dosage amount and interval may be adjusted individually to levels of the active ingredient which are sufficient to effectively regulate the neurotransmitter synthesis by the implanted cells. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition.

Models for inflammatory colon diseases include animal models of ulcerative colitis such as, but are not limited to, trinitrobenzene sulfonic acid (TNBS)-induced colitis in rats and mice [Komori et al., J Gastroenterol (2005) 40: 591-599; and Examples 4-5 hereinbelow].

Compositions including the preparation of the invention formulated in a compatible pharmaceutical carrier may also be prepared, placed in an appropriate container, and labeled for treatment of an indicated condition.

Compositions of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

The adherent cells of the invention can be suitably formulated as pharmaceutical compositions which can be suitably packaged as an article of manufacture. Such an article of manufacture comprises a label for use in treating ulcerative colitis or Crohn's disease, the packaging material packaging a pharmaceutically effective amount of adherent cells from a placenta or adipose tissue.

It will be appreciated that the article of manufacture may further comprise additional drugs for the treatment of colon inflammatory conditions including, for example, anti-inflammatory agents, immunomodulatory agents, anti-inflammatory agents, and other drugs for the treatment of inflammatory colon conditions (as described in further detail hereinabove).

As used herein the term "about" refers to ±10%.

The terms "comprises", "comprising", "includes", "including", "having" and their conjugates mean "including but not limited to".

The term "consisting of means" including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Methods of Generating Placenta Derived 3D Adherent Cells

Adherent cells were produced as was previously described (see WO/2007/108003) in a bioreactor system containing 3D carriers to produce 3D-adherent cells (designated herein as PLX).

Materials and Experimental Procedures

Placenta Derived Adherent Cells

Inner parts of a full-term delivery placenta (Bnei Zion medical center, Haifa, Israel) were cut under sterile conditions, washed 3 times with Hank's Buffer and incubated for 3 hours at 37° C. with 0.1% Collagenase (1 mg/ml tissue; Sigma-Aldrich, St. Lewis, Mo.). Using gentle pipetting, suspended cells were then washed with DMEM supplemented with 10% FCS, Pen-Strep-Nystatin mixture (100 U/ml:100 µg/ml:1.25 un/ml) and 2 mM L-glutamine, seeded in 75 cm$^2$ flasks and incubated at 37° C. in a tissue culture incubator under humidified condition with 5% $CO_2$.

Two Dimensional (2D) Cell Growth

Cells were allowed to adhere to a plastic surface for 72 hours after which the media was changed every 3-4 days. After 2-3 passages, the cells were cryopreserved, thawed and seeded for a secondary growth in flasks. When reaching 60-80% confluence cells were detached from the growth flask using 0.25% trypsin-EDTA and seeded into new flasks (usually every 3-5 days), for another 2-5 passages. Cultured cells were thereafter collected for analysis or for culturing in bioreactors.

PluriX™ Plug Flow Bioreactor

The PluriX™ Plug Flow bioreactor (Pluristem, Haifa, Israel; see U.S. Pat. No. 6,911,201 and WO/2007/108003), was loaded with 1-100 ml packed 3D porrosive carriers (4 mm in diameter) made of a non woven fabric matrix of polyester. These carriers enable the propagation of large cell numbers in a relatively small volume. Glassware was designed and manufactured by Pluristem (Pluristem, Haifa, Israel). The bioreactor was maintained in an incubator of 37° C., with flow rate regulated and monitored by a valve, and peristaltic pump. The bioreactor contains a sampling and injection point, allowing the sequential seeding of cells. Culture medium was supplied at pH 6.7-7.4 from a reservoir. The reservoir was supplied by a filtered gas mixture, containing air/$CO_2$/$O_2$ at differing proportions, depending on cell density in the bioreactor. The $O_2$ proportion was suited to the level of dissolved $O_2$ at the bioreactor exit, determined by a monitor. The gas mixture was supplied to the reservoir via silicone tubes or diffuser (Degania Bet, Emek Hayarden, Israel). The culture medium was passed through a separating container which enables collection of circulating, nonadherent cells. Circulation of the medium was obtained by a peristaltic pump. The bioreactor was further equipped with an additional sampling point and containers for continuous medium exchange.

Production of 3D-Adherent Cells (PLX)

Non-confluent primary human adherent 2D cell cultures, grown as described above, were trypsinized, washed, resuspended in DMEM supplemented with 10% FBS, Pen-Strep-Nystatin mixture (100 U/ml:100 ug/ml:1.25 un/ml) and 2 mM L-glutamine, and seeded ($10^3$-$10^5$ cells/ml) via an injection point onto the 3D carriers in a sterile Plug Flow bioreactor. Prior to inoculation, bioreactor was filled with PBS-Ca—Mg (Biological Industries, Beit Ha'emek, Israel), autoclaved (120° C., 30 min) and washed with Dulbecco's growth medium containing 10% heat-inactivated fetal calf serum and a Pen-Strep-Nystatin mixture (100 U/ml:100 ug/ml:1.25 un/ml). Flow was kept at a rate of 0.1-5 ml/min. Seeding process involved cease of circulation for 2-48 hrs, thereby allowing the cells to settle on the carriers. Bioreactor was kept under controlled temperature (37° C.) and pH conditions (pH=6.7-7.4); using an incubator supplied with sterile air and $CO_2$ as needed. Growth medium was replaced 2-3 times a week. Circulation medium was replaced with fresh DMEM media, every 4 hr to 7 days. At a density of $1\times10^6$-$1\times10^7$ cells/ml (following 12-40 days of growth), total medium volume was removed from the bioreactor and bioreactor and carriers were washed 3-5 times with PBS. 3D-adherent cells were then detached from the carriers with Trypsin-EDTA; (Biological Industries, Beit Ha'emek, Israel; 3-15 minutes with gentle agitation, 1-5 times), and were thereafter resuspended in DMEM and cryopreserved.

Example 2

Methods of Generating 2D Adherent Cells Suitable for Use in Accordance with the Present Teachings and the 2D Adherent Cells Generated Thereby 2D adherent cells were produced which exhibit different characteristics then the above described 3D adherent cells (PLX, Example 1). Next, 2D adherent cells from bone marrow or placenta origin were grown under osteocyte or adipocyte differentiation stimulating conditions.

Materials and Experimental Procedures

Manufacturing Process of 2D Adherent Cells

Receipt of Human Tissue

All placentas obtained were received from the maternity ward under approval of the Helsinki Committee of the medical facility. Accordingly, all placenta donors signed an informed consent and Donor Screening and Donor Testing was performed (IPC1). Immediately after taking the placenta from the donor (during the caesarean procedure), it was placed in a sterile plastic bag and then in a Styrofoam box with ice packs. The placenta was delivered and immediately placed in a quarantine area until released to use by Quality Control (QC) and Quality Assurance (QA). All the following production steps were performed in a quarantine, clean room facility until QC approval of mycoplasma test results arrived and the cells were release for 2D cell growth.

Recovery and Processing of Adherent Cells

To initiate the process, the placenta was cut into pieces under aseptic conditions under laminar flow hood, washed with Hank's buffer solution and incubated for 3 hours at 37° C. with 0.1% Collagenase (1 mg Collagenase/ml tissue). 2D cell medium (2D-Medium comprising DMEM supplemented with 10% FBS, fungizone 0.25 µg/ml and gentamycine 50 µg/ml) was added and the digested tissue was roughly filtered through a sterile metal strainer, collected in a sterile beaker and centrifuged (10 minutes, 1200 RPM, 4° C.). Using gentle pipeting, suspended cells were then washed with 2D-Medium supplemented with antibiotics, seeded in 80 $cm^2$ flasks and incubated at 37° C. in a tissue culture incubator under humidified condition supplemented with 5% $CO_2$. Following 2-3 days, in which the cells were allowed to adhere to the flask surface, they were washed with PBS and 2D-Medium was added.

Two Dimensional (2D) Cell Growth

Prior to the first passage, growth medium samples of 10% of the total flask number in quarantine was pooled and taken for mycoplasma testing (IPC2). If cells were found to be negative for Mycoplasma (EZ-PCR Mycoplasma kit, Biological Industries, Israel), cells were released from quarantine. After 1-2 additional passages, cells were transferred to the 2D production clean room (2DP). Once in Room 2DP, culture was continued for another 3-5 passages (of note, cells were grown in 2D-Medium supplemented with antibiotics until passage 2, thereafter cells were grown in 2D-Medium without antibiotics). IPC-3 sample was taken for immune phenotype after passage 4. Throughout the process, cultures were grown in a tissue culture incubator under humidified conditions with 5% CO2 at 37° C. After a total of 6-8 passages (9-16 cell doublings), cells were collected and cryopreserved as the 2D-Cell Stock (2DCS).

The first passage was usually carried out after 10-15 days. Beginning at passage 2 and continuing until passage 6-8, cells were passaged when the culture reached 70-80% confluence, usually after 3-5 days (1.5-2 doublings). The cells were detached from the flasks using 0.25% trypsin-EDTA (4 minutes at 37° C.) and seeded in a culture density of $3\pm0.2\times10^3$ cells/$cm^2$. The size of the tissue culture flasks raised as the passages proceed. The culturing process started in 80 $cm^2$ tissue culture flask, continued in 175 $cm^2$, then in 500 $cm^2$ (Triple flask) and finally the cells were seeded into Cell Factory 10 tray (6320 $cm^2$).

Prior to cryopreservation, at the end of 2DCS growth period, the growth medium was collected and the sample was prepared to be sent to an approved GLP laboratory for Mycoplasma test (IPC 4).

Cryopreservation Procedure for 2D-Cell-Stock Product

For 2DCS cryopreservation, 2D-cultured cells were collected under aseptic conditions using 0.25% trypsin-EDTA. The cells were centrifuged (1200 RPM, 10', 4° C.), counted and re-suspended in 2D-Medium.

For freezing, cell suspensions were diluted. 1:1 with 2D-Freezing Mixture (final concentrations was 10% DMSO, 40% FBS and 50% 2D-Medium). Approximately 1.5-2.5×$10^9$ cells were manufactured from one placenta. 4 ml of the cells were stored at a final concentration of $10 \times 10^6$/ml in 5 ml cryopreservation polypropylene vials. The vials were labeled and transferred to a controlled rate freezer for a graduated temperature reducing process (1° C./min), after which they were transferred to storage in gas-phase of a liquid nitrogen freezer located in the Cold Storage Room. This material was referred to as the 2D-Cell Stock (2DCS) batch.

Cell Cycle Analysis 2D adherent cells and PLX cells were fixed with 70% EtOH O.N, centrifuged and re-suspended in a Propidium Iodide (PI) solution containing 2 µg/ml PI (Sigma), 0.2 mg/ml Rnase A (Sigma) and 0.1% (v/v) Triton (Sigma) for 30 minutes. Cell cycle was analyzed by FACS.

Gene Expression Array (Microarray)

Adherent cells were obtained from human full term placentas and were expanded by 2D cultures or according to the teachings of WO/2007/108003 (as described in detail in Examples 1-2). Three different batches of cells were obtained from each of the expansion methods for further examination.

RNA was extracted from the cells (Qiagen-Rneasy micro kit) and applied to an Affymetrix whole genome expression array GeneChip® Human Exon 1.0 ST Array (Affymetrix, Santa Clara, Calif., USA).

FACS Analysis of Membrane Markers

Cells were stained with monoclonal antibodies as previously described. In short, 400,000-600,000 cells were suspended in 0.1 ml flow cytometer buffer in a 5 ml test tube and incubated for 15 minutes at room temperature (RT), in the dark, with each of the following monoclonal antibodies (MAbs): FITC-conjugated anti-human CD29 MAb (eBioscience), PE conjugated anti human CD73 MAb (Becton Dickinson), PE conjugated anti human CD105 MAb (eBioscience), PE conjugated anti human CD90 MAb (Becton Dickinson), FITC-conjugated anti-human CD45 MAb (IQProducts), PE-conjugated anti-human CD19 MAb (IQProducts), PE conjugated anti human CD14 MAb (IQProducts), FITC conjugated anti human HLA-DR MAb (IQProduct), PE conjugated anti human CD34 MAb (IQProducts), FITC conjugated anti human CD31 MAb (eBioscience), FITC conjugated anti human KDR MAb (R&D systems), anti human fibroblasts marker (D7-FIB) MAb (ACRIS), FITC-conjugated anti-human CD80 MAb (BD), FITC-conjugated anti-human CD86 MAb (BD), FITC-conjugated anti-human CD40 MAb (BD), FITC-conjugated anti-human HLA-ABC MAb (BD), Isotype IgG1 FITC conjugated (IQ Products), Isotype IgG1 PE conjugated (IQ Products).

Cells were washed twice with flow cytometer buffer, resuspended in 500 µl flow cytometer buffer and analyzed by flow cytometry using FC-500 Flow Cytometer (Beckman Coulter). Negative controls were prepared with relevant isotype fluorescence molecules.

Immunomodulation Assay

Human derived mononuclear cells (MNCs) were isolated from peripheral blood. Suspension of 200,000 MNCs per 200 µl medium (RPMI 1640 medium containing 20% FBS per 96 well) were stimulated with 10 µg PHA/ml (SIGMA) in the presence of 20,000 2D adherent cells for 5 days under humidified 5% $CO_2$ at 37° C. Four different batches of 2D adherent cells were used. Three replicates of each group were seeded in 96-well plated. During the last 18 hrs of the 5-day culture, cells were pulsed with 1 µC $^3$H-thymidine and further harvested over fiberglass filter. Thymidine uptake was quantified by a scintillation counter.

Induction of Osteogenesis in 2D Adherent Cells

Osteogenesis was carried out according to Chemicon osteogenesis kit (cat no. scr028, Millipore, Mass., USA)

Osteogenesis Induction Medium

Osteogenesis induction medium was freshly made prior to each medium exchange using the kit components (See Table 1, below).

TABLE 1

Osteogenesis medium components

| Component | Stock concentration | Amount | Final con |
| --- | --- | --- | --- |
| DMEM low glucose (Invitrogen, Gibco) | | 8.7 ml | 87% |
| Serum (heat inactivated) | | 1 ml | 10% |
| dexamethasone | 1 mM | 1 µl | 0.1 µM |
| Asorbic Acid-2-Phosphate solution | 0.1M | 20 µl | 0.2 mM |
| Glycerol-2-Phosphate Solution | 1M | 100 µL | 10 Mm |
| L-glutamine | X 100 | 100 µl | X 1 |
| Pen & Strep | X 100 | 100 µl | X 1 |

To arrive at 1 mM dexamethasone solution, 900 µl ethanol was added to 100 µl dexamethasone 10 mM solution. Stock solution was stored with the rest of the kit's components at −20° C. A 50 ml serum vial was heat inactivated, divided into 5 ml aliquots and kept at −20° C. until use.

Coating 24-Well Tissue Culture Plates

A coating mixture comprising 12 µg/ml vitronectin and 12 µg/ml collagen (both included in the kit) was prepared by diluting each with 1×PBS.

The coating mixture was then added to the wells to cover the well surfaces (5 wells×2 plates were prepared). Plates were incubated overnight at room temperature. The coating mixture was then removed and the wells were rinsed once with PBS. Plates were aspirated right before use.

Cell Growth

Placenta derived cells (plc11-3-1) or bone marrow derived cells (BM108) were plated (200,000 cells per well) in 1 ml growth medium comprising DMEM (Invitrogen, Gibco), 10% FCS (Invitrogen, Gibco), 2 Mm L-glutamine (Sigma-Aldrich), 45 µg/ml Gentamicin-IKA (Teva Medical) and 0.25 µg/ml Fungizone (Invitrogen, Gibco). Placenta derived cells (4 wells×2 plates) or bone marrow derived cells (1 well×2 plates) were grown until 100% confluent (typically overnight) before initiating osteogenic differentiation.

When cells reached 100% confluence, growth medium was aspirated and replaced with 1 ml osteogenesis induction medium (differentiation day 1). Osteogenesis induction medium was replaced with fresh medium every 2-3 days for a total of 14-17 days.

As a control, one of the two plates (for each of the cell types) was not incubated with osteogenesis differentiation medium but rather with the growth medium (described hereinabove).

On day 17, osteocytes were fixed and stained with Alizarin Red Solution as depicted in detail below.

Staining Protocol

Osteocyte staining was performed by first carefully aspirating the medium from each well (carefully as to not aspirate the cells). Cells were then fixed by incubating in iced cold 70% ethanol for 1 hour at room temperature. The alcohol was then carefully aspirated and the cells were rinsed twice with water (5-10 minutes each wash). The water was then aspirated and alizarin red solution (500-1000 µl) was added to the cells. Cells were incubated with alizarin red solution at room temperature for 30 minutes. Alizarin red was removed and the cells were washed 4 times with 1 ml water and aspirated after each wash. Finally, 1-1.5 ml water was added to each well to prevent cell drying. The plates were microscopically visualized by an inverted Nikon microscope.

Induction of Osteogenesis in Modified Osteogenesis Induction Medium (2D Adherent Cells)

Osteogenesis induction medium was freshly made prior to each medium exchange using the components listed in Table 2, below, along with Vitamin D.

TABLE 2

Osteogenesis medium components

| Component | Stock con | Amount | Final con |
|---|---|---|---|
| DMEM high glucose (Biological Industries, Bet Haemek, Israel) | | 8.7 ml | 87% |
| L-glutamine | X 100 | 100 µl | X 1 |
| Serum (heat inactivated) | | 1 ml | 10% |
| Dexamethasone (Chemicon) | 10 mM | 10 µl | 10 µM |
| Asorbic Acid-2-Phosphate solution (Chemicon) | 0.1M | 20 µl | 0.2 mM |
| Glycerol-2-Phosphate Solution (Chemicon) | 1M | 100 µL | 10 Mm |
| Vitamin D (Sigma) | 10 µM | 10 µL | 10 nM |
| Gentamycin (Biological Industries, Bet Haemek, Israel) | X 100 | 100 µl | X 1 |

A 50 ml serum vial was heat inactivated, divided into 5 ml aliquots and kept at −20° C. until use.

Coating 48-Well Tissue Culture Plates

A coating mixture comprising 12 µg/ml vitronectin and 12 µg/ml collagen (both from Chemicon) was prepared by diluting each with 1×PBS.

The coating mixture was then added to the wells to cover the well surfaces (5 wells×2 plates were prepared). Plates were incubated overnight at room temperature. The coating mixture was then removed and the wells were rinsed once with PBS. Plates were aspirated right before use.

Cell Growth

Placenta derived cells (PLC 8-2-1, PLC 15 3-4-2 or PLC 19-4-3-1 fetal cells) were plated (100,000 cells per well) in 0.5 ml growth medium comprising DMEM (Invitrogen, Gibco), 10% FCS (Invitrogen, Gibco), 2 Mm L-glutamine (Sigma-Aldrich), 45 µg/ml Gentamicin-IKA (Teva Medical) and 0.25 µg/ml Fungizone (Invitrogen, Gibco) (4 wells×2 plates). Bone marrow derived cells (BM109) were plated (150,000 cells per well) in 0.5 ml growth medium (as described above) (1 well×2 plates). Cells were grown until 100% confluent (typically overnight) before initiating osteogenic differentiation.

When cells reached 100% confluence, growth medium was aspirated and replaced with 0.5 ml osteogenesis induction medium (differentiation day 1). Osteogenesis induction medium was replaced with fresh medium every 2-3 days for a total of 26 days.

As a control, one of the two plates (for each of the cell types) was not incubated with osteogenesis differentiation medium but rather with the growth medium (described hereinabove).

On day 26, osteocytes were fixed and stained with Alizarin Red Solution as depicted in detail below.

Staining Protocol

Osteocyte staining was performed by first carefully aspirating the medium from each well (carefully as to not aspirate the cells). Cells were then fixed by incubating in iced cold 70% ethanol for 1 hour at room temperature. The alcohol was then carefully aspirated and the cells were rinsed twice with water (5-10 minutes each wash). The water was then aspirated and alizarin red solution (500-1000 µl) was added to the cells. Cells were incubated with alizarin red solution at room temperature for 30 minutes. Alizarin red was removed and the cells were washed 4 times with 1 ml water and aspirated after each wash. Finally, 1-1.5 ml water was added to each well to prevent cell drying. The plates were microscopically visualized by an inverted Nikon microscope.

Induction of Adipogenesis in 2D Adherent Cells

Adipogenesis was carried out according to Chemicon adipogenesis kit (Chemicon adipogenesis kit, cat no. scr020, Millipore, Mass., USA)

Adipogenesis Induction Medium

Adipogenesis induction or maintenance mediums were freshly prepared prior to every medium exchange using the components depicted in Tables 3 and 4, below.

TABLE 3

Adipogenesis induction medium components

| Component | Stock con | Amount | Final con |
|---|---|---|---|
| DMEM low glucose (Biological Industries, Bet Haemek, Israel) | | 4.4 ml | 90% |
| Serum (heat inactivated) | | 0.5 ml | 10% |
| Dexamethasone (Sigma) | 10 mM | 0.5 µl | 1 µM |
| IBMX (Sigma) | 0.5M | 5 µl | 0.5 mM |
| Insulin (Sigma) | 10 mg/ml | 5 µL | 10 µg/ml |
| Indomethacin (Sigma) | 10 mM | 50 µl | 100 µM |
| Pen & Strep | X 100 | 50 µl | X 1 |

TABLE 4

Adipogenesis maintenance medium components

| Component | Stock con | Amount | Final con |
|---|---|---|---|
| DMEM low glucose | | 4.4 ml | 90% |
| Serum (heat inactivated) | | 0.5 ml | 10% |
| Insulin | 10 mg/ml | 5 µL | 10 µg/ml |
| Pen & Strep | X 100 | 50 µl | X 1 |

Cell Growth

Placenta derived cells (plc11-3-1) or bone marrow derived cells (BM108) were plated (200,000 cells per well) in 1 ml growth medium comprising DMEM (Invitrogen, Gibco), 10% FCS (Invitrogen, Gibco), 2 Mm L-glutamine (Sigma-Aldrich), 45 µg/ml Gentamicin-IKA (Teva Medical) and 0.25 µg/ml Fungizone (Invitrogen, Gibco). Placenta derived cells (4 wells×2 plates) or bone marrow derived cells (1 well×2 plates) were grown until 100% confluent (typically overnight) before initiating adipogenesis differentiation.

When cells reached 100% confluence, growth medium was aspirated and replaced with 1 ml adipogenesis induction medium (differentiation day 1). Adipogenesis induction medium was replaced with fresh medium every 2-3 days for a total of 25 days (as depicted in detail in Table 5, hereinbelow). Of note, monolayers of adipogenic cells were extremely fragile and could easily dislodged from plates, therefore, medium changes were performed with gentle medium changes to avoid disruption of the lipid droplets.

As a control, one of the two plates (for each of the cell types) was not incubated with adipogenesis differentiation medium but rather with the growth medium (described hereinabove).

TABLE 5

Adipogenesis differentiation schedule

| Day | Medium |
|---|---|
| 1 | Adipogenesis Induction medium |
| 3 | Adipogenesis Induction medium |
| 5 | Adipogenesis Induction medium |
| 7 | Adipogenesis Maintenance medium |
| 9 | Adipogenesis Induction medium |
| 11 | Adipogenesis Induction medium |
| 13 | Adipogenesis Induction medium |
| 15 | Adipogenesis Maintenance medium |
| 17 | Adipogenesis Induction medium |
| 19 | Adipogenesis Induction medium |
| 21 | Adipogenesis Induction medium |

On day 25, adipocytes were fixed and stained with oil red solution as depicted in detail below.

Staining Protocol

Adipocyte staining was performed by first carefully aspirating the medium from each well (carefully as to not aspirate the cells). Cells were then fixed by incubating in 4% Para formaldehyde for 30-40 minutes at room temperature. The fixative was then carefully aspirated and the cells were rinsed three times with PBS (5-10 minutes each wash). Next, the PBS was aspirated and the cells were rinsed twice in water. The water was then aspirated and oil red solution (500-1000 µl) was added to the cells. Cells were incubated with oil red solution at room temperature for 50 minutes. Oil red solution was removed and the cells were washed 4 times with 1 ml water and aspirated after each wash. Finally, 1-1.5 ml water was added to each well to prevent cell drying. The plates were microscopically visualized by an inverted Nikon microscope.

Preparation of Oil Red Solution

Stock of 0.25 g oil red (Sigma) was used which was dissolved in 50 ml iso-propanol by incubating 10-15 min in 37° C. bath.

For use, 30 ml of the stock stain was mixed with 20 ml DDW (left to stand for 10 minutes and then filtered with coffee filter paper). The oil red solution was prepared fresh for each use.

Induction of Adipogenesis in Modified Adipogenesis Induction Medium (2D Adherent Cells)

Adipogenesis induction medium was freshly prepared prior to every medium exchange using the components depicted in Table 6, below.

TABLE 6

Adipogenesis induction medium components

| Component | Stock con | Amount | Final con |
|---|---|---|---|
| DMEM low glucose | | 4.4 ml | 90% |
| Serum (heat inactivated) | | 0.5 ml | 10% |
| Dexamethasone (Sigma) | 1 mM | 5 µl | 1 µM |
| IBMX (Sigma) | 0.5M | 5 µl | 0.5 mM |
| Insulin (Sigma) | 10 mg/ml | 5 µL | 10 µg/ml |

TABLE 6-continued

Adipogenesis induction medium components

| Component | Stock con | Amount | Final con |
|---|---|---|---|
| Indomethacin (Sigma) | 10 mM | 200 µl | 100 µM |
| Gentamycine (Biological Industries) | | 10 µl | |

Cell Growth

Placenta derived cells (PLC 8-2-1, PLC 15 3-4-2 or PLC 19-4-3-1 fetal cells) were plated (100,000 cells per well) in 0.5 ml growth medium comprising DMEM (Invitrogen, Gibco), 10% FCS (Invitrogen, Gibco), 2 Mm L-glutamine (Sigma-Aldrich), 45 µg/ml Gentamicin-IKA (Teva Medical) and 0.25 µg/ml Fungizone (Invitrogen, Gibco) (5 wells×2 plates).

Bone marrow derived cells (BM109) were plated (100,000 cells per well) in 0.5 ml growth medium comprising DMEM (Invitrogen, Gibco), 10% FCS (Invitrogen, Gibco), 2 Mm L-glutamine (Sigma-Aldrich), 45 µg/ml Gentamicin-IKA (Teva Medical) and 0.25 µg/ml Fungizone (Invitrogen, Gibco) (4 well×2 plates). Cells were grown until 100% confluent (typically overnight) before initiating adipogenesis differentiation.

When cells reached 100% confluence, growth medium was aspirated and replaced with 0.5 ml adipogenesis induction medium (differentiation day 1). Adipogenesis induction medium was replaced with fresh medium every 2-3 days for a total of 3-4 weeks.

As a control, one of the two plates (for each of the cell types) was not incubated with adipogenesis differentiation medium but rather with the growth medium (described hereinabove).

On day 26, adipocytes were fixed and stained with oil red solution as depicted in detail below.

Staining Protocol

Adipocyte staining was performed by first carefully aspirating the medium from each well (carefully as to not aspirate the cells). Cells were then fixed by incubating in 4% Para formaldehyde for 30-40 minutes at room temperature. The fixative was then carefully aspirated and the cells were rinsed three times with PBS (5-10 minutes each wash). Next, the PBS was aspirated and the cells were rinsed twice in water. The water was then aspirated and oil red solution (500-1000 µl) was added to the cells. Cells were incubated with oil red solution at room temperature for 50 minutes. Oil red solution was removed and the cells were washed 3 times with 1 ml double distilled water and aspirated after each wash. Finally, 1-1.5 ml water was added to each well to prevent cell drying. The plates were microscopically visualized by an inverted Nikon microscope.

Preparation of Oil Red Solution

Stock of 0.25 g oil red (Sigma) was used which was dissolved in 50 ml iso-propanol by incubating 10-15 min in 37° C. bath.

For use, 30 ml of the stock stain was mixed with 20 ml DDW (left to stand for 10 minutes and then filtered with coffee filter paper). The oil red solution was prepared fresh for each use.

Results

As is illustrated in Table 7, below, processing of the 2D adherent cells suitable for use according to the present teachings differed from the 2D stage of PLX (WO/2007/108003) in a few aspects. First, the new 2D adherent cell's culture medium was supplemented with antibiotics only during the initial culturing stage (up to passage 2). Also, the new 2D adherent cells were cryopreserved only after 5-8 passages (i.e. at the end of culture) and not, as in the PLX process, during intermediate stages of 2D growth.

TABLE 7

Comparison of the 2D adherent cells suitable for use according to the present teachings to those produced for PLX in WO/2007/108003

| Parameter | WO/2007/108003 | 2D adherent cells of the present teachings |
|---|---|---|
| Tissue culture flask | 80 cm² and 175 cm² | 175 cm², triple flasks and Multi Tray |
| Medium supplemented with antibiotics | In all stages of the process | Up to passage 2 (included) |
| Cryopreservation of 2DCS | After 2-3 passages, then cryopreserved, thawed and seeded for a secondary growth in flasks for 2-5 passages, prior to seeding in bioreactor | After 5-8 passages, then cryopreserved and thawed prior to use |
| Freezing container | 2 ml cryogenic vials | 5 ml cryogenic vials |
| Freezing volume | 1-1.5 ml | 4 ml |
| Freezing method | Freezing container (contains isopropyl alcohol) | Controlled rate freezer |

Changes in the manufacturing process of the new 2D adherent cells resulted in changes in characteristics of the obtained cells. These differences are summarized hereinbelow.

Figure 1A:
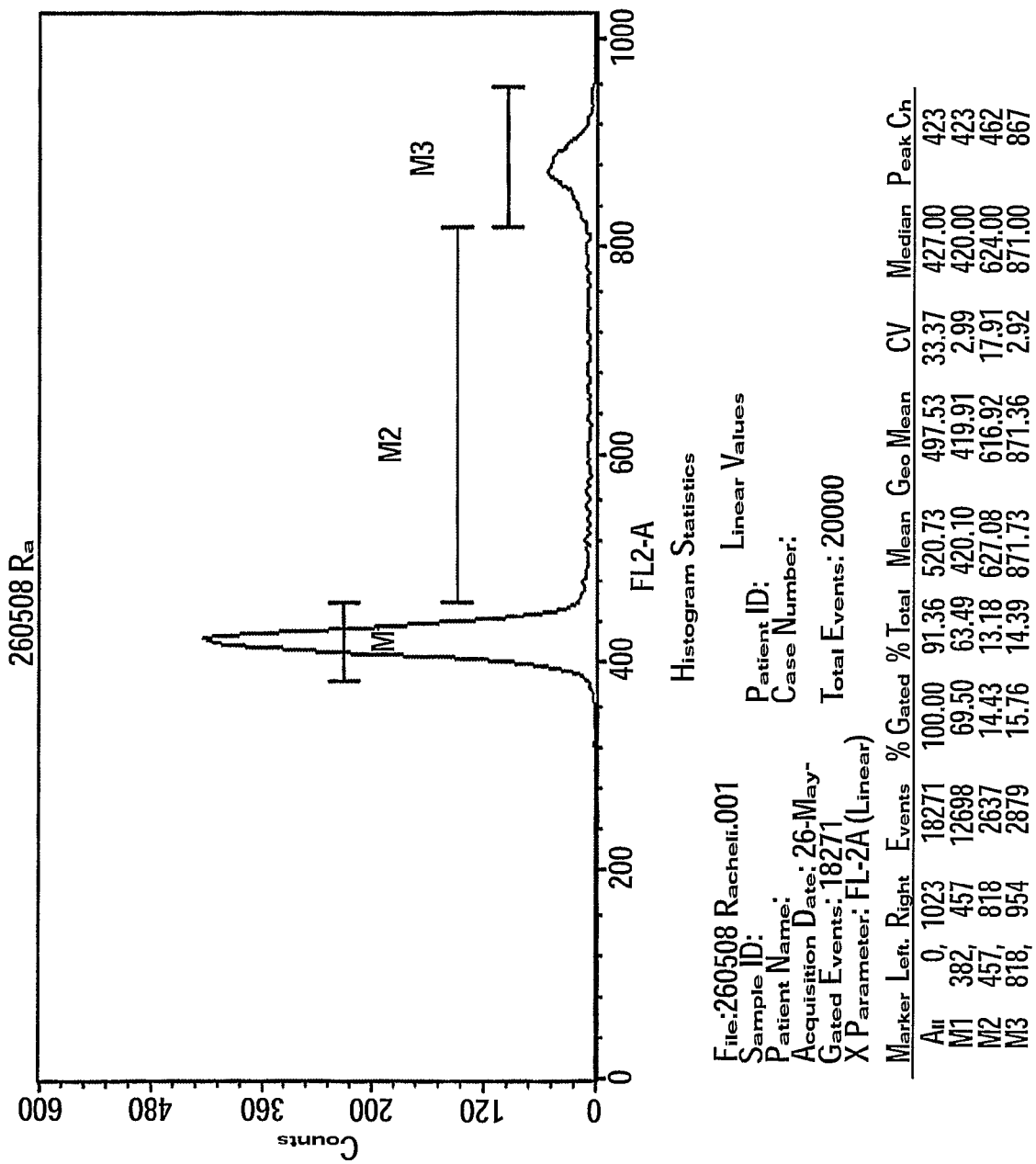
FIGS. 1A-B are figures depicting cell cycle analysis of 2D adherent cells of placenta suitable for use in accordance with the present teachings (FIG. 1A) or adherent cells manufactured according to the teachings of WO/2007/108003, designated PLX (FIG. 1B). Cells were fixed in 70% EtOH O.N, centrifuged and re-suspended in a Propidium Iodide (PI) solution and then analyzed by FACS.

Cell cycle analysis of 2D adherent cells compared to 3D adherent cells of WO/2007/108003—2D adherent cells were compared to 3D adherent cells in order to examine the distribution of the cells between the different phases of the cell cycle. As is clear from FIGS. 1A-B, 2D adherent cells exhibited typical proliferating profile (distribution of cells between the different phases of cell cycle). Specifically, 28% of cells were in S and G2/M phases (FIG. 1A). These results indicated that cells were harvested during proliferation and that the culturing conditions supported cell growth.

Figure 1B:
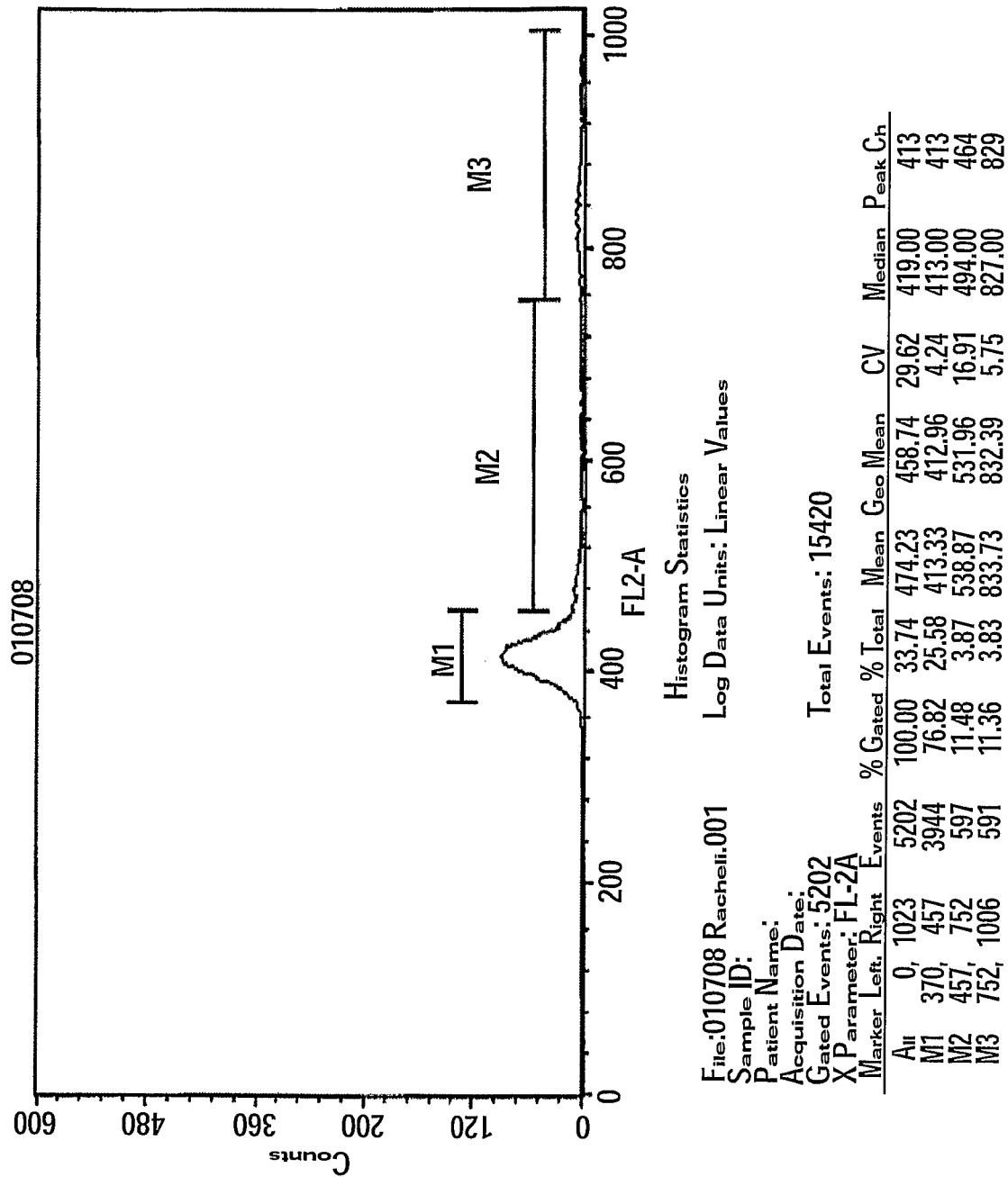

Conversely, 3D adherent cells exhibited lower rates of proliferating cells. Less than 8% of cells were in S and G2/M phases (FIG. 1B). These results indicated that cells were harvested while low levels of proliferation were taking place and suggest that conditions in the bioreactor were suboptimal to support cell growth.

Microarray comparison between 2D cells suitable for use according to the present teachings to those obtained by the teachings of WO/2007/108003—gene expression arrays enabled to simultaneously monitor genome-wide expression profiles of adherent cells derived from human full term placentas expanded by 2D cultures or according to the teachings of WO/2007/108003 (PLX, see Example 1, hereinabove). These results enabled to assess the molecular mechanism underlying phenotypic variation between cells obtained by these different growth methods (see Table 8, below).

TABLE 8

Gene expression in 2D adherent cells suitable for use according to the present teachings compared to those expressed by PLX of WO/2007/108003

| Gene | 2D vs. Plurix (fold change) | p-value (treat) |
|---|---|---|
| interferon-induced protein with tetratricopeptide repeats | 21.82 | 0.0401812 |
| leukocyte-derived arginine aminopeptidase | 14.56 | 3.88E−06 |
| signal peptide, CUB domain, EGF-like 3 | 10.82 | 0.0255115 |
| dickkopf homolog 1 (*Xenopus laevis*) | 6.84 | 3.06E−07 |
| integrin, alpha 6 | 6.76 | 0.0411667 |
| keratin 27 pseudogene 27 | 6.39 | 0.000224998 |
| similar to Keratin, type I cytoskeletal 18 (Cytokerati | 6.24 | 0.000304949 |
| aldehyde dehydrogenase 1 family, member A1 | 5.84 | 0.00145807 |
| G protein-coupled receptor, family C, group 5, member A | 5.75 | 3.39E−05 |
| coagulation factor III (thromboplastin, tissue factor) | 5.55 | 0.012192 |
| cyclin-dependent kinase inhibitor 3 (CDK2-associated dual | 5.51 | 0.000732492 |
| G protein-coupled receptor 126 | 5.50 | 0.00197635 |
| DEP domain containing 1 | 5.41 | 0.000370513 |
| SHC SH2-domain binding protein 1 | 4.96 | 0.00430878 |
| centrosomal protein 55 kDa | 4.78 | 0.0021952 |
| interferon-induced protein with tetratricopeptide repeats | 4.66 | 0.0139777 |
| NUF2, NDC80 kinetochore complex component, homolog (*S. cere* | 4.61 | 0.00276524 |
| mal, T-cell differentiation protein-like | 4.44 | 0.00664216 |
| interferon-induced protein with tetratricopeptide repea | 4.42 | 0.00357376 |
| kinesin family member 18A | 4.33 | 0.00134108 |
| cholinergic receptor, muscarinic 2 | 4.07 | 0.0320078 |
| cell division cycle 2, G1 to S and G2 to M | 4.06 | 0.0017111 |
| non-SMC condensin I complex, subunit G | 4.06 | 0.00537097 |
| denticleless homolog (*Drosophila*) | 4.06 | 0.00141153 |
| shugoshin-like 1 (*S. pombe*) | 4.00 | 0.00101318 |
| chromosome 13 open reading frame 3 | 3.98 | 0.000548296 |
| PDZ binding kinase | 3.97 | 0.00784983 |
| lymphocyte cytosolic protein 1 (L-plastin) | 3.97 | 0.0049584 |
| WAS | 3.96 | 0.00178153 |
| cyclin E2 | 3.94 | 0.000203389 |
| cathepsin C | 3.93 | 0.00532262 |
| integrin, alpha 4 (antigen CD49D, alpha 4 subunit of VLA-4 | 3.91 | 0.0158411 |
| KIAA0101 | 3.90 | 0.0105909 |
| kinesin family member 20A | 3.90 | 0.00582352 |

TABLE 8-continued

Gene expression in 2D adherent cells suitable for use according to the present teachings compared to those expressed by PLX of WO/2007/108003

| Gene | 2D vs. Plurix (fold change) | p-value (treat) |
|---|---|---|
| opioid growth factor receptor-like 1 | 3.87 | 0.00114551 |
| anillin, actin binding protein | 3.83 | 0.010923 |
| catenin (cadherin-associated protein), alpha-like 1 | 3.76 | 7.46E−05 |
| cell division cycle 20 homolog (*S. cerevisiae*) | 3.70 | 0.00514206 |
| diaphanous homolog 3 (*Drosophila*) | 3.69 | 0.00107709 |
| family with sequence similarity 111, member B | 3.69 | 0.000125819 |
| aurora kinase A | 3.66 | 0.00632571 |
| fibroblast growth factor 7 (keratinocyte growth factor) | 3.64 | 0.0328983 |
| maternal embryonic leucine zipper kinase | 3.63 | 0.00908391 |
| Rho GDP dissociation inhibitor (GDI) beta | 3.63 | 0.00200066 |
| centromere protein N | 3.62 | 0.000540143 |
| MAD2 mitotic arrest deficient-like 1 (yeast) | 3.62 | 0.00488102 |
| thymidylate synthetase | 3.61 | 0.00685584 |
| cyclin B2 | 3.60 | 0.016544 |
| regulator of G-protein signalling 4 | 3.59 | 0.00781061 |
| chromosome 6 open reading frame 173 | 3.58 | 0.00222408 |
| hyaluronan-mediated motility receptor (RHAMM) | 3.55 | 0.00467816 |
| BUB1 budding uninhibited by benzimidazoles 1 homolog (yeast | 3.54 | 0.0108258 |
| SPC25, NDC80 kinetochore complex component, homolog (*S. ce* | 3.53 | 0.00568662 |
| establishment of cohesion 1 homolog 2 (*S. cerevisiae*) | 3.52 | 0.000773033 |
| cyclin A2 | 3.51 | 0.00965934 |
| CDC28 protein kinase regulatory subunit 2 | 3.51 | 0.0128024 |
| keratin 18 | 3.47 | 0.000514523 |
| ribonucleotide reductase M2 polypeptide | 3.46 | 0.00834059 |
| arylacetamide deacetylase-like 1 | 3.44 | 0.000902645 |
| kinesin family member 11 | 3.43 | 0.00915145 |
| Rho GTPase activating protein 11A | 3.41 | 0.00834174 |
| GINS complex subunit 1 (Psf1 homolog) | 3.39 | 0.00104515 |
| discs, large homolog 7 (*Drosophila*) | 3.38 | 0.0317074 |
| TTK protein kinase | 3.38 | 0.0112171 |
| deleted in lymphocytic leukemia, 2 | 3.38 | 0.0109528 |
| replication factor C (activator 1) 3, 38 kDa | 3.37 | 0.00109668 |
| solute carrier family 7, (cationic amino acid transporte | 3.36 | 0.00688017 |
| dual-specificity tyrosine-(Y)-phosphorylation regulated ki | 3.34 | 0.0234606 |
| kinesin family member 2C | 3.34 | 0.0059888 |
| heat shock 22 kDa protein 8 | 3.32 | 0.0219583 |
| polo-like kinase 1 (*Drosophila*) | 3.30 | 0.0140309 |
| v-myb myeloblastosis viral oncogene homolog (avian)-lik | 3.28 | 0.0043878 |
| trypsinogen C | 3.28 | 0.00416276 |
| thymidine kinase 1, soluble | 3.27 | 0.00124134 |
| NAD(P)H dehydrogenase, quinone 1 | 3.27 | 0.000282423 |
| high-mobility group box 2 | 3.24 | 0.0196872 |
| cell division cycle associated 2 | 3.24 | 0.0122226 |
| apolipoprotein B mRNA editing enzyme, catalytic polypep | 3.23 | 0.00308692 |
| serpin peptidase inhibitor, clade B (ovalbumin), member | 3.22 | 0.0190218 |
| guanine nucleotide binding protein (G protein), gamma 11 | 3.22 | 0.00140559 |
| chromosome 15 open reading frame 23 | 3.21 | 0.000147331 |
| kinesin family member 14 | 3.19 | 0.00947901 |
| transmembrane protein 154 | 3.18 | 0.0045589 |
| glycerol kinase | 3.16 | 2.66E−05 |
| KIAA1524 | 3.15 | 0.0380688 |
| coagulation factor XIII, B polypeptide | 3.14 | 0.0294465 |
| tight junction protein 2 (zona occludens 2) | 3.13 | 0.00012562 |
| nei endonuclease VIII-like 3 (*E. coli*) | 3.12 | 0.00115606 |
| pleckstrin 2 | 3.11 | 0.0304429 |
| kinesin family member 23 | 3.09 | 0.00790585 |
| Rac GTPase activating protein 1 | 3.09 | 0.00381613 |
| keratinocyte growth factor-like protein 1 | 3.07 | 0.0300588 |
| keratinocyte growth factor-like protein 1 | 3.07 | 0.0300588 |
| keratinocyte growth factor-like protein 1 | 3.07 | 0.0300588 |
| transcription factor 19 (SC1) | 3.07 | 0.00109627 |
| OCIA domain containing 2 | 3.07 | 0.00122147 |
| lung cancer metastasis-associated protein | 3.06 | 0.00148024 |
| transcription factor 19 (SC1) | 3.05 | 0.00124327 |
| transcription factor 19 (SC1) | 3.05 | 0.00124327 |
| Rho GTPase activating protein 29 | 3.05 | 0.0466211 |
| glucosaminyl (N-acetyl) transferase 1, core 2 (beta-1,6-N- | 3.05 | 0.0197148 |
| replication factor C (activator 1) 4, 37 kDa | 3.04 | 0.00164152 |
| protein regulator of cytokinesis 1 | 3.01 | 0.0325664 |
| transforming, acidic coiled-coil containing protein 3 | 2.98 | 0.0014577 |
| cancer susceptibility candidate 5 | 2.96 | 0.0330594 |

TABLE 8-continued

Gene expression in 2D adherent cells suitable for use according to the
present teachings compared to those expressed by PLX of WO/2007/108003

| Gene | 2D vs. Plurix (fold change) | p-value (treat) |
|---|---|---|
| nucleolar and spindle associated protein 1 | 2.96 | 0.00520875 |
| cyclin B1 | 2.96 | 0.0103092 |
| transmembrane protein 48 | 2.96 | 0.00458248 |
| ZW10 interactor | 2.95 | 1.88E−05 |
| endonuclease domain containing 1 | 2.95 | 0.000429245 |
| hypoxanthine phosphoribosyltransferase 1 (Lesch-Nyhan synd | 2.94 | 0.000634057 |
| fucosidase, alpha-L-2, plasma | 2.94 | 0.00540929 |
| ubiquitin-conjugating enzyme E2T (putative) | 2.93 | 0.00741886 |
| lipase A, lysosomal acid, cholesterol esterase (Wolman dise | 2.92 | 0.0167385 |
| villin 2 (ezrin) | 2.92 | 0.0131934 |
| glycerol kinase | 2.90 | 3.37E−06 |
| WD repeat domain 76 | 2.89 | 0.0023531 |
| CD97 molecule | 2.89 | 0.00994045 |
| chromosome 18 open reading frame 24 | 2.89 | 0.00347442 |
| topoisomerase (DNA) II alpha 170 kDa | 2.89 | 0.0321109 |
| integrin, alpha 3 (antigen CD49C, alpha 3 subunit of VLA-3 | 2.87 | 0.00574148 |
| family with sequence similarity 29, member A | 2.85 | 0.00111165 |
| kinesin family member 4A | 2.85 | 0.0114203 |
| BRCA1 associated RING domain 1 | 2.85 | 0.000540414 |
| serum | 2.84 | 0.0387246 |
| RAD51 homolog (RecA homolog, *E. coli*) (*S. cerevisiae*) | 2.83 | 0.000854739 |
| Fanconi anemia, complementation group I | 2.83 | 0.00464532 |
| dihydrofolate reductase | 2.82 | 0.00178879 |
| claspin homolog (*Xenopus laevis*) | 2.81 | 0.00683624 |
| ornithine decarboxylase 1 | 2.81 | 0.00144868 |
| sperm associated antigen 5 | 2.80 | 0.00906321 |
| histone cluster 1, H3b | 2.80 | 0.0304598 |
| ATPase family, AAA domain containing 2 | 2.79 | 0.00415258 |
| KIAA0286 protein | 2.79 | 0.00130563 |
| guanine nucleotide binding protein (G protein), alpha inhi | 2.76 | 0.00184597 |
| BUB1 budding uninhibited by benzimidazoles 1 homolog beta | 2.74 | 0.0166047 |
| dihydrofolate reductase pseudogene | 2.74 | 0.00141306 |
| brix domain containing 1 | 2.73 | 0.00471977 |
| cytoskeleton associated protein 2 | 2.72 | 0.0030499 |
| mitochondrial ribosomal protein S28 | 2.72 | 0.00298194 |
| polymerase (DNA directed), epsilon 2 (p59 subunit) | 2.72 | 0.00479612 |
| family with sequence similarity 72, member A | 2.72 | 0.00143248 |
| EBNA1 binding protein 2 | 2.70 | 0.00296292 |
| similar to 40S ribosomal protein SA (P40) (34 | 2.70 | 0.0385298 |
| adipose differentiation-related protein | 2.70 | 0.000331751 |
| thioredoxin reductase 1 | 2.70 | 0.000197486 |
| minichromosome maintenance complex component 5 | 2.69 | 0.00475504 |
| von Hippel-Lindau binding protein 1 | 2.69 | 0.00329061 |
| SCL | 2.68 | 0.00390288 |
| Fanconi anemia, complementation group D2 | 2.68 | 0.0281405 |
| NIMA (never in mitosis gene a)-related kinase 2 | 2.68 | 0.00289469 |
| PHD finger protein 19 | 2.68 | 0.000177604 |
| microsomal glutathione S-transferase 1 | 2.68 | 0.041701 |
| breast cancer 2, early onset | 2.68 | 0.00586847 |
| non-SMC condensin I complex, subunit H | 2.67 | 0.0216752 |
| chromosome 13 open reading frame 27 | 2.67 | 0.0234588 |
| histone cluster 1, H2bg | 2.67 | 0.000180822 |
| non-SMC condensin II complex, subunit G2 | 2.66 | 0.0130322 |
| centromere protein I | 2.64 | 0.0106816 |
| stomatin | 2.64 | 0.00387095 |
| glutathione S-transferase omega 1 | 2.63 | 0.000648379 |
| protein tyrosine phosphatase-like A domain containing | 2.62 | 0.0419644 |
| calcyclin binding protein | 2.62 | 0.00524566 |
| KIT ligand | 2.61 | 0.00641955 |
| ubiquitin-conjugating enzyme E2L 3 | 2.61 | 0.00343347 |
| serpin peptidase inhibitor, clade B (ovalbumin), member | 2.60 | 0.0030439 |
| ATPase, Ca++ transporting, plasma membrane 4 | 2.60 | 0.023011 |
| TPX2, microtubule-associated, homolog (*Xenopus laevis*) | 2.60 | 0.0253137 |
| thyroid hormone receptor interactor 13 | 2.59 | 0.0118319 |
| H2A histone family, member Z | 2.59 | 0.0129697 |
| CDC28 protein kinase regulatory subunit 1B | 2.57 | 0.0107391 |
| cell division cycle associated 3 | 2.57 | 0.006289 |
| minichromosome maintenance complex component 8 | 2.57 | 0.000841489 |
| E2F transcription factor 2 | 2.55 | 0.0496479 |
| TIMELESS interacting protein | 2.55 | 0.00771062 |

TABLE 8-continued

Gene expression in 2D adherent cells suitable for use according to the present teachings compared to those expressed by PLX of WO/2007/108003

| Gene | 2D vs. Plurix (fold change) | p-value (treat) |
|---|---|---|
| minichromosome maintenance complex component 4 | 2.54 | 0.00342054 |
| polo-like kinase 4 (*Drosophila*) | 2.53 | 0.00209633 |
| kinesin family member C1 | 2.53 | 0.00821937 |
| dihydrofolate reductase | 2.52 | 0.00307793 |
| glycerol-3-phosphate dehydrogenase 2 (mitochondrial) | 2.52 | 0.00211969 |
| TGF beta-inducible nuclear protein 1 | 2.51 | 0.0365579 |
| integrin, alpha 2 (CD49B, alpha 2 subunit of VLA-2 receptor | 2.51 | 0.0210165 |
| MLF1 interacting protein | 2.51 | 0.0177203 |
| heat shock 70 kDa protein 2 | 2.50 | 0.0215102 |
| hairy and enhancer of split 1, (*Drosophila*) | 2.50 | 0.000283509 |
| ATP-binding cassette, sub-family C (CFTR | 2.49 | 0.00382491 |
| serglycin | 2.48 | 0.0443487 |
| sema domain, immunoglobulin domain (Ig), short basic doma | 2.47 | 0.008548 |
| ankyrin repeat domain 1 (cardiac muscle) | 2.47 | 0.00911953 |
| transporter 1, ATP-binding cassette, sub-family B (MDR | 2.47 | 0.00859077 |
| transporter 1, ATP-binding cassette, sub-family B (MDR | 2.47 | 0.00859077 |
| transporter 1, ATP-binding cassette, sub-family B (MDR | 2.47 | 0.00859077 |
| histone cluster 1, H1b | 2.46 | 0.0470898 |
| family with sequence similarity 72, member A | 2.46 | 0.00165234 |
| membrane bound O-acyltransferase domain containing 1 | 2.46 | 0.01185 |
| epidermal growth factor receptor pathway substrate 8 | 2.45 | 0.0194949 |
| ASF1 anti-silencing function 1 homolog B (*S. cerevisiae*) | 2.45 | 0.00543408 |
| dedicator of cytokinesis 11 | 2.44 | 0.00697577 |
| family with sequence similarity 72, member A | 2.44 | 0.00162905 |
| actin related protein 2 | 2.44 | 0.000288443 |
| CTP synthase | 2.43 | 8.80E−05 |
| M-phase phosphoprotein 1 | 2.43 | 0.0271814 |
| CDC28 protein kinase regulatory subunit 1B | 2.43 | 0.0145263 |
| histone cluster 1, H2ai | 2.43 | 0.0161621 |
| high-mobility group nucleosomal binding domain 2 | 2.42 | 0.0030536 |
| heat shock 70 kDa protein 1A | 2.42 | 0.00734287 |
| heat shock 70 kDa protein 1A | 2.42 | 0.00674816 |
| carnitine palmitoyltransferase 1A (liver) | 2.41 | 0.00170894 |
| neurofilament, medium polypeptide 150 kDa | 2.41 | 0.0190611 |
| transmembrane protein 62 | 2.41 | 0.00761064 |
| vaccinia related kinase 1 | 2.40 | 0.0233182 |
| geminin, DNA replication inhibitor | 2.40 | 0.00167629 |
| phosphoglucomutase 2 | 2.40 | 0.00818204 |
| lamin B1 | 2.40 | 0.0477748 |
| keratin 18 | 2.40 | 0.000112551 |
| deafness, autosomal dominant 5 | 2.39 | 0.00235481 |
| proteasome (prosome, macropain) subunit, beta type, 9 (lar | 2.39 | 0.0202595 |
| proteasome (prosome, macropain) subunit, beta type, 9 (lar | 2.39 | 0.0202595 |
| proteasome (prosome, macropain) subunit, beta type, 9 (lar | 2.39 | 0.0202595 |
| chromosome 12 open reading frame 31 | 2.39 | 0.0173089 |
| isocitrate dehydrogenase 3 (NAD+) alpha | 2.39 | 0.00297129 |
| forkhead box M1 | 2.38 | 0.0203154 |
| transmembrane protein 106C | 2.38 | 0.000214223 |
| hypothetical protein LOC729012 | 2.38 | 0.000446087 |
| PHD finger protein 1 | 2.37 | 0.010191 |
| mitochondrial ribosomal protein L15 | 2.37 | 0.0306092 |
| elastin microfibril interfacer 2 | 2.37 | 0.0192072 |
| hypothetical protein DKFZp762E1312 | 2.37 | 0.00726778 |
| retinoblastoma-like 1 (p107) | 2.36 | 0.00319946 |
| tissue factor pathway inhibitor (lipoprotein-associated | 2.36 | 0.0356227 |
| epithelial cell transforming sequence 2 oncogene | 2.36 | 0.000571152 |
| crystallin, zeta (quinone reductase) | 2.36 | 0.0370884 |
| hect domain and RLD 4 | 2.36 | 0.00679184 |
| high-mobility group nucleosomal binding domain 2 | 2.36 | 0.00384071 |
| cell division cycle 25 homolog A (*S. pombe*) | 2.36 | 0.000341692 |
| thymopoietin | 2.35 | 0.0223176 |
| interferon-induced protein with tetratricopeptide repeats | 2.34 | 0.0177928 |
| Bloom syndrome | 2.34 | 0.0209259 |
| dual specificity phosphatase 1 | 2.34 | 0.00211272 |
| elongation factor, RNA polymerase II, 2 | 2.34 | 0.0130017 |
| small nuclear ribonucleoprotein D1 polypeptide 16 kDa | 2.34 | 0.0334665 |
| CDC45 cell division cycle 45-like (*S. cerevisiae*) | 2.33 | 0.00735977 |
| exonuclease 1 | 2.33 | 0.00739393 |
| ribosomal protein L39-like | 2.33 | 0.00429384 |

TABLE 8-continued

Gene expression in 2D adherent cells suitable for use according to the
present teachings compared to those expressed by PLX of WO/2007/108003

| Gene | 2D vs. Plurix (fold change) | p-value (treat) |
|---|---|---|
| histone cluster 1, H2bh | 2.33 | 0.0377748 |
| ribonucleotide reductase M1 polypeptide | 2.33 | 0.000170076 |
| sulfiredoxin 1 homolog (S. cerevisiae) | 2.32 | 5.14E−05 |
| multiple coagulation factor deficiency 2 | 2.31 | 0.0116892 |
| proteasome (prosome, macropain) subunit, alpha type, 3 | 2.31 | 0.0195874 |
| ribonuclease H2, subunit A | 2.30 | 0.00669936 |
| minichromosome maintenance complex component 10 | 2.29 | 0.0037925 |
| heat shock 70 kDa protein 1B | 2.28 | 0.0048959 |
| heat shock 70 kDa protein 1B | 2.28 | 0.0054404 |
| heat shock 70 kDa protein 1B | 2.28 | 0.0054404 |
| ATPase, Na+ | 2.28 | 0.000381464 |
| hypothetical protein LOC201725 | 2.28 | 0.000313319 |
| cathepsin L1 | 2.27 | 0.0314419 |
| cell division cycle associated 5 | 2.27 | 0.01021 |
| RAB8B, member RAS oncogene family | 2.27 | 0.00417066 |
| SPC24, NDC80 kinetochore complex component, homolog (S. ce | 2.27 | 0.00287227 |
| gamma-glutamyl hydrolase (conjugase, folylpolygammaglutamyl | 2.26 | 0.0195219 |
| cell division cycle 25 homolog C (S. pombe) | 2.25 | 0.0169914 |
| mutS homolog 2, colon cancer, nonpolyposis type 1 (E. coli) | 2.25 | 0.00578953 |
| metallothionein 1L (gene | 2.25 | 0.00709646 |
| RRS1 ribosome biogenesis regulator homolog (S. cerevisiae) | 2.24 | 0.0120061 |
| cell division cycle associated 8 | 2.24 | 0.00619878 |
| shugoshin-like 2 (S. pombe) | 2.24 | 0.000852557 |
| mRNA turnover 4 homolog (S. cerevisiae) | 2.24 | 0.00373104 |
| ST6 (alpha-N-acetyl-neuraminyl-2,3-beta-galactosyl-1, | 2.24 | 0.00830766 |
| v-ets erythroblastosis virus E26 oncogene homolog 2 (avian) | 2.23 | 0.0364123 |
| replication factor C (activator 1) 2, 40 kDa | 2.23 | 0.00768959 |
| NIMA (never in mitosis gene a)-related kinase 7 | 2.23 | 0.00159114 |
| basic leucine zipper and W2 domains 2 | 2.23 | 0.0190782 |
| histone cluster 1, H2bf | 2.23 | 0.0124279 |
| eukaryotic translation initiation factor 1A, X-linked | 2.23 | 0.00330183 |
| transporter 1, ATP-binding cassette, sub-family B (MDR | 2.22 | 0.0164234 |
| transporter 1, ATP-binding cassette, sub-family B (MDR | 2.22 | 0.0164234 |
| transporter 1, ATP-binding cassette, sub-family B (MDR | 2.22 | 0.0164234 |
| polymerase (RNA) III (DNA directed) polypeptide G (32 kD) | 2.22 | 0.0298794 |
| phosphatidylinositol-4-phosphate 5-kinase, type II, alph | 2.22 | 0.00964099 |
| proteasome (prosome, macropain) 26S subunit, ATPase, 6 | 2.22 | 0.024269 |
| pituitary tumor-transforming 1 | 2.21 | 0.0485166 |
| histone cluster 2, H3d | 2.21 | 0.0102932 |
| sulfide quinone reductase-like (yeast) | 2.21 | 0.0473641 |
| serglycin | 2.20 | 0.00880325 |
| ribosomal protein L22-like 1 | 2.20 | 0.00335381 |
| membrane protein, palmitoylated 1, 55 kDa | 2.20 | 0.000396285 |
| solute carrier family 24 (sodium | 2.20 | 0.0328774 |
| STAM binding protein-like 1 | 2.20 | 0.0181743 |
| WD repeat and HMG-box DNA binding protein 1 | 2.20 | 0.0034833 |
| CSE1 chromosome segregation 1-like (yeast) | 2.20 | 0.0013662 |
| origin recognition complex, subunit 6 like (yeast) | 2.20 | 0.00182466 |
| transcription factor A, mitochondrial | 2.19 | 0.0110092 |
| exosome component 8 | 2.19 | 0.00132017 |
| mitochondrial ribosomal protein L1 | 2.19 | 0.0361058 |
| sphingomyelin synthase 2 | 2.19 | 0.0020701 |
| deoxycytidine kinase | 2.18 | 0.00101444 |
| family with sequence similarity 29, member A | 2.18 | 0.00469407 |
| chromosome 6 open reading frame 167 | 2.18 | 0.0011095 |
| dual specificity phosphatase 11 (RNA | 2.18 | 0.00426788 |
| F-box protein 45 | 2.18 | 0.00510098 |
| ras-related C3 botulinum toxin substrate 2 (rho family, sma | 2.17 | 0.0292466 |
| FK506 binding protein 5 | 2.17 | 0.0193805 |
| breast cancer 1, early onset | 2.17 | 0.0180553 |
| nuclear factor I | 2.17 | 0.0010313 |
| thioredoxin | 2.17 | 0.009636 |
| SH2 domain containing 4A | 2.16 | 0.0323646 |
| TGF beta-inducible nuclear protein 1 | 2.16 | 0.00285964 |
| PSMC3 interacting protein | 2.16 | 0.00766442 |
| chromosome 3 open reading frame 14 | 2.15 | 0.0377617 |
| polycomb group ring finger 5 | 2.15 | 0.000294142 |
| centrosomal protein 27 kDa | 2.15 | 0.00931602 |
| family with sequence similarity 64, member A | 2.14 | 0.0019785 |

TABLE 8-continued

Gene expression in 2D adherent cells suitable for use according to the present teachings compared to those expressed by PLX of WO/2007/108003

| Gene | 2D vs. Plurix (fold change) | p-value (treat) |
|---|---|---|
| acidic (leucine-rich) nuclear phosphoprotein 32 family, m | 2.14 | 0.0300263 |
| sterol O-acyltransferase (acyl-Coenzyme A: cholesterol acy | 2.14 | 0.0193637 |
| TATA box binding protein (TBP)-associated factor, RNA poly | 2.13 | 0.00514451 |
| origin recognition complex, subunit 5-like (yeast) | 2.13 | 0.049697 |
| Rac GTPase activating protein 1 pseudogene | 2.13 | 0.000269488 |
| LSM5 homolog, U6 small nuclear RNA associated (*S. cerevisia*) | 2.13 | 0.00264664 |
| minichromosome maintenance complex component 7 | 2.13 | 0.0457691 |
| met proto-oncogene (hepatocyte growth factor receptor) | 2.13 | 0.0318147 |
| tripartite motif-containing 25 | 2.13 | 0.0456344 |
| chromosome 13 open reading frame 34 | 2.13 | 0.000702936 |
| patatin-like phospholipase domain containing 4 | 2.13 | 0.0168306 |
| minichromosome maintenance complex component 6 | 2.12 | 0.0161279 |
| intraflagellar transport 80 homolog (*Chlamydomonas*) | 2.12 | 0.0247286 |
| peptidylprolyl isomerase F (cyclophilin F) | 2.12 | 0.00093846 |
| UTP15, U3 small nucleolar ribonucleoprotein, homolog (*S. c*) | 2.12 | 0.00482559 |
| TAF9B RNA polymerase II, TATA box binding protein (TBP)-as | 2.12 | 0.0170365 |
| TAF9B RNA polymerase II, TATA box binding protein (TBP)-as | 2.12 | 0.0170365 |
| esotropic viral integration site 2B | 2.12 | 0.0171408 |
| 3'-phosphoadenosine 5'-phosphosulfate synthase 2 | 2.12 | 1.43E−05 |
| proteasome (prosome, macropain) activator subunit 2 (PA28 | 2.12 | 0.00609885 |
| ADAM metallopeptidase with thrombospondin type 1 motif, | 2.12 | 0.0102751 |
| flap structure-specific endonuclease 1 | 2.12 | 0.006882 |
| S100 calcium binding protein A3 | 2.12 | 0.0324073 |
| RAD18 homolog (*S. cerevisiae*) | 2.11 | 0.0016685 |
| minichromosome maintenance complex component 3 | 2.11 | 0.0018389 |
| exosome component 3 | 2.11 | 0.0249115 |
| cysteinyl-tRNA synthetase 2, mitochondrial (putative) | 2.11 | 0.00564558 |
| glutamate-cysteine ligase, modifier subunit | 2.11 | 0.00378868 |
| brix domain containing 1 | 2.11 | 0.00981178 |
| kinesin family member 22 | 2.11 | 0.0192406 |
| UTP11-like, U3 small nucleolar ribonucleoprotein, (yeast) | 2.10 | 0.0132794 |
| v-ral simian leukemia viral oncogene homolog B (ras related | 2.10 | 0.012225 |
| meiotic nuclear divisions 1 homolog (*S. cerevisiae*) | 2.10 | 0.00164447 |
| phenylalanyl-tRNA synthetase, beta subunit | 2.10 | 0.000245973 |
| similar to Ubiquitin-conjugating enzyme E2S (Ubiqui | 2.10 | 0.000415822 |
| coiled-coil domain containing 68 | 2.10 | 0.00227586 |
| lamin B receptor | 2.10 | 0.000151784 |
| Niemann-Pick disease, type C1 | 2.10 | 0.0108117 |
| hydroxysteroid dehydrogenase like 2 | 2.09 | 3.71E−05 |
| RMI1, RecQ mediated genome instability 1, homolog (*S. cerev* | 2.09 | 0.00294705 |
| overexpressed in colon carcinoma-1 | 2.09 | 0.015322 |
| hypothetical protein FLJ20425 | 2.09 | 0.0174225 |
| primase, polypeptide 1, 49 kDa | 2.09 | 0.00801018 |
| chromosome 20 open reading frame 121 | 2.09 | 0.0146323 |
| microtubule associated serine | 2.08 | 0.00536974 |
| endothelial differentiation, sphingolipid G-protein-coupled | 2.08 | 0.0132848 |
| homeobox A9 | 2.08 | 0.00520942 |
| centromere protein L | 2.08 | 0.000880856 |
| nucleolar complex associated 3 homolog (*S. cerevisiae*) | 2.07 | 0.000373346 |
| fibroblast growth factor 7 (keratinocyte growth factor) | 2.07 | 0.0173208 |
| cysteine rich transmembrane BMP regulator 1 (chordin-like) | 2.07 | 0.0267286 |
| nucleoporin 155 kDa | 2.07 | 0.00218453 |
| FLJ20105 protein | 2.06 | 0.0127979 |
| CD44 molecule (Indian blood group) | 2.06 | 0.000651436 |
| polymerase (DNA directed), alpha 2 (70 kD subunit) | 2.06 | 0.0033903 |
| v-myb myeloblastosis viral oncogene homolog (avian)-like 2 | 2.06 | 0.00989416 |
| origin recognition complex, subunit 1-like (yeast) | 2.06 | 0.00207753 |
| hypothetical protein FLJ25416 | 2.06 | 0.000177531 |
| kinesin family member 22 | 2.06 | 0.0242075 |
| heat shock 60 kDa protein 1 (chaperonin) | 2.06 | 0.0327412 |
| minichromosome maintenance complex component 2 | 2.05 | 0.0021347 |
| fumarylacetoacetate hydrolase (fumarylacetoacetase) | 2.05 | 3.88E−05 |
| glycerol kinase 3 pseudogene | 2.05 | 0.0103203 |
| retinitis pigmentosa 2 (X-linked recessive) | 2.05 | 0.0264185 |

TABLE 8-continued

Gene expression in 2D adherent cells suitable for use according to the
present teachings compared to those expressed by PLX of WO/2007/108003

| Gene | 2D vs. Plurix (fold change) | p-value (treat) |
|---|---|---|
| U2AF homology motif (UHM) kinase 1 | 2.05 | 0.0255167 |
| chaperonin containing TCP1, subunit 5 (epsilon) | 2.04 | 0.00125909 |
| ATPase, H+ transporting, lysosomal 34 kDa, V1 subunit D | 2.04 | 0.0317453 |
| transcription termination factor, RNA polymerase II | 2.04 | 0.000393489 |
| succinate-CoA ligase, GDP-forming, beta subunit | 2.04 | 0.0028167 |
| cyclin-dependent kinase inhibitor 1B (p27, Kip1) | 2.04 | 0.00183021 |
| tyrosine 3-monooxygenase | 2.04 | 0.00021508 |
| cofactor required for Sp1 transcriptional activation, subu | 2.04 | 0.00141809 |
| glycosyltransferase 8 domain containing 3 | 2.03 | 0.022868 |
| ribosomal RNA processing 15 homolog (*S. cerevisiae*) | 2.03 | 0.0274884 |
| glycogenin 1 | 2.03 | 0.0224317 |
| hypothetical protein FLJ40869 | 2.03 | 0.00444509 |
| proliferating cell nuclear antigen | 2.03 | 0.0031727 |
| sterile alpha motif domain containing 12 | 2.03 | 0.0232188 |
| chromosome 16 open reading frame 59 | 2.03 | 0.00185191 |
| cofilin 2 (muscle) | 2.03 | 0.0459235 |
| eukaryotic translation initiation factor 2, subunit 2 bet | 2.03 | 0.0139947 |
| chromatin assembly factor 1, subunit B (p60) | 2.03 | 0.0119687 |
| Zwilch, kinetochore associated, homolog (*Drosophila*) | 2.02 | 0.000725107 |
| ATP-binding cassette, sub-family E (OABP), member 1 | 2.02 | 0.00454751 |
| LSM3 homolog, U6 small nuclear RNA associated (*S. cerevisia* | 2.02 | 0.0199824 |
| IQ motif containing GTPase activating protein 3 | 2.02 | 0.0495882 |
| tubulin, alpha 1c | 2.02 | 0.00862586 |
| DBF4 homolog (*S. cerevisiae*) | 2.01 | 0.0458795 |
| amyloid beta precursor protein binding protein 1 | 2.01 | 0.000910538 |
| suppressor of variegation 3-9 homolog 1 (*Drosophila*) | 2.01 | 0.00224324 |
| THO complex 7 homolog (*Drosophila*) | 2.01 | 0.0047251 |
| amyotrophic lateral sclerosis 2 (juvenile) chromosome re | 2.01 | 0.0484466 |
| nucleoporin 37 kDa | 2.01 | 0.00652747 |
| nucleolar protein 11 | 2.01 | 0.000852662 |
| ATP synthase, H+ transporting, mitochondrial F0 complex | 2.01 | 0.00866627 |
| histone cluster 1, H2ai | 2.01 | 0.0129155 |
| phytoceramidase, alkaline | 2.01 | 0.0157729 |
| primase, polypeptide 2A, 58 kDa | 2.01 | 0.00290097 |
| similar to High mobility group protein B1 (High mobili | 2.00 | 0.000363158 |
| mastermind-like 3 (*Drosophila*) | −2.00 | 0.00386667 |
| UDP-N-acetyl-alpha-D-galactosamine:polypeptide N-acetylga | −2.01 | 0.0268634 |
| ring finger protein 122 | −2.01 | 0.0236621 |
| chromodomain helicase DNA binding protein 3 | −2.01 | 6.39E−05 |
| centaurin, gamma-like family, member 10 pseudogene | −2.01 | 8.70E−05 |
| chromosome 7 open reading frame 10 | −2.01 | 0.00738442 |
| chromosome 6 open reading frame 111 | −2.01 | 0.0104492 |
| centaurin, gamma-like family, member 10 pseudogene | −2.01 | 0.000334818 |
| Prader-Willi syndrome chromosome region 1 | −2.01 | 0.0415526 |
| KIAA1245 | −2.01 | 0.0186309 |
| peroxidasin homolog (*Drosophila*) | −2.01 | 0.00219049 |
| melanoma antigen family D, 4 | −2.02 | 0.0263076 |
| melanoma antigen family D, 4 | −2.02 | 0.0263076 |
| glucosidase, alpha; acid (Pompe disease, glycogen storage di | −2.02 | 0.000418401 |
| phospholipase A2 receptor 1, 180 kDa | −2.03 | 0.00069343 |
| glycosyltransferase 8 domain containing 2 | −2.03 | 0.0173546 |
| KIAA1546 | −2.03 | 0.000255634 |
| protocadherin beta 9 | −2.03 | 0.0285124 |
| TBC1 domain family, member 3B | −2.03 | 0.000414974 |
| sushi, nidogen and EGF-like domains 1 | −2.03 | 0.00161129 |
| microtubule-actin crosslinking factor 1 | −2.04 | 0.00216 |
| region containing neuroblastoma breakpoint family, | −2.04 | 0.0213393 |
| golgi autoantigen, golgin subfamily a-like pseudogene | −2.04 | 0.0182674 |
| transducin-like enhancer of split 4 (E(sp1) homolog, *Drosop* | −2.04 | 0.0164153 |
| solute carrier family 22 (organic cation transporter), | −2.05 | 0.0137275 |
| neighbor of Punc E11 | −2.05 | 0.0184739 |
| insulin-like growth factor binding protein 5 | −2.05 | 0.011614 |
| KIAA1245 | −2.06 | 0.0185376 |
| vitamin D (1,25-dihydroxyvitamin D3) receptor | −2.06 | 0.000192208 |
| B-cell CLL | −2.06 | 0.00343507 |
| KIAA1305 | −2.06 | 0.00813727 |
| KIAA1245 | −2.06 | 0.0185609 |
| centaurin, gamma-like family, member 10 pseudogene | −2.07 | 3.08E−05 |
| TBC1 domain family, member 3B | −2.07 | 0.00141297 |
| similar to TBC1 domain family member 3 (Rab GTPase- | −2.08 | 0.00105098 |
| mannosidase, alpha, class 2B, member 1 | −2.08 | 0.000353303 |

TABLE 8-continued

Gene expression in 2D adherent cells suitable for use according to the present teachings compared to those expressed by PLX of WO/2007/108003

| Gene | 2D vs. Plurix (fold change) | p-value (treat) |
|---|---|---|
| cysteine-rich PAK1 inhibitor | −2.08 | 0.000125336 |
| midline 1 (Opitz | −2.08 | 0.00130803 |
| small nucleolar RNA, H | −2.09 | 0.017124 |
| urocortin 2 | −2.09 | 0.00172263 |
| neuroblastoma breakpoint family, member 11 | −2.09 | 0.0138065 |
| collagen, type VI, alpha 3 | −2.09 | 2.09E−06 |
| neuroblastoma breakpoint family, member 11 | −2.09 | 0.0148372 |
| hypothetical protein LOC646870 | −2.09 | 0.0117625 |
| calsyntenin 3 | −2.09 | 0.00300887 |
| cortactin binding protein 2 | −2.09 | 2.28E−05 |
| synaptic vesicle glycoprotein 2A | −2.10 | 0.00704212 |
| similar to Dynamin-1 (D100) (Dynamin, brain) (B-dyn | −2.10 | 0.0190733 |
| similar to Dynamin-1 (D100) (Dynamin, brain) (B-dyn | −2.10 | 0.0190733 |
| similar to TBC1 domain family member 3 (Rab GTPase- | −2.10 | 0.00108467 |
| Notch homolog 2 (*Drosophila*) N-terminal like | −2.10 | 0.0193058 |
| matrix-remodelling associated 5 | −2.11 | 0.000317637 |
| complement component 1, s subcomponent | −2.11 | 0.0395863 |
| cysteine sulfinic acid decarboxylase | −2.11 | 0.00428211 |
| hypothetical protein FLJ36144 | −2.11 | 0.00958437 |
| hypothetical protein FLJ36144 | −2.11 | 0.00958437 |
| dihydropyrimidinase-like 3 | −2.12 | 0.0165203 |
| procollagen C-endopeptidase enhancer | −2.12 | 0.0039236 |
| golgi autoantigen, golgin subfamily a-like pseudogene | −2.12 | 0.00720508 |
| TBC1 domain family, member 3B | −2.12 | 0.00122924 |
| collagen, type VII, alpha 1 (epidermolysis bullosa, dystr | −2.13 | 0.00109233 |
| versican | −2.14 | 0.023885 |
| mannose receptor, C type 2 | −2.14 | 0.00012142 |
| golgi autoantigen, golgin subfamily a-like pseudogene | −2.14 | 0.00767095 |
| dynamin 1 | −2.15 | 0.00139674 |
| TBC1 domain family, member 3B | −2.16 | 0.00130459 |
| PHD finger protein 21A | −2.17 | 0.00980401 |
| centaurin, gamma-like family, member 10 pseudogene | −2.17 | 0.000180846 |
| slit homolog 3 (*Drosophila*) | −2.17 | 0.02844 |
| neuroepithelial cell transforming gene 1 | −2.18 | 0.0109689 |
| cyclin L2 | −2.18 | 0.00093459 |
| similar to dJ402H5.2 (novel protein similar to wo | −2.18 | 0.00621503 |
| phospholipase D family, member 3 | −2.18 | 1.17E−05 |
| collagen, type VIII, alpha 1 | −2.19 | 0.00187242 |
| cyclin L2 | −2.19 | 0.00109621 |
| protocadherin beta 14 | −2.20 | 0.0103892 |
| matrix metallopeptidase 2 (gelatinase A, 72 kDa gelatinase, | −2.20 | 5.59E−05 |
| lysyl oxidase-like 4 | −2.21 | 0.0120148 |
| golgi autoantigen, golgin subfamily a-like pseudogene | −2.21 | 0.00977719 |
| WW domain containing transcription regulator 1 | −2.21 | 0.0379899 |
| PDZ domain containing RING finger 3 | −2.21 | 0.00931014 |
| chromosome 14 open reading frame 37 | −2.21 | 0.0182453 |
| brain and acute leukemia, cytoplasmic | −2.22 | 0.0476919 |
| calcium channel, voltage-dependent, L type, alpha 1C sub | −2.22 | 0.0189661 |
| jun oncogene | −2.23 | 7.21E−05 |
| interleukin 19 | −2.23 | 0.0310328 |
| centaurin, gamma-like family, member 10 pseudogene | −2.23 | 0.000595086 |
| centaurin, gamma-like family, member 10 pseudogene | −2.23 | 0.000595086 |
| — | −2.24 | 0.00666187 |
| golgi autoantigen, golgin subfamily b, macrogolgin (with | −2.24 | 0.0164005 |
| chromosome 15 open reading frame 51 | −2.24 | 0.0123547 |
| similar to Dynamin-1 (D100) (Dynamin, brain) (B-dyn | −2.24 | 0.0123547 |
| similar to Dynamin-1 (D100) (Dynamin, brain) (B-dyn | −2.24 | 0.0123547 |
| AE binding protein 1 | −2.25 | 0.000105628 |
| golgi autoantigen, golgin subfamily a-like pseudogene | −2.26 | 0.00770626 |
| transmembrane protein 16A | −2.27 | 0.0481085 |
| hypothetical LOC399844 | −2.27 | 0.000491694 |
| oculomedin | −2.27 | 0.00778869 |
| low density lipoprotein-related protein 1 (alpha-2-macroglo | −2.28 | 4.26E−05 |
| fibronectin leucine rich transmembrane protein 2 | −2.28 | 0.0135122 |
| phospholipid transfer protein | −2.29 | 0.00999206 |
| similar to Dynamin-1 (D100) (Dynamin, brain) (B-dyn | −2.29 | 0.0122573 |
| SATB homeobox 2 | −2.31 | 0.039781 |
| similar to TBC1 domain family member 3 (Rab GTPase- | −2.32 | 0.000870285 |
| tweety homolog 1 (*Drosophila*) | −2.32 | 0.00450824 |
| CD24 molecule | −2.34 | 0.0340122 |
| chimerin (chimaerin) 1 | −2.35 | 0.0287031 |
| AHA1, activator of heat shock 90 kDa protein ATPase homolog | −2.37 | 0.00979472 |

TABLE 8-continued

Gene expression in 2D adherent cells suitable for use according to the
present teachings compared to those expressed by PLX of WO/2007/108003

| Gene | 2D vs. Plurix (fold change) | p-value (treat) |
|---|---|---|
| bicaudal C homolog 1 (*Drosophila*) | −2.38 | 0.0347162 |
| solute carrier family 6 (neurotransmitter transporter, ta | −2.38 | 0.00729635 |
| milk fat globule-EGF factor 8 protein | −2.39 | 0.000987073 |
| WNK lysine deficient protein kinase 1 | −2.40 | 1.57E−05 |
| small nucleolar RNA, H | −2.41 | 0.00843141 |
| tweety homolog 3 (*Drosophila*) | −2.42 | 0.000165552 |
| SH3 and PX domains 2B | −2.42 | 0.0244357 |
| WD repeat and SOCS box-containing 1 | −2.44 | 0.0387851 |
| hypothetical protein PRO2012 | −2.45 | 0.00756704 |
| golgi autoantigen, golgin subfamily a-like pseudogene | −2.46 | 0.00320764 |
| microfibrillar-associated protein 2 | −2.47 | 0.0152901 |
| collagen, type XII, alpha 1 | −2.47 | 0.000204664 |
| ST6 beta-galactosamide alpha-2,6-sialyltranferase 2 | −2.47 | 0.0216987 |
| thioredoxin interacting protein | −2.48 | 0.0135494 |
| latent transforming growth factor beta binding protein 2 | −2.49 | 4.08E−05 |
| golgi autoantigen, golgin subfamily a-like pseudogene | −2.49 | 0.00603583 |
| formin binding protein 1-like | −2.50 | 0.00290401 |
| maternally expressed 3 | −2.52 | 0.0112259 |
| PTK7 protein tyrosine kinase 7 | −2.54 | 0.000116114 |
| ribonuclease P RNA component H1 | −2.57 | 0.0156126 |
| sushi-repeat-containing protein, X-linked 2 | −2.58 | 0.0253856 |
| sortilin-related VPS10 domain containing receptor 2 | −2.58 | 0.00936311 |
| similar to RIKEN cDNA 1110018M03 | −2.59 | 0.00516476 |
| pyridoxal-dependent decarboxylase domain containing 2 | −2.60 | 0.00683647 |
| Enah | −2.61 | 0.0077547 |
| asporin | −2.62 | 0.000659873 |
| small Cajal body-specific RNA 17 | −2.63 | 0.0301336 |
| nuclear pore complex interacting protein | −2.67 | 0.00988632 |
| sushi, von Willebrand factor type A, EGF and pentraxin dom | −2.69 | 2.23E−05 |
| protein tyrosine phosphatase, receptor type, U | −2.69 | 0.0270428 |
| collagen, type V, alpha 1 | −2.70 | 0.0166427 |
| nuclear pore complex interacting protein | −2.73 | 0.0018339 |
| transformer-2 alpha | −2.74 | 0.012256 |
| dystrophin related protein 2 | −2.79 | 0.0137557 |
| golgi autoantigen, golgin subfamily a, 8A | −2.80 | 0.0111179 |
| collagen, type VI, alpha 2 | −2.81 | 0.0149554 |
| transforming growth factor, beta 3 | −2.81 | 0.0287865 |
| trophinin | −2.82 | 0.00298044 |
| hypothetical protein MGC24103 | −2.86 | 0.0346673 |
| supervillin | −2.87 | 0.0412717 |
| ADAM metallopeptidase with thrombospondin type 1 motif, | −2.90 | 0.0113968 |
| kinesin family member 26B | −2.91 | 0.00363199 |
| nuclear pore complex interacting protein | −2.91 | 0.00160273 |
| trichorhinophalangeal syndrome I | −2.94 | 0.00557712 |
| nuclear pore complex interacting protein | −2.96 | 0.00111223 |
| small nucleolar RNA, C | −2.96 | 0.00666866 |
| homeobox A2 | −2.97 | 0.0435423 |
| distal-less homeobox 5 | −3.00 | 0.000640157 |
| dachsous 1 (*Drosophila*) | −3.00 | 0.00697244 |
| small nucleolar RNA, C | −3.06 | 0.0274043 |
| small nucleolar RNA, C | −3.06 | 0.0274043 |
| nuclear pore complex interacting protein | −3.09 | 0.00583397 |
| small nucleolar RNA, C | −3.14 | 0.0104491 |
| small nucleolar RNA, C | −3.14 | 0.0104491 |
| sushi-repeat-containing protein, X-linked | −3.16 | 0.00370941 |
| zinc finger protein 521 | −3.17 | 0.00668815 |
| nuclear pore complex interacting protein | −3.17 | 0.00117582 |
| chromosome 9 open reading frame 3 | −3.18 | 0.00410177 |
| golgi autoantigen, golgin subfamily a, 8B | −3.18 | 0.0121417 |
| hemicentin 1 | −3.21 | 0.0461603 |
| small nucleolar RNA, C | −3.24 | 0.00765575 |
| Kallmann syndrome 1 sequence | −3.25 | 0.000548703 |
| tenascin C (hexabrachion) | −3.26 | 8.26E−05 |
| nuclear pore complex interacting protein | −3.29 | 0.00282604 |
| nuclear pore complex interacting protein | −3.34 | 0.00263888 |
| homeobox B2 | −3.36 | 0.00665994 |
| similar to nuclear pore complex interacting protein | −3.41 | 0.0187322 |
| nuclear pore complex interacting protein | −3.46 | 0.00354416 |
| cholesterol 25-hydroxylase | −3.51 | 0.0445558 |
| ring finger protein 144 | −3.52 | 0.0135334 |
| nuclear pore complex interacting protein | −3.55 | 0.00316496 |
| calbindin 2, 29 kDa (calretinin) | −3.56 | 0.0290743 |

TABLE 8-continued

Gene expression in 2D adherent cells suitable for use according to the present teachings compared to those expressed by PLX of WO/2007/108003

| Gene | 2D vs. Plurix (fold change) | p-value (treat) |
|---|---|---|
| nuclear pore complex interacting protein | −3.58 | 0.00032839 |
| nuclear pore complex interacting protein | −3.60 | 0.000414309 |
| nuclear pore complex interacting protein | −3.62 | 0.00283418 |
| nuclear pore complex interacting protein | −3.64 | 0.000213956 |
| nuclear pore complex interacting protein | −3.66 | 0.000377834 |
| KIAA1641 | −3.69 | 0.0191782 |
| UDP-N-acetyl-alpha-D-galactosamine:polypeptide N-acetylga | −3.72 | 0.00964109 |
| nuclear pore complex interacting protein | −3.73 | 0.000352007 |
| leucine rich repeat containing 17 | −3.75 | 0.0263961 |
| chromosome 9 open reading frame 3 | −3.80 | 0.0233723 |
| nuclear pore complex interacting protein | −3.82 | 0.00368967 |
| neurotrimin | −3.87 | 3.78E−06 |
| protein tyrosine phosphatase, receptor type, N | −4.02 | 0.0294569 |
| KIAA1641 | −4.02 | 0.00659194 |
|  | −4.06 | 0.00488845 |
| KIAA1641 | −4.16 | 0.0170531 |
| integrin, alpha 11 | −4.16 | 0.000390317 |
| KIAA1641 | −4.27 | 0.013175 |
| odz, odd Oz | −4.28 | 0.00172671 |
| transmembrane protein 119 | −4.34 | 0.00801387 |
| plexin domain containing 2 | −4.44 | 0.031799 |
| ras homolog gene family, member J | −4.59 | 0.00197982 |
| homeobox B3 | −4.60 | 0.0354368 |
| similar to Protein KIAA0220 | −4.72 | 0.0302619 |
| raftlin family member 2 | −4.79 | 0.0260454 |
| WNT1 inducible signaling pathway protein 1 | −5.99 | 0.000672342 |
| clusterin | −6.40 | 0.0303973 |
| serpin peptidase inhibitor, clade F (alpha-2 antiplasmi | −6.47 | 0.00362941 |
| sulfatase 2 | −6.58 | 5.88E−05 |
| hephaestin | −6.74 | 0.0123141 |
| junctional adhesion molecule 2 | −7.33 | 0.0306758 |
| fibronectin type III domain containing 1 | −7.46 | 0.0334696 |
| sarcoglycan, delta (35 kDa dystrophin-associated glycoprotei | −7.69 | 0.000881984 |
| cystatin SN | −8.27 | 0.0496433 |
| microfibrillar-associated protein 4 | −8.67 | 0.00155578 |
| biglycan | −8.70 | 0.00161284 |
| transmembrane, prostate androgen induced RNA | −10.54 | 0.000100935 |
| carboxypeptidase E | −12.48 | 0.00738131 |

Figure 2:
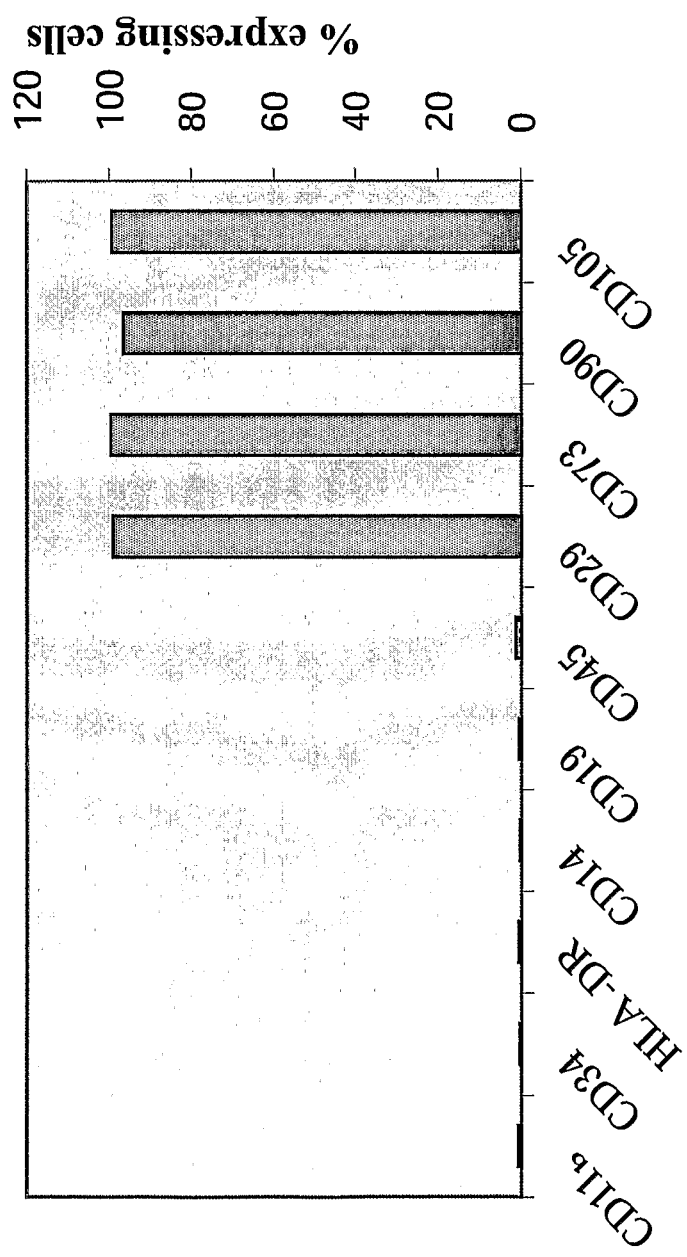
FIG. 2 is a bar graph depicting marker expression on 2D adherent cells of placenta suitable for use in accordance with the present teachings. Of note, negative expression was recorded for CD11b, CD34, HLA-DR, CD14, CD19 and CD45, while positive expression was noted for CD29, CD73, CD90 and CD105.

Characterization of membrane markers on 2D adherent cells suitable for use according to the present teachings—the surface antigens expressed by 2D adherent cells were examined using monoclonal antibodies. These cells were stable adhesive cells that were expanded in vitro without the loss of phenotype and without showing signs of karyotypic changes. Flow cytometric analysis of 2D adherent cells' membrane markers showed a high incidence of cells expressing CD105, CD73, CD90 and CD29. Furthermore, a high incidence of cells was lacking the expression of CD45, CD34 and CD19, CD11b, CD14 and HLA-DR surface markers (FIG. 2).

Figure 3:
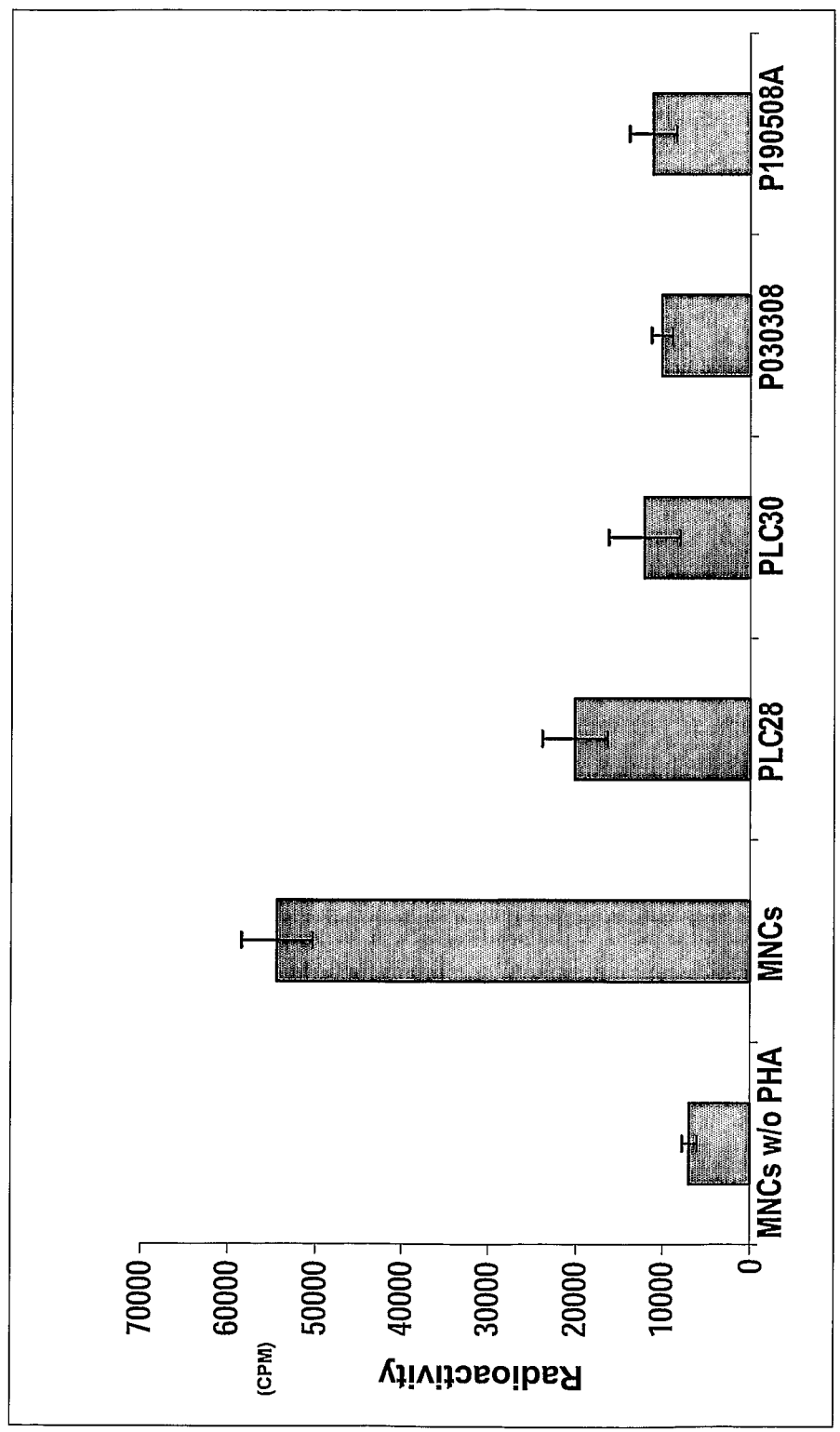
FIG. 3 is a bar graph depicting reduction of lymphocyte cell response by 2D adherent cells of placenta suitable for use in accordance with the present teachings. Peripheral blood (PB) derived mononuclear cells (MNCs) were stimulated with PHA (10 μg/ml). One of four different batches of 2D adherent cells were added to the stimulated MNCs. Three replicates of each group were seeded in 96-well plates.

Immunomodulation by 2D adherent cells—The immunogenicity of the 2D adherent cells was investigated next. As shown in FIG. 3, four different batches of 2D adherent cells were capable of reducing lymphocyte proliferation, following mitogenic stimuli with Phytohemagglutinin (PHA), as was measured by Thymidine incorporation.

Figure 4C:
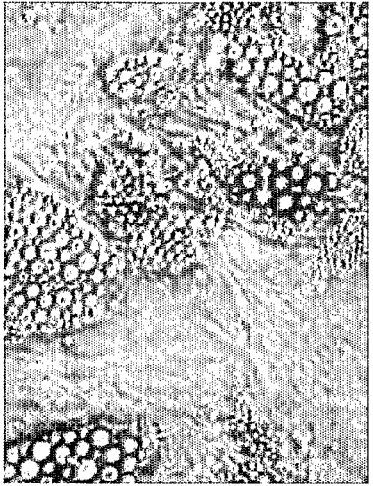
FIGS. 4A-F are photographs depicting growth of bone marrow and placenta cells under osteogenesis or adipogenesis differentiation conditions. Bone marrow derived cells (FIGS. 4A-C) or placenta derived cells (FIGS. 4D-F) were plated in growth medium (FIGS. 4A and 4D), osteogenesis differentiation medium (FIGS. 4B and 4E) or adipogenesis differentiation medium (FIGS. 4C and 4F) in a 24 well plate coated with vitronectin and collagen. Medium was replaced every 3-4 days. At the end of growth period cells were fixed, stained and pictured as described in detail the Examples section which follows.
Figure 4B:
Figure 4A:

Osteocyte induction—osteocyte differentiation of placenta- or bone marrow-derived adherent cells in osteogenic induction medium resulted in differentiation of over 50% of the bone marrow cells, as demonstrated by positive alizarin red staining (FIG. 4B). On the contrary, none of the placental derived cells showed any signs of osteogenic differentiation (see FIGS. 4B and 4E and Table 9, below).

TABLE 9

Differentiation summary

|  | BM 108 + BM109 | PLC-11-3-1 | PLC-8-2-1 | Plc-15-3-4-2 | Plc 4-3-1 |
|---|---|---|---|---|---|
| Osteocytes | +++ | − | − | − | − |
| Adipocytes | +++ | − | − | − | − |

Figure 5C:
FIGS. 5A-F are photographs depicting growth of bone marrow and placenta cells under modified osteogenesis or adipogenesis differentiation conditions. Bone marrow derived cells (FIGS. 5A-C) or placenta derived cells (FIGS. 5D-F) were plated in growth medium (FIGS. 5A and 5D), osteogenesis differentiation medium (FIGS. 5B and 5E) or adipogenesis differentiation medium (FIGS. 5C and 5F) in a 24 well plate coated with vitronectin and collagen. Medium was replaced every 3-4 days. At the end of growth period cells were fixed, stained and pictured as described in detail the Examples section which follows.
Figure 5B:
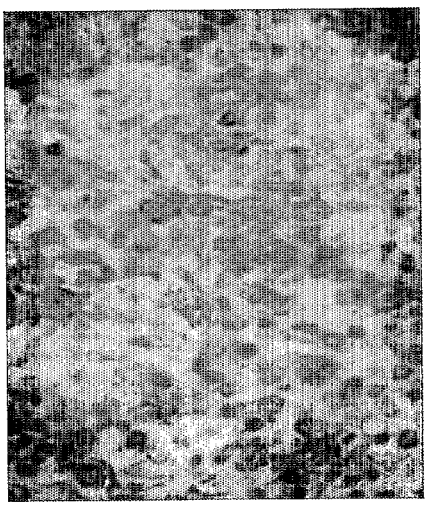
Figure 5A:
Figure 5F:
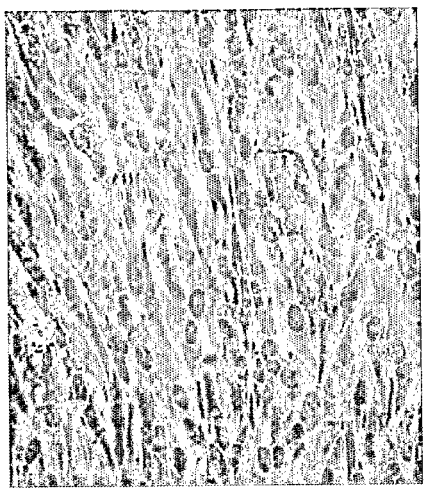
Figure 5E:
Figure 5D:
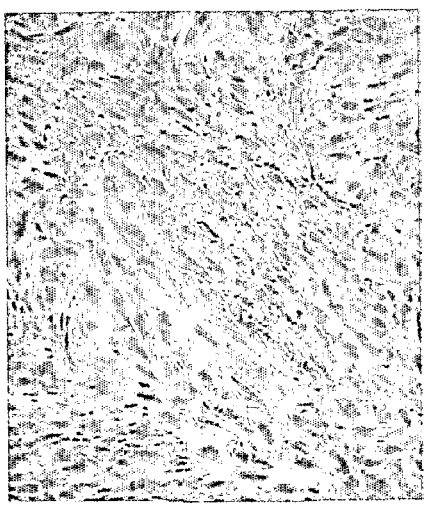

Next, 2D adherent cells from bone marrow or placenta origin were stimulated to differentiate in a modified osteogenic medium comprising Vitamin D and higher concentrations of dexamethasone, a modification of the osteogenic differentiation protocol according to previous teachings [Parloni et al. (2008) Stem Cells 26(2): 300-11]. As evident from the results, over 50% of the bone marrow cells underwent differentiation into osteocytes, as demonstrated by positive alizarin red staining (see FIG. 5B). However, none of the placental derived cells showed any signs of osteogenic differentiation (see FIG. 5E and Table 9, hereinabove).

Adipocyte induction—adipocyte differentiation of placenta- or bone marrow-derived 2D adherent cells in adipocyte induction medium resulted in differentiation of over 50% of the bone marrow derived cells (see FIG. 4C), as demonstrated by positive oil red staining and by typical morphological changes (e.g. accumulation of oil droplets in the cytoplasm).

Figure 4F:
Figure 4E:
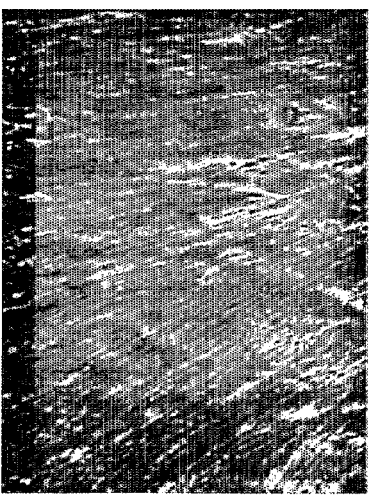
Figure 4D:
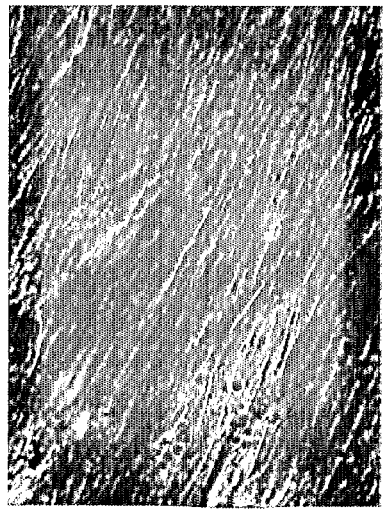

In contrast, none of the placental derived cells differentiated into adipocytes (see FIG. 4F and Table 9, hereinabove).

Next, 2D adherent cells from bone marrow or placenta origin were stimulated to differentiate into adipocytes in a modified medium comprising a higher level of Indomethacine, a modification of the adipocyte differentiation protocol according to previous teachings [Parloni et al. (2007), supra]. As evident from the results, over 50% of the bone marrow derived cells underwent differentiation into adipocytes (see FIG. 5C), as demonstrated by positive oil red staining and by typical morphological changes (e.g. accumulation of oil droplets in the cytoplasm). In contrast, none of the placental derived cells exhibited morphological changes typical of adipocytes (see FIG. 5F and Table 9, hereinabove).

Example 3

Methods of Generating 3D Adherent Cells Suitable for Use in Accordance with the Present Teachings and the 3D Adherent Cells Generated Thereby 3D adherent cells (PLX-C) were produced which exhibit different characteristics then the above described 3D adherent cells (PLX, Example 1).

Materials and Experimental Procedures

Celligen™ Plug Flow Bioreactor

The production of 3D adherent cells for use in accordance with the present invention by Celligen™ (PLX-C cells) was composed of several major steps. The process started by collection of a placenta from a planned cesarean delivery at term.

Adherent cells were then isolated from whole placentas, grown in tissue culture flasks (2D cultures), harvested and stored in liquid nitrogen as 2D-Cell Stock (2DCS), the appropriate amount of 2DCS were thawed, washed and seeded onto carriers in bioreactors for further expansion as 3D-culture. After 4-21 days of growth in the bioreactors, cells were harvested and cryopreserved in gas phase of liquid nitrogen as PLX-C.

Receipt of Human Tissue

All placentas obtained were received from the maternity ward under approval of the Helsinki Committee of the medical facility. Accordingly, all placenta donors signed an informed consent and Donor Screening and Donor Testing was performed (IPC1). Immediately after taking the placenta from the donor (during the caesarean procedure), it was placed in a sterile plastic bag and then in a Styrofoam box with ice packs. The placenta was delivered and immediately placed in a quarantine area until released to use by Quality Control (QC) and Quality Assurance (QA). All the following production steps were performed in a quarantine, clean room facility until QC approval of mycoplasma test results arrived and the cells were release for 2D cell growth.

Recovery and Processing of Adherent Cells

To initiate the process, the whole placenta tissue was cut into pieces under aseptic conditions under laminar flow hood, washed with Hank's buffer solution and incubated for 3 hours at 37° C. with 0.1% Collagenase (1 mg Collagenase/ml tissue). 2D cell medium (2D-Medium comprising DMEM supplemented with 10% FBS, fungizone 0.25 µg/ml and gentamycine 50 µg/ml) was added and the digested tissue was roughly filtered through a sterile metal strainer, collected in a sterile beaker and centrifuged (10 minutes, 1200 RPM, 4° C.). Using gentle pippeting, suspended cells were then washed with 2D-Medium supplemented with antibiotics, seeded in 80 cm$^2$ flasks and incubated at 37° C. in a tissue culture incubator under humidified condition supplemented with 5% $CO_2$. Following 2-3 days, in which the cells were allowed to adhere to the flask surface, they were washed with PBS and 2D-Medium was added.

Two Dimensional (2D) Cell Growth

Prior to the first passage, growth medium samples of 10% of the total flask number in quarantine was pooled and taken for mycoplasma testing (IPC2). If cells were found to be negative for Mycoplasma (EZ-PCR Mycoplasma kit, Biological Industries, Israel), cells were released from quarantine. After 1-2 additional passages, cells were transferred to the 2D production clean room (2DP). Once in Room 2DP, culture was continued for another 3-5 passages (of note, cells were grown in 2D-Medium supplemented with antibiotics until passage 3, thereafter cells were grown in 2D-Medium without antibiotics). IPC-3 sample was taken for immune phenotype after passage 4. Throughout the process, cultures were grown in a tissue culture incubator under humidified conditions with 5% CO2 at 37° C. After a total of 6-8 passages (9-16 cell doublings), cells were collected and cryopreserved as the 2D-Cell Stock (2DCS).

The first passage was usually carried out after 10-15 days. Beginning at passage 2 and continuing until passage 6-8, cells were passaged when the culture reached 70-80% confluence, usually after 3-5 days (1.5-2 doublings). The cells were detached from the flasks using 0.25% trypsin-EDTA (4 minutes at 37° C.) and seeded in a culture density of $3\pm0.2\times10^3$ cells/cm$^2$. The size of the tissue culture flasks raised as the passages proceed. The culturing process started in 80 cm$^2$ tissue culture flask, continued in 175 cm$^2$, then in 500 cm$^2$ (Triple flask) and finally the cells were seeded into Cell Factory 10 tray (6320 cm$^2$).

Prior to cryopreservation, at the end of 2DCS growth period, the growth medium was collected and the sample was prepared to be sent to an approved GLP laboratory for Mycoplasma test (IPC 4).

Cryopreservation Procedure for 2D-Cell-Stock Product

For 2DCS cryopreservation, 2D-cultured cells were collected under aseptic conditions using 0.25 trypsin-EDTA. The cells were centrifuged (1200 RPM, 10', 4° C.), counted and re-suspended in 2D-Medium.

For freezing, cell suspensions were diluted 1:1 with 2D-Freezing Mixture (final concentrations was 10% DMSO, 40% FBS and 50% 2D-Medium). Approximately $1.5-2.5\times10^9$ cells were manufactured from one placenta. 4 ml of the cells were stored at a final concentration of $10\times10^6$/ml in 5 ml cryopreservation polypropylene vials. The vials were labeled and transferred to a controlled rate freezer for a graduated temperature reducing process (1° C./min), after which they were transferred to storage in gas-phase of a liquid nitrogen freezer located in the Cold Storage Room. This material was referred to as the 2D-Cell Stock (2DCS) batch.

Initiation of the Three Dimensional (3D) Culture Procedures

To begin 3D culture, an appropriate amount ($150\pm30\times10^6$) of cells from 2DCS were thawed in the 2DP room and washed with 3D-Medium (DMEM with 10% FBS and 20 Mm Hepes) to remove DMSO prior to seeding in the prepared-in-advanced bioreactor systems. The content of each 2DCS vial was pipetted and diluted 1:9 with pre-warmed (37° C.) 3D-Medium. The cells were centrifuged (1200 RPM, 10', 4° C.) and re-suspended again in 50-100 ml pre-warmed (37° C.) 3D-Medium in a 250 ml sterile bottle. A sample was taken and cells were counted using a Trypan Blue stain in order to determine cell number and viability. The cell suspension was transferred under a laminar flow hood into a 0.5 L seeding bottle. From the seeding bottle the cell suspension was transferred via sterile tubing to the bioreactor by gravitation.

Production of Adherent Cells in the Celligen Bioreactor (PLX-C)

Bioreactor Description 3D growth phase was performed using an automatic CelliGen Plus® or BIOFLO 310 bioreactor system [(New Brunswick Scientific (NBS)]. The bioreactor system was used for cultivation of cell culture, in which conditions were suitable for high cell concentrations. The cultivation process was carried out using a bioreactor in a perfusion mode. The lab scale bioreactor was constructed of two main systems—the control system and the bioreactor itself (vessel and accessories). The parameters of the process were monitored and controlled by a control console which included connectors for probes, motor and pumps, control loops for Dissolved Oxygen (DO), pH, perfusion and agitation (with a motor), a gases control system, water circulation and heating system for temperature control and an operator interface. The controlled process parameters (such as temperature, pH, DO etc.) could be displayed on the operator interface and monitored by a designated controller.

Cell Culture Growth Procedure in the Bioreactors

As noted in the section hereinabove, $150\pm30\times10^6$ cells from the cryopreserved 2DCS were thawed, washed and seeded in a sterile bioreactor. The bioreactor contained 30-50 gr carriers (FibraCel® disks, NBS), made of Polyester and Polypropylene and 1.5±0.1 L 3D-Medium. The growth medium in the bioreactor was kept at the following conditions: 37° C., 70% Dissolved Oxygen (DO) and pH 7.3. Filtered gases (Air, $CO_2$, $N_2$ and $O_2$) were supplied as determined by the control system in order to keep the DO value at 70% and the pH value at 7.3. For the first 24 hours, the medium was agitated at 50 Rounds Per Minutes (RPM) and increased up to 200 RPM by day 2. For the first 2-3 days, the cells were grown in a batch mode. Perfusion was initiated when the medium glucose concentration decreased below 550 mg/liter. The medium was pumped from the feeding container to the bioreactor using sterile silicone tubing. All tubing connections were performed under laminar flow using sterile connectors. The perfusion was adjusted on a daily basis in order to keep the glucose concentration constant at approximately 550±50 mg/liter. A sample of the growth medium was taken every 1-2 days for glucose, lactate, glutamine, glutamate and ammonium concentration determination (BioProfile 400 analyzer, Nova Biomedical). The glucose consumption rate and the lactate formation rate of the cell culture enabled to measure cell growth rate. These parameters were used to determine the harvest time based on accumulated experimental data.

Harvest of the 3D Grown PLX-C Cells from the Bioreactor

The cell harvest process started at the end of the growth phase (4-10 days). Two samples of the growth medium were collected. One sample was prepared to be sent to an approved GLP laboratory for Mycoplasma testing according to USP and Eu standards, and the other one was transferred to a controlled rate freezer for a graduated temperature reducing process (1° C./min), after which they were transferred to storage in gas-phase of a liquid nitrogen freezer located in the Cold Storage Room, in case a repeat Mycoplasma testing was needed. These medium samples were considered as part of the Mycoplasma testing of the final product and the results were considered as part of the criteria for product release.

The 3D-grown culture was harvested in the Class-100 laminar area in room 3DP as follows:

The bioreactor vessel was emptied using gravitation via tubing to a waste container. The vessel was opened, by removing the head plate, and the carriers were aseptically transferred, using sterile forceps, from the basket to the upper basket net. The bioreactor vessel was then closed and refilled with 1.5 L pre-warmed PBS (37° C.). The agitation speed was increased to 150 RPM for 2 minutes. The PBS was drained via tubing by pressure or gravity to the waste bottle. The washing procedure was repeated twice.

In order to release the cells from the carriers, 1.5 L pre-warmed to 37° C. Trypsin-EDTA (Trypsin 0.25%, EDTA 1 mM) was added to the bioreactor vessel and carriers were agitated for 5 minutes in 150 RPM, 37° C. Cell suspension was collected to a 5 L sterile container containing 250 ml FBS. Cell suspension was divided to 4 500 ml sterile centrifuge tubes and a Mycoplasma test sample was withdrawn. Closed centrifuge tubes were transferred through the 3DP active pass-through into the class 10,000 filling room (FR1) in which the cells were aseptically filled and cryopreserved as PLX-C.

Cell Cycle Analysis

PLX-C cells obtained by Celligen and PLX cells obtained by Plurix were fixed with 70% EtOH O.N, centrifuged and re-suspended in a Propidium Iodide (PI) solution containing 2 μg/ml PI (Sigma), 0.2 mg/ml Rnase A (Sigma) and 0.1% (v/v) Triton (Sigma) for 30 minutes. Cell cycle was analyzed by FACS.

Gene Expression Array (Microarray)

Adherent cells were obtained from human full term placentas and were expanded Plurix or by Celligen. Three different batches of cells were obtained from each of the expansion methods for further examination.

RNA was extracted from the cells (Qiagen-Rneasy micro kit) and applied to an Affymetrix whole genome expression array. The chip used GeneChip® Human Exon 1.0 ST Array (Affymetrix, Santa Clara, Calif., USA).

FACS Analysis of Membrane Markers

Cells were stained with monoclonal antibodies as previously described. In short, 400,000-600,000 cells were suspended in 0.1 ml flow cytometer buffer in a 5 ml test tube and incubated for 15 minutes at room temperature (RT), in the dark, with each of the following monoclonal antibodies (MAbs): FITC-conjugated anti-human CD29 MAb (eBioscience), PE conjugated anti human CD73 MAb (Becton Dickinson), PE conjugated anti human CD105 MAb (eBioscience), PE conjugated anti human CD90 MAb (Becton Dickinson), FITC-conjugated anti-human CD45 MAb (IQProducts), PE-conjugated anti-human CD19 MAb (IQProducts), PE conjugated anti human CD14 MAb (IQProducts), FITC conjugated anti human HLA-DR MAb (IQProduct), PE conjugated anti human CD34 MAb (IQProducts), FITC conjugated anti human CD31 MAb (eBioscience), FITC conjugated anti human KDR MAb (R&D systems), anti human fibroblasts marker (D7-FIB) MAb(ACRIS), FITC-conjugated anti-human CD80 MAb (BD), FITC-conjugated anti-human CD86 MAb (BD), FITC-conjugated anti-human CD40 MAb (BD), FITC-conjugated anti-human HLA-ABC MAb (BD), Isotype IgG1 FITC conjugated (IQ Products), Isotype IgG1 PE conjugated (IQ Products).

Cells were washed twice with flow cytometer buffer, resuspended in 500 μl flow cytometer buffer and analyzed by flow cytometry using FC-500 Flow Cytometer (Beckman Coulter). Negative controls were prepared with relevant isotype fluorescence molecules.

Mixed Lymphocyte Reaction (MLR)

$2\times10^5$ peripheral blood (PB) derived MNC (from donor A) were stimulated with equal amount of irradiated (3000 Rad) PB derived MNCs (from donor B). Increasing amounts of PLX-Cs were added to the cultures. Three replicates of each group were seeded in 96-well plates. Cells were cultured in RPMI 1640 medium containing 20% FBS. Plates were pulsed with 1 µC $^3$H-thymidine during the last 18 hrs of the 5-day culturing. Cells were harvested over a fiberglass filter and thymidine uptake was quantified with scintillation counter.

For CFSE staining, PB-MNC cells were stained for CFSE (Molecular Probes) for proliferation measurement before culturing. Cells were collected after 5 days and the intensity of CFSE staining was detected by Flow Cytometry.

ELISA

ELISA was carried out as was previously described. In short, MNCs (isolated from peripheral blood) were stimulated with 5 µg/ml ConA (Sigma), 0.5 µg/ml LPS (SIGMA), or 10 µg/ml PHA (SIGMA) in the presence of PLX-C under humidified 5% CO2 atmosphere at 37° C. Supernatants were collected and subjected to cytokine analysis using ELISA kits for IFNγ (DIACLONE), TNFα (DIACLONE) and IL-10 (DIACLONE).

Results

The changes in manufacturing with Celligen as compared to Plurix resulted in several major differences (summarized in Table 10, below).

TABLE 10

Comparison between Plurix system (WO/2007/108003) and Celligen system (teachings of the present invention)

| Parameter | WO/2007/108003 | 3D adherent cells of the present teachings | Improvement |
|---|---|---|---|
| Working volume (ml) | 280 | 1500 | Scale up of the process. Higher production level in the present teachings (2-8 population doubling) |
| Weight of carrier (gr) | 1.4 | 30 | Scale up of the process in the present teachings. |
| Bed configuration | Conic, 50 ml column | Cylinder Packed bed | The present teachings - Better flow of medium and nutrients. WO/2007/108003 - Inefficient flow due to narrow outlet form the conic structure Better homogeneity of medium flow. Channeling in the plurix |
| Cell concentration at seeding (cell/gr carrier) | 3 × 10$^6$ cell/gr carrier | 5 × 10$^6$ cell/gr carrier | Better cell to cell interaction in the present teachings |
| Cell concentration at seeding (cell/ml) | 0.015 × 10$^6$ cell/ml | 0.1 × 10$^6$ cell/ml | Better cell to cell interaction in the present teachings |
| Seeding procedure | Seeding at low medium volume for 24 h followed by addition of medium to final working volume | Seeding at the final working volume while agitating | WO/2007/108003 - Heterogenic distribution of the cell culture inside the carrier bed Insufficient medium volume in the first 24 h of the run. Leading to unsuitable working conditions (acidic environment) Better product quality. Efficient harvest process. Better yield. Lower cost process in the present teachings |
| Production phase duration | 14-21 days | 4-10 days | |
| Mode of operation | Repeated batch - medium change twice a week | Perfusion mode - rate was adjusted according to the glucose concentration (the medium was changed at glucose concentration of 550 ± 50 mg/L) | Present teachings - Moderate changes of the conditions regarding medium composition throughout the run Continuous removal of toxic agents produced by the cells. In batch mode - lower concentration of essential nutrients (limiting factors) Less cell debris |
| Harvest procedure | Harvesting in 50 ml tubes Trypsinization 3 cycles | Harvesting inside the bioreactor Trypsinization 1 cycle | Present teachings - More efficient process Harvest is carried out in a close system. 1 trypsinization cycle - better quality of the cells. |
| Agitation | medium Circulation between reservoir container to the column using peristaltic pump | Cell lift impeller | Present teachings - Medium is flowing through the packed bed - Better supply of nutrients and oxygen to the culture. Homogeneity of the medium Improves other control loops (temp., DO, pH) |
| Temperature control | The production was carried out inside an incubator. Indirect temperature control (of the incubator chamber). Heat transfer via air interface | On-line direct control. Heat transfer via water jacket. | Present teachings - more accurate measurement of the culture temperature. Quick response. Short time to reach set point. |
| Temperature monitoring | Manually. Indirect water temperature monitoring. | On-line direct monitoring. | Present teachings - Better monitoring and control of the process. |

TABLE 10-continued

Comparison between Plurix system (WO/2007/108003) and Celligen system (teachings of the present invention)

| Parameter | WO/2007/108003 | 3D adherent cells of the present teachings | Improvement |
|---|---|---|---|
| DO monitoring | None | On-line monitoring | Quick response to malfunctions. Present teachings - Better monitoring and control of the process. Quick response to malfunctions |
| DO control | None. Introduction of air only | On-line direct control of a specific set point using Air, O₂ and N₂. | Present teachings - Better control of DO level. Better maintenance of a specified working conditions |
| pH monitoring and control | Only visual monitoring (Phenol red as part of the medium) | On-line Control and monitoring | Present teachings - Better control of pH level. Better maintenance of a specified working conditions |
| Aeration | Sparge only | Overlay (sparge as an option) | WO/2007/108003 - Aeration by sparge creates foam that might damage the cells. |

The changes in the manufacturing process resulted in changes in characteristics of the obtained adherent cells. These differences are summarized below.

Figure 6A:
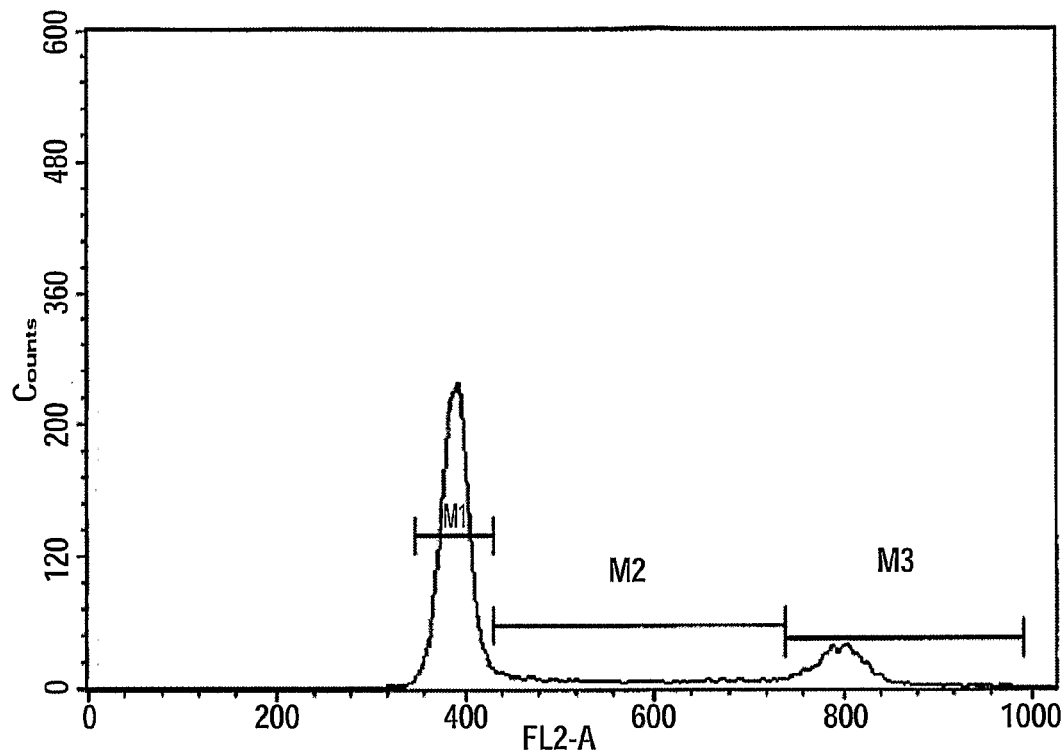
FIGS. 6A-B depict cell cycle analysis of 3D adherent cells manufacture by Plurix (designated PLX, FIG. 6B) and by Celligen (PLX-C, FIG. 6A). Cells were fixed in 70% EtOH O.N, centrifuged and re-suspended in a Propidium Iodide (PI) solution and then analyzed by FACS.
Figure 6B:
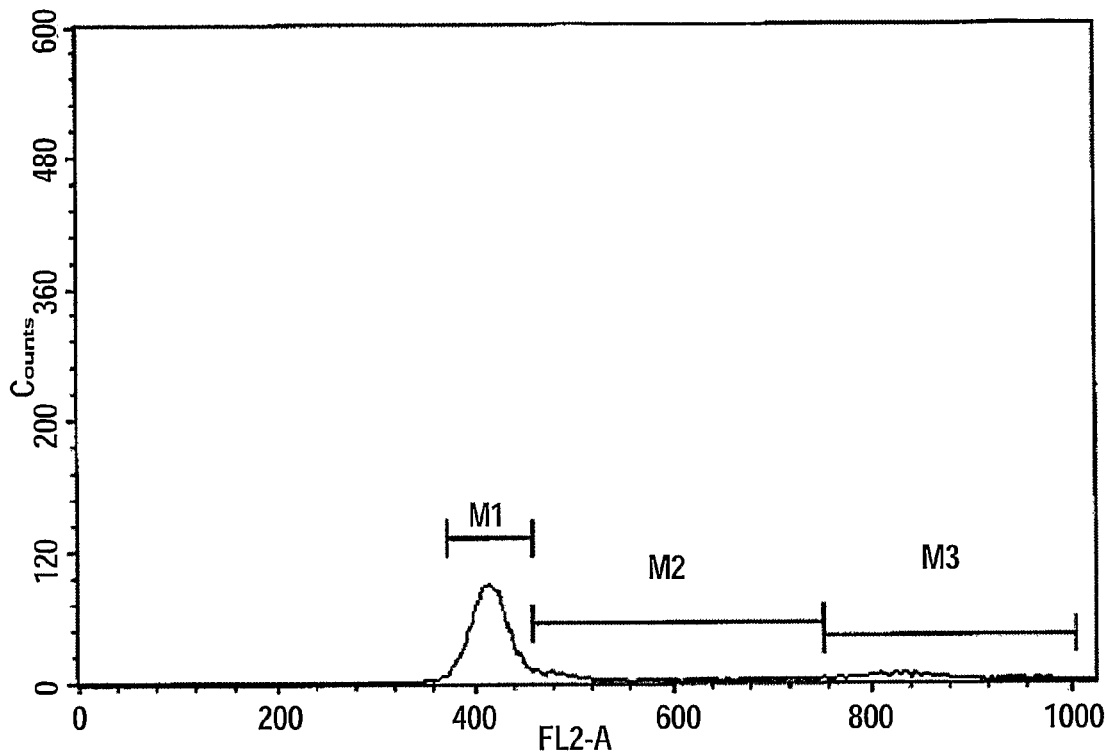

Cell Cycle Analysis of PLX Manufactured by Plurix Compared to PLX-C Manufactured by Celligen PLX-C cells obtained by Celligen were compared to PLX cells obtained by Plurix in order to examine the distribution of the cells between the different phases of the cell cycle. As is clear from FIGS. 6A-B, PLX-C cells expanded by Celligen exhibited typical proliferating profile (distribution of cells between the different phases of cell cycle). Specifically, 28% of cells were in S and G2/M phases (FIG. 6A). These results indicated that cells were harvested during proliferation and that the Celligen bioreactor conditions supported cell growth.

Microarray Comparison Between Plurix and Celligen Obtained Cells

Gene expression arrays enabled to simultaneously monitor genome-wide expression profiles of adherent cells derived from human full term placentas expanded by Plurix (PLX) or by Celligen (PLX-C). These results enabled to assess the molecular mechanism underlying phenotypic variation between cells obtained by these different growth methods (see Table 11, below).

TABLE 11

Gene expression in Plurix cells (WO/2007/108003) compared to Celligen cells (teachings of the present invention)

| Gene | Celligen vs Plurix (fold change) | p-value (treat) |
|---|---|---|
| interferon-induced protein with tetratricopeptide repeats | 17.52 | 0.0401812 |
| aldehyde dehydrogenase 1 family, member A1 | 16.76 | 0.00145807 |
| leukocyte-derived arginine aminopeptidase | 13.99 | 3.88E-06 |
| keratin 27 pseudogene 27 | 12.25 | 0.000224998 |
| similar to Keratin, type I cytoskeletal 18 (Cytokerati | 11.83 | 0.000304949 |
| G protein-coupled receptor, family C, group 5, member A | 10.35 | 3.39E-05 |
| integrin, alpha 6 | 9.84 | 0.0411667 |
| G protein-coupled receptor 126 | 8.73 | 0.00197635 |
| coagulation factor III (thromboplastin, tissue factor) | 7.36 | 0.012192 |
| Rho GDP dissociation inhibitor (GDI) beta | 7.36 | 0.00200066 |
| signal peptide, CUB domain, EGF-like 3 | 7.20 | 0.0255115 |
| interferon-induced protein with tetratricopeptide repeats | 7.09 | 0.0139777 |
| dickkopf homolog 1 (Xenopus laevis) | 7.06 | 3.06E-07 |
| NAD (P)H dehydrogenase, quinone 1 | 6.63 | 0.000282423 |
| keratin 18 | 6.46 | 0.000514523 |
| opioid growth factor receptor-like 1 | 5.96 | 0.00114551 |
| mal, T-cell differentiation protein-like | 5.95 | 0.00664216 |
| neurofilament, medium polypeptide 150 kDa | 5.86 | 0.0190611 |
| DEP domain containing 1 | 5.82 | 0.000370513 |
| cathepsin C | 5.72 | 0.00532262 |
| WAS | 5.47 | 0.00178153 |
| serpin peptidase inhibitor, clade B (ovalbumin), member | 5.44 | 0.0190218 |
| solute carrier family 7, (cationic amino acid transporte | 5.33 | 0.00688017 |
| interferon-induced protein with tetratricopeptide repea | 5.18 | 0.00357376 |
| NUF2, NDC80 kinetochore complex component, homolog (S. cere | 5.05 | 0.00276524 |
| SHC SH2-domain binding protein 1 | 4.95 | 0.00430878 |
| thioredoxin reductase 1 | 4.86 | 0.000197486 |

TABLE 11-continued

Gene expression in Plurix cells (WO/2007/108003) compared to Celligen cells (teachings of the present invention)

| Gene | Celligen vs Plurix (fold change) | p-value (treat) |
|---|---|---|
| lung cancer metastasis-associated protein | 4.85 | 0.00148024 |
| Rho GTPase activating protein 29 | 4.85 | 0.0466211 |
| cell division cycle 20 homolog (S. cerevisiae) | 4.80 | 0.00514206 |
| family with sequence similarity 111, member B | 4.63 | 0.000125819 |
| PDZ binding kinase | 4.54 | 0.00784983 |
| establishment of cohesion 1 homolog 2 (S. cerevisiae) | 4.53 | 0.000773033 |
| guanylate binding protein 4 | 4.47 | 0.000215944 |
| lipase A, lysosomal acid, cholesterol esterase (Wolman dise | 4.42 | 0.0167385 |
| kinesin family member 20A | 4.39 | 0.00582352 |
| KIAA0101 | 4.28 | 0.0105909 |
| cyclin-dependent kinase inhibitor 3 (CDK2-associated dual | 4.25 | 0.000732492 |
| thymidylate synthetase | 4.23 | 0.00685584 |
| chromosome 13 open reading frame 3 | 4.18 | 0.000548296 |
| aurora kinase A | 4.16 | 0.00632571 |
| nei endonuclease VIII-like 3 (E. coli) | 4.14 | 0.00115606 |
| centrosomal protein 55 kDa | 4.13 | 0.0021952 |
| oxidized low density lipoprotein (lectin-like) receptor 1 | 4.11 | 0.0205198 |
| denticleless homolog (Drosophila) | 4.05 | 0.00141153 |
| anillin, actin binding protein | 4.01 | 0.010923 |
| ribonucleotide reductase M2 polypeptide | 3.98 | 0.00834059 |
| ankyrin repeat domain 1 (cardiac muscle) | 3.93 | 0.00911953 |
| transcription factor 19 (SC1) | 3.89 | 0.00109627 |
| keratin 18 | 3.89 | 0.000112551 |
| non-SMC condensin I complex, subunit G | 3.88 | 0.00537097 |
| cyclin E2 | 3.87 | 0.000203389 |
| trypsinogen C | 3.86 | 0.00416276 |
| small nucleolar RNA, C | 3.81 | 0.0334484 |
| tight junction protein 2 (zona occludens 2) | 3.81 | 0.00012562 |
| kinesin family member 18A | 3.78 | 0.00134108 |
| kinesin family member 2C | 3.77 | 0.0059888 |
| shugoshin-like 1 (S. pombe) | 3.76 | 0.00101318 |
| polo-like kinase 1 (Drosophila) | 3.75 | 0.0140309 |
| thymidine kinase 1, soluble | 3.73 | 0.00124134 |
| transcription factor 19 (SC1) | 3.73 | 0.00124327 |
| transcription factor 19 (SC1) | 3.73 | 0.00124327 |
| claspin homolog (Xenopus laevis) | 3.71 | 0.00683624 |
| GINS complex subunit 1 (Psf1 homolog) | 3.69 | 0.00104515 |
| microsomal glutathione S-transferase 1 | 3.67 | 0.041701 |
| arylacetamide deacetylase-like 1 | 3.67 | 0.000902645 |
| SPC25, NDC80 kinetochore complex component, homolog (S. ce | 3.65 | 0.00568662 |
| integrin, alpha 4 (antigen CD49D, alpha 4 subunit of VLA-4 | 3.62 | 0.0158411 |
| catenin (cadherin-associated protein), alpha-like 1 | 3.57 | 7.46E−05 |
| discs, large homolog 7 (Drosophila) | 3.56 | 0.0317074 |
| v-myb myeloblastosis viral oncogene homolog (avian)-lik | 3.55 | 0.0043878 |
| serglycin | 3.54 | 0.0443487 |
| centromere protein N | 3.53 | 0.000540143 |
| cyclin A2 | 3.53 | 0.00965934 |
| heat shock 22 kDa protein 8 | 3.52 | 0.0219583 |
| sema domain, immunoglobulin domain (Ig), short basic doma | 3.49 | 0.008548 |
| Rho GTPase activating protein 11A | 3.49 | 0.00834174 |
| Fanconi anemia, complementation group I | 3.43 | 0.00464532 |
| BUB1 budding uninhibited by benzimidazoles 1 homolog (yeast | 3.42 | 0.0108258 |
| ovary-specific acidic protein | 3.42 | 0.00334641 |
| cholinergic receptor, muscarinic 2 | 3.41 | 0.0320078 |
| cell division cycle 2, G1 to S and G2 to M | 3.41 | 0.0017111 |
| protein regulator of cytokinesis 1 | 3.39 | 0.0325664 |
| minichromosome maintenance complex component 5 | 3.38 | 0.00475504 |
| sperm associated antigen 5 | 3.37 | 0.00906321 |
| maternal embryonic leucine zipper kinase | 3.34 | 0.00908391 |
| small nucleolar RNA, C | 3.33 | 0.0298703 |
| carnitine palmitoyltransferase 1A (liver) | 3.33 | 0.00170894 |
| similar to Ubiquitin-conjugating enzyme E2S (Ubiqui | 3.33 | 0.000415822 |
| kinesin family member 11 | 3.33 | 0.00915145 |
| NIMA (never in mitosis gene a)-related kinase 7 | 3.33 | 0.00159114 |
| ADAM metallopeptidase with thrombospondin type 1 motif, | 3.32 | 0.0102751 |
| transforming, acidic coiled-coil containing protein 3 | 3.31 | 0.0014577 |

TABLE 11-continued

Gene expression in Plurix cells (WO/2007/108003) compared to Celligen cells (teachings of the present invention)

| Gene | Celligen vs Plurix (fold change) | p-value (treat) |
|---|---|---|
| cyclin B1 | 3.29 | 0.0103092 |
| MAD2 mitotic arrest deficient-like 1 (yeast) | 3.28 | 0.00488102 |
| dihydrofolate reductase | 3.28 | 0.00178879 |
| NIPA-like domain containing 3 | 3.27 | 0.00164708 |
| cell division cycle associated 2 | 3.26 | 0.0122226 |
| apolipoprotein B mRNA editing enzyme, catalytic polypep | 3.26 | 0.00308692 |
| cyclin B2 | 3.25 | 0.016544 |
| endonuclease domain containing 1 | 3.24 | 0.000429245 |
| dihydrofolate reductase pseudogene | 3.23 | 0.00141306 |
| ATPase, Na+ | 3.23 | 0.000381464 |
| replication factor C (activator 1) 3, 38 kDa | 3.23 | 0.00109668 |
| WD repeat domain 76 | 3.22 | 0.0023531 |
| pleckstrin 2 | 3.17 | 0.0304429 |
| Rac GTPase activating protein 1 | 3.17 | 0.00381613 |
| PHD finger protein 19 | 3.17 | 0.000177604 |
| deleted in lymphocytic leukemia, 2 | 3.15 | 0.0109528 |
| centromere protein I | 3.15 | 0.0106816 |
| BRCA1 associated RING domain 1 | 3.14 | 0.000540414 |
| regulator of G-protein signalling 4 | 3.13 | 0.00781061 |
| STAM binding protein-like 1 | 3.11 | 0.0181743 |
| sulfiredoxin 1 homolog (S. cerevisiae) | 3.10 | 5.14E−05 |
| chromosome 15 open reading frame 23 | 3.08 | 0.000147331 |
| TTK protein kinase | 3.08 | 0.0112171 |
| non-SMC condensin II complex, subunit G2 | 3.08 | 0.0130322 |
| villin 2 (ezrin) | 3.07 | 0.0131934 |
| stomatin | 3.06 | 0.00387095 |
| protein tyrosine phosphatase-like A domain containing | 3.06 | 0.0419644 |
| serpin peptidase inhibitor, clade B (ovalbumin), member | 3.05 | 0.0030439 |
| kinesin family member 4A | 3.05 | 0.0114203 |
| hypothetical protein DKFZp762E1312 | 3.05 | 0.00726778 |
| ubiquitin-conjugating enzyme E2S | 3.04 | 0.00118205 |
| hydroxysteroid dehydrogenase like 2 | 3.03 | 3.71E−05 |
| ATPase family, AAA domain containing 2 | 3.01 | 0.00415258 |
| TPX2, microtubule-associated, homolog (Xenopus laevis) | 3.00 | 0.0253137 |
| histone cluster 1, H4d | 3.00 | 0.030183 |
| kinesin family member 23 | 2.99 | 0.00790585 |
| heat shock 70 kDa protein 2 | 2.99 | 0.0215102 |
| origin recognition complex, subunit 1-like (yeast) | 2.99 | 0.00207753 |
| dihydrofolate reductase | 2.98 | 0.00307793 |
| hyaluronan-mediated motility receptor (RHAMM) | 2.97 | 0.00467816 |
| 3'-phosphoadenosine 5'-phosphosulfate synthase 2 | 2.97 | 1.43E−05 |
| glycerol-3-phosphate dehydrogenase 2 (mitochondrial) | 2.95 | 0.00211969 |
| nucleolar and spindle associated protein 1 | 2.95 | 0.00520875 |
| diaphanous homolog 3 (Drosophila) | 2.95 | 0.00107709 |
| kinesin family member 14 | 2.94 | 0.00947901 |
| histone cluster 1, H1b | 2.93 | 0.0470898 |
| guanine nucleotide binding protein (G protein), alpha inhi | 2.92 | 0.00184597 |
| minichromosome maintenance complex component 8 | 2.92 | 0.000841489 |
| cancer susceptibility candidate 5 | 2.92 | 0.0330594 |
| leukotriene B4 12-hydroxydehydrogenase | 2.92 | 0.000685452 |
| glutamate-cysteine ligase, modifier subunit | 2.91 | 0.00378868 |
| forkhead box M1 | 2.91 | 0.0203154 |
| adipose differentiation-related protein | 2.90 | 0.000331751 |
| membrane bound O-acyltransferase domain containing 1 | 2.90 | 0.01185 |
| ubiquitin-conjugating enzyme E2T (putative) | 2.90 | 0.00741886 |
| cell division cycle associated 3 | 2.89 | 0.006289 |
| integrin, alpha 3 (antigen CD49C, alpha 3 subunit of VLA-3 | 2.88 | 0.00574148 |
| coagulation factor XIII, B polypeptide | 2.88 | 0.0294465 |
| RAD51 homolog (RecA homolog, E. coli) (S. cerevisiae) | 2.87 | 0.000854739 |
| ATP-binding cassette, sub-family C (CFTR | 2.87 | 0.00382491 |
| family with sequence similarity 29, member A | 2.85 | 0.00111165 |
| SH2 domain containing 4A | 2.84 | 0.0323646 |
| membrane protein, palmitoylated 1, 55 kDa | 2.84 | 0.000396285 |
| CDC28 protein kinase regulatory subunit 1B | 2.84 | 0.0107391 |
| PSMC3 interacting protein | 2.84 | 0.00766442 |
| elastin microfibril interfacer 2 | 2.84 | 0.0192072 |
| topoisomerase (DNA) II alpha 170 kDa | 2.83 | 0.0321109 |
| transmembrane protein 106C | 2.82 | 0.000214223 |
| histone cluster 1, H3b | 2.80 | 0.0304598 |

TABLE 11-continued

Gene expression in Plurix cells (WO/2007/108003) compared to Celligen cells (teachings of the present invention)

| Gene | Celligen vs Plurix (fold change) | p-value (treat) |
|---|---|---|
| chromosome 18 open reading frame 24 | 2.80 | 0.00347442 |
| epidermal growth factor receptor pathway substrate 8 | 2.79 | 0.0194949 |
| high-mobility group nucleosomal binding domain 2 | 2.78 | 0.0030536 |
| SCL | 2.78 | 0.00390288 |
| hect domain and RLD 4 | 2.78 | 0.00679184 |
| ASF1 anti-silencing function 1 homolog B (*S. cerevisiae*) | 2.77 | 0.00543408 |
| thyroid hormone receptor interactor 13 | 2.76 | 0.0118319 |
| cell division cycle associated 8 | 2.75 | 0.00619878 |
| kinesin family member C1 | 2.74 | 0.00821937 |
| high-mobility group nucleosomal binding domain 2 | 2.73 | 0.00384071 |
| ornithine decarboxylase 1 | 2.73 | 0.00144868 |
| v-myb myeloblastosis viral oncogene homolog (avian)-like 2 | 2.71 | 0.00989416 |
| KIT ligand | 2.70 | 0.00641955 |
| dual-specificity tyrosine- (Y)-phosphorylation regulated ki | 2.70 | 0.0234606 |
| intraflagellar transport 80 homolog (*Chlamydomonas*) | 2.70 | 0.0247286 |
| transmembrane protein 48 | 2.69 | 0.00458248 |
| EBNA1 binding protein 2 | 2.69 | 0.00296292 |
| ZW10 interactor | 2.69 | 1.88E−05 |
| exonuclease 1 | 2.68 | 0.00739393 |
| transketolase (Wernicke-Korsakoff syndrome) | 2.68 | 1.92E−05 |
| somatostatin receptor 1 | 2.68 | 0.0144901 |
| isocitrate dehydrogenase 3 (NAD+) alpha | 2.67 | 0.00297129 |
| cytoskeleton associated protein 2 | 2.67 | 0.0030499 |
| minichromosome maintenance complex component 4 | 2.67 | 0.00342054 |
| inhibitor of DNA binding 1, dominant negative helix-loop-hel | 2.66 | 0.036485 |
| CDC28 protein kinase regulatory subunit 1B | 2.66 | 0.0145263 |
| keratin 18 | 2.66 | 8.40E−05 |
| CD97 molecule | 2.66 | 0.00994045 |
| chromosome 6 open reading frame 173 | 2.64 | 0.00222408 |
| BTB (POZ) domain containing 3 | 2.62 | 0.0166824 |
| deafness, autosomal dominant 5 | 2.62 | 0.00235481 |
| KIAA0286 protein | 2.62 | 0.00130563 |
| Fanconi anemia, complementation group D2 | 2.61 | 0.0281405 |
| polo-like kinase 4 (*Drosophila*) | 2.60 | 0.00209633 |
| ribonucleotide reductase M1 polypeptide | 2.60 | 0.000170076 |
| malic enzyme 1, NADP (+)-dependent, cytosolic | 2.59 | 0.0435444 |
| non-SMC condensin I complex, subunit H | 2.59 | 0.0216752 |
| S100 calcium binding protein A3 | 2.58 | 0.0324073 |
| ubiquitin-conjugating enzyme E2L 3 | 2.57 | 0.00343347 |
| BUB1 budding uninhibited by benzimidazoles 1 homolog beta | 2.56 | 0.0166047 |
| glycerol kinase | 2.55 | 2.66E−05 |
| TAF9B RNA polymerase II, TATA box binding protein (TBP)-as | 2.54 | 0.0170365 |
| TAF9B RNA polymerase II, TATA box binding protein (TBP)-as | 2.54 | 0.0170365 |
| histone cluster 1, H2bg | 2.52 | 0.000180822 |
| high-mobility group box 2 | 2.52 | 0.0196872 |
| NIMA (never in mitosis gene a)-related kinase 2 | 2.50 | 0.00289469 |
| proline rich 11 | 2.50 | 0.0357125 |
| myopalladin | 2.49 | 0.0255088 |
| brix domain containing 1 | 2.49 | 0.00471977 |
| cell division cycle associated 5 | 2.49 | 0.01021 |
| fucosidase, alpha-L-2, plasma | 2.49 | 0.00540929 |
| cyclin-dependent kinase 2 | 2.49 | 0.00250724 |
| lamin B receptor | 2.49 | 0.000151784 |
| hypoxanthine phosphoribosyltransferase 1 (Lesch-Nyhan synd | 2.49 | 0.000634057 |
| tripartite motif-containing 25 | 2.47 | 0.0456344 |
| proteasome (prosome, macropain) subunit, beta type, 9 (lar | 2.46 | 0.0202595 |
| proteasome (prosome, macropain) subunit, beta type, 9 (lar | 2.46 | 0.0202595 |
| proteasome (prosome, macropain) subunit, beta type, 9 (lar | 2.46 | 0.0202595 |
| sphingomyelin synthase 2 | 2.46 | 0.0020701 |
| transmembrane protein 62 | 2.45 | 0.00761064 |
| glucose-6-phosphate dehydrogenase | 2.44 | 0.00278311 |
| PHD finger protein 1 | 2.44 | 0.010191 |
| retinoblastoma-like 1 (p107) | 2.44 | 0.00319946 |
| KIAA1524 | 2.43 | 0.0380688 |

TABLE 11-continued

Gene expression in Plurix cells (WO/2007/108003) compared to Celligen cells (teachings of the present invention)

| Gene | Celligen vs Plurix (fold change) | p-value (treat) |
|---|---|---|
| ST6 (alpha-N-acetyl-neuraminyl-2,3-beta-galactosyl-1, | 2.43 | 0.00830766 |
| cofilin 2 (muscle) | 2.43 | 0.0459235 |
| hypothetical protein LOC201725 | 2.42 | 0.000313319 |
| cell division cycle 25 homolog A (S. pombe) | 2.42 | 0.000341692 |
| breast cancer 1, early onset | 2.41 | 0.0180553 |
| transaldolase 1 | 2.41 | 0.00199537 |
| mRNA turnover 4 homolog (S. cerevisiae) | 2.41 | 0.00373104 |
| glucosaminyl (N-acetyl) transferase 1, core 2 (beta-1,6-N- | 2.41 | 0.0197148 |
| cysteine rich transmembrane BMP regulator 1 (chordin-like) | 2.41 | 0.0267286 |
| tissue factor pathway inhibitor (lipoprotein-associated | 2.40 | 0.0356227 |
| chromosome 16 open reading frame 59 | 2.40 | 0.00185191 |
| glycogenin 1 | 2.39 | 0.0224317 |
| transmembrane protein 154 | 2.39 | 0.0045589 |
| tubulointerstitial nephritis antigen-like 1 | 2.39 | 0.00510812 |
| CTP synthase | 2.38 | 8.80E−05 |
| phenylalanyl-tRNA synthetase, beta subunit | 2.38 | 0.000245973 |
| geminin, DNA replication inhibitor | 2.38 | 0.00167629 |
| lamin B1 | 2.37 | 0.0477748 |
| SPC24, NDC80 kinetochore complex component, homolog (S. ce | 2.36 | 0.00287227 |
| glutathione reductase | 2.36 | 0.00353875 |
| ribosomal protein L22-like 1 | 2.36 | 0.00335381 |
| fumarylacetoacetate hydrolase (fumarylacetoacetase) | 2.36 | 3.88E−05 |
| small nucleolar RNA, C | 2.35 | 0.0188991 |
| family with sequence similarity 64, member A | 2.35 | 0.0019785 |
| epithelial cell transforming sequence 2 oncogene | 2.35 | 0.000571152 |
| polymerase (DNA directed), epsilon 2 (p59 subunit) | 2.34 | 0.00479612 |
| glycerol kinase | 2.34 | 3.37E−06 |
| glutathione S-transferase M2 (muscle) | 2.33 | 0.0402076 |
| elongation factor, RNA polymerase II, 2 | 2.33 | 0.0130017 |
| thioredoxin | 2.33 | 0.009636 |
| polymerase (DNA directed), alpha 2 (70 kD subunit) | 2.32 | 0.0033903 |
| breast cancer 2, early onset | 2.32 | 0.00586847 |
| CDC45 cell division cycle 45-like (S. cerevisiae) | 2.32 | 0.00735977 |
| H2A histone family, member Z | 2.32 | 0.0129697 |
| transporter 1, ATP-binding cassette, sub-family B (MDR | 2.31 | 0.0164234 |
| transporter 1, ATP-binding cassette, sub-family B (MDR | 2.31 | 0.0164234 |
| transporter 1, ATP-binding cassette, sub-family B (MDR | 2.31 | 0.0164234 |
| nucleolar complex associated 3 homolog (S. cerevisiae) | 2.30 | 0.000373346 |
| ATPase, Ca++ transporting, plasma membrane 4 | 2.30 | 0.023011 |
| minichromosome maintenance complex component 7 | 2.30 | 0.0457691 |
| TIMELESS interacting protein | 2.29 | 0.00771062 |
| von Hippel-Lindau binding protein 1 | 2.28 | 0.00329061 |
| ras-related C3 botulinum toxin substrate 2 (rho family, sma | 2.28 | 0.0292466 |
| thymopoietin | 2.28 | 0.0223176 |
| peptidylprolyl isomerase F (cyclophilin F) | 2.28 | 0.00093846 |
| activated leukocyte cell adhesion molecule | 2.27 | 0.00242163 |
| polycomb group ring finger 5 | 2.27 | 0.000294142 |
| Ran GTPase activating protein 1 | 2.27 | 9.68E−05 |
| replication factor C (activator 1) 4, 37 kDa | 2.26 | 0.00164152 |
| tubulin, beta 2C | 2.26 | 0.000346744 |
| minichromosome maintenance complex component 10 | 2.26 | 0.0037925 |
| H2B histone family, member S | 2.25 | 0.000885505 |
| gamma-glutamyl hydrolase (conjugase, folylpolygammaglutamyl | 2.25 | 0.0195219 |
| transcription termination factor, RNA polymerase II | 2.25 | 0.000393489 |
| polymerase (DNA directed), delta 2, regulatory subunit 50k | 2.25 | 0.0123823 |
| transporter 1, ATP-binding cassette, sub-family B (MDR | 2.25 | 0.00859077 |
| transporter 1, ATP-binding cassette, sub-family B (MDR | 2.25 | 0.00859077 |
| transporter 1, ATP-binding cassette, sub-family B (MDR | 2.25 | 0.00859077 |
| histone cluster 1, H2bf | 2.25 | 0.0124279 |
| eukaryotic translation initiation factor 1A, X-linked | 2.24 | 0.00330183 |
| phosphoglucomutase 2 | 2.24 | 0.00818204 |

TABLE 11-continued

Gene expression in Plurix cells (WO/2007/108003) compared to Celligen cells (teachings of the present invention)

| Gene | Celligen vs Plurix (fold change) | p-value (treat) |
|---|---|---|
| peroxisomal D3,D2-enoyl-CoA isomerase | 2.24 | 0.00148722 |
| interferon-induced protein with tetratricopeptide repeats | 2.24 | 0.0177928 |
| G-2 and S-phase expressed 1 | 2.23 | 0.0241887 |
| minichromosome maintenance complex component 2 | 2.23 | 0.0021347 |
| family with sequence similarity 72, member A | 2.23 | 0.00143248 |
| RMI1, RecQ mediated genome instability 1, homolog (S. cerev | 2.23 | 0.00294705 |
| FLJ20105 protein | 2.23 | 0.0127979 |
| multiple coagulation factor deficiency 2 | 2.22 | 0.0116892 |
| phytoceramidase, alkaline | 2.22 | 0.0157729 |
| coiled-coil domain containing 68 | 2.22 | 0.00227586 |
| dedicator of cytokinesis 11 | 2.21 | 0.00697577 |
| platelet-derived growth factor alpha polypeptide | 2.21 | 0.00176418 |
| N-acylsphingosine amidohydrolase (non-lysosomal cerami | 2.20 | 0.00728536 |
| S-phase kinase-associated protein 2 (p45) | 2.20 | 0.00230153 |
| polymerase (RNA) III (DNA directed) polypeptide G (32 kD) | 2.20 | 0.0298794 |
| ADP-ribosylation factor-like 6 interacting protein 1 | 2.20 | 0.00139745 |
| histone cluster 1, H2bh | 2.19 | 0.0377748 |
| origin recognition complex, subunit 5-like (yeast) | 2.19 | 0.049697 |
| CDC28 protein kinase regulatory subunit 2 | 2.19 | 0.0128024 |
| histone cluster 1, H4c | 2.19 | 0.0112695 |
| hypothetical protein LOC729012 | 2.19 | 0.000446087 |
| DEAD (Asp-Glu-Ala-Asp) box polypeptide 39 | 2.19 | 0.000340561 |
| chromatin assembly factor 1, subunit B (p60) | 2.18 | 0.0119687 |
| MLF1 interacting protein | 2.18 | 0.0177203 |
| microtubule associated serine | 2.18 | 0.00536974 |
| MHC class I polypeptide-related sequence B | 2.18 | 0.0165406 |
| shugoshin-like 2 (S. pombe) | 2.18 | 0.000852557 |
| COP9 constitutive photomorphogenic homolog subunit 6 (Arab | 2.18 | 0.000793512 |
| methylenetetrahydrofolate dehydrogenase (NADP+ dependent) | 2.18 | 0.00119726 |
| chromosome 6 open reading frame 167 | 2.18 | 0.0011095 |
| pituitary tumor-transforming 1 | 2.17 | 0.0485166 |
| ribonuclease H2, subunit A | 2.17 | 0.00669936 |
| X-ray repair complementing defective repair in Chinese ham | 2.16 | 0.0369865 |
| membrane protein, palmitoylated 5 (MAGUK p55 subfamily memb | 2.16 | 0.00211873 |
| karyopherin alpha 2 (RAG cohort 1, importin alpha 1) | 2.16 | 0.000650645 |
| pleckstrin homology domain containing, family A (phosphoi | 2.15 | 0.0256434 |
| ribosomal protein L39-like | 2.15 | 0.00429384 |
| karyopherin alpha 2 (RAG cohort 1, importin alpha 1) | 2.15 | 0.000700649 |
| amyloid beta (A4) precursor protein-binding, family B, m | 2.15 | 0.00201004 |
| minichromosome maintenance complex component 3 | 2.14 | 0.0018389 |
| histone cluster 1, H2ai | 2.14 | 0.0129155 |
| chromosome 13 open reading frame 34 | 2.14 | 0.000702936 |
| RAD18 homolog (S. cerevisiae) | 2.14 | 0.0016685 |
| WD repeat and HMG-box DNA binding protein 1 | 2.13 | 0.0034833 |
| sulfide quinone reductase-like (yeast) | 2.13 | 0.0473641 |
| chromosome 16 open reading frame 63 | 2.12 | 0.000804179 |
| M-phase phosphoprotein 1 | 2.12 | 0.0271814 |
| minichromosome maintenance complex component 6 | 2.12 | 0.0161279 |
| homeobox A9 | 2.11 | 0.00520942 |
| fibroblast growth factor 9 (glia-activating factor) | 2.10 | 0.0475844 |
| cell division cycle 25 homolog C (S. pombe) | 2.10 | 0.0169914 |
| chromosome 9 open reading frame 64 | 2.10 | 0.0265979 |
| U2AF homology motif (UHM) kinase 1 | 2.09 | 0.0255167 |
| replication factor C (activator 1) 2, 40 kDa | 2.09 | 0.00768959 |
| hypothetical protein LOC440894 | 2.09 | 0.0103358 |
| small nuclear ribonucleoprotein D1 polypeptide 16 kDa | 2.09 | 0.0334665 |
| CSE1 chromosome segregation 1-like (yeast) | 2.09 | 0.0013662 |
| phosphatidylinositol glycan anchor biosynthesis, class W | 2.09 | 0.0151967 |
| centromere protein O | 2.09 | 0.00397056 |
| family with sequence similarity 20, member B | 2.09 | 0.00460031 |
| hypothetical protein FLJ40869 | 2.09 | 0.00444509 |
| guanine nucleotide binding protein (G protein), gamma 11 | 2.08 | 0.00140559 |

TABLE 11-continued

Gene expression in Plurix cells (WO/2007/108003) compared to Celligen cells (teachings of the present invention)

| Gene | Celligen vs Plurix (fold change) | p-value (treat) |
|---|---|---|
| calcyclin binding protein | 2.08 | 0.00524566 |
| ATP-binding cassette, sub-family E (OABP), member 1 | 2.08 | 0.00454751 |
| CD44 molecule (Indian blood group) | 2.08 | 0.000651436 |
| exosome component 8 | 2.08 | 0.00132017 |
| family with sequence similarity 102, member B | 2.08 | 0.025743 |
| histone cluster 2, H3d | 2.07 | 0.0102932 |
| family with sequence similarity 33, member A | 2.07 | 0.000318673 |
| Fanconi anemia, complementation group B | 2.07 | 0.000255109 |
| kinesin family member 22 | 2.07 | 0.0192406 |
| histone cluster 1, H2ai | 2.07 | 0.0161621 |
| vaccinia related kinase 1 | 2.06 | 0.0233182 |
| integrator complex subunit 7 | 2.06 | 0.000841371 |
| flap structure-specific endonuclease 1 | 2.06 | 0.006882 |
| hypothetical protein FLJ25416 | 2.06 | 0.000177531 |
| ecotropic viral integration site 2B | 2.06 | 0.0171408 |
| retinitis pigmentosa 2 (X-linked recessive) | 2.05 | 0.0264185 |
| centromere protein L | 2.05 | 0.000880856 |
| cofactor required for Sp1 transcriptional activation, subu | 2.04 | 0.00141809 |
| chromosome 20 open reading frame 121 | 2.04 | 0.0146323 |
| family with sequence similarity 72, member A | 2.04 | 0.00162905 |
| family with sequence similarity 72, member A | 2.04 | 0.00165234 |
| eukaryotic translation initiation factor 1A, X-linked | 2.04 | 0.00520549 |
| elongation factor, RNA polymerase II, 2 | 2.03 | 0.0458007 |
| ATPase, Na+ | 2.03 | 0.0189108 |
| histone cluster 1, H3a | 2.03 | 0.0244273 |
| brix domain containing 1 | 2.03 | 0.00981178 |
| sushi domain containing 1 | 2.03 | 0.0258164 |
| ectonucleoside triphosphate diphosphohydrolase 6 (putativ | 2.03 | 0.00423628 |
| fructosamine 3 kinase | 2.03 | 0.00470972 |
| Bloom syndrome | 2.02 | 0.0209259 |
| tubulin, alpha 1c | 2.01 | 0.00862586 |
| E2F transcription factor 2 | 2.01 | 0.0496479 |
| exosome component 2 | 2.01 | 0.00649147 |
| kinesin family member 22 | 2.01 | 0.0242075 |
| LTV1 homolog (*S. cerevisiae*) | 2.01 | 0.00812652 |
| dihydrolipoamide S-acetyltransferase (E2 component of pyruv | 2.01 | 0.00179011 |
| v-ral simian leukemia viral oncogene homolog B (ras related | 2.01 | 0.012225 |
| ring finger and WD repeat domain 3 | 2.01 | 0.0013797 |
| annexin A1 | 2.01 | 0.0173578 |
| elaC homolog 2 (*E. coli*) | 2.00 | 0.00266504 |
| aldehyde dehydrogenase 9 family, member A1 | 2.00 | 0.00911609 |
| tubulin, alpha 4a | 2.00 | 0.0435427 |
| nuclear pore complex interacting protein | −2.00 | 0.00111223 |
| oculomedin | −2.01 | 0.00778869 |
| similar to PI-3-kinase-related kinase SMG-1 | −2.01 | 0.0356628 |
| golgi autoantigen, golgin subfamily a-like pseudogene | −2.01 | 0.00770626 |
| spectrin repeat containing, nuclear envelope 1 | −2.01 | 0.00438469 |
| nuclear pore complex interacting protein | −2.01 | 0.00117582 |
| sushi, nidogen and EGF-like domains 1 | −2.01 | 0.00161129 |
| integrin, alpha V (vitronectin receptor, alpha polypeptide | −2.02 | 0.00252702 |
| cyclin-dependent kinase inhibitor 2B (p15, inhibits CDK4) | −2.04 | 0.0150268 |
| lysyl oxidase-like 4 | −2.04 | 0.0120148 |
| nuclear pore complex interacting protein | −2.04 | 0.000213956 |
| calcium | −2.04 | 0.00657494 |
| calsyntenin 3 | −2.04 | 0.00300887 |
| cell adhesion molecule 1 | −2.05 | 0.0261129 |
| solute carrier family 22 (organic cation transporter), | −2.05 | 0.0137275 |
| RUN and FYVE domain containing 3 | −2.05 | 0.00387265 |
| glucosidase, alpha; acid (Pompe disease, glycogen storage di | −2.05 | 0.000418401 |
| nuclear pore complex interacting protein | −2.05 | 0.00988632 |
| proline-rich nuclear receptor coactivator 1 | −2.06 | 0.0039587 |
| membrane metallo-endopeptidase | −2.06 | 0.0152684 |
| PHD finger protein 21A | −2.06 | 0.00980401 |
| Rho GTPase-activating protein | −2.06 | 0.00705186 |
| homeobox B6 | −2.06 | 0.00301714 |
| nuclear pore complex interacting protein | −2.07 | 0.00032839 |
| phospholipase A2 receptor 1, 180 kDa | −2.07 | 0.00069343 |

TABLE 11-continued

Gene expression in Plurix cells (WO/2007/108003) compared to Celligen cells (teachings of the present invention)

| Gene | Celligen vs Plurix (fold change) | p-value (treat) |
|---|---|---|
| nuclear pore complex interacting protein | −2.08 | 0.000352007 |
| slit homolog 3 (*Drosophila*) | −2.08 | 0.02844 |
| nuclear pore complex interacting protein | −2.09 | 0.000414309 |
| cyclin-dependent kinase 6 | −2.09 | 0.0456892 |
| dynamin 1 | −2.09 | 0.00139674 |
| jumonji, AT rich interactive domain 1B | −2.09 | 0.00861002 |
| calcium binding and coiled-coil domain 1 | −2.09 | 0.00370041 |
| insulin-like growth factor 1 receptor | −2.09 | 0.00114467 |
| nuclear pore complex interacting protein | −2.10 | 0.000377834 |
| CD82 molecule | −2.10 | 0.0175517 |
| bromodomain adjacent to zinc finger domain, 2B | −2.10 | 9.88E−05 |
| — | −2.10 | 0.00666187 |
| synaptotagmin XI | −2.11 | 0.0129428 |
| KIAA1546 | −2.11 | 0.000255634 |
| jun B proto-oncogene | −2.12 | 0.0120169 |
| CXXC finger 6 | −2.12 | 0.0277527 |
| nuclear pore complex interacting protein | −2.14 | 0.00282604 |
| Cdon homolog (mouse) | −2.15 | 0.0350357 |
| B-cell CLL | −2.15 | 0.00343507 |
| nuclear pore complex interacting protein | −2.15 | 0.00263888 |
| v-abl Abelson murine leukemia viral oncogene homolog 1 | −2.16 | 0.0136688 |
| nuclear pore complex interacting protein | −2.16 | 0.00583397 |
| FAT tumor suppressor homolog 1 (*Drosophila*) | −2.18 | 0.0158766 |
| transformer-2 alpha | −2.18 | 0.012256 |
| chimerin (chimaerin) 1 | −2.18 | 0.0287031 |
| milk fat globule-EGF factor 8 protein | −2.18 | 0.000987073 |
| vitamin D (1,25-dihydroxyvitamin D3) receptor | −2.19 | 0.000192208 |
| neuroblastoma, suppression of tumorigenicity 1 | −2.20 | 0.00090639 |
| jumonji domain containing 1A | −2.20 | 0.0188513 |
| WNK lysine deficient protein kinase 1 | −2.21 | 1.57E−05 |
| protocadherin beta 14 | −2.21 | 0.0103892 |
| cortactin binding protein 2 | −2.21 | 2.28E−05 |
| WW domain containing transcription regulator 1 | −2.22 | 0.0379899 |
| cyclin L1 | −2.22 | 0.00831474 |
| nuclear factor of activated T-cells, cytoplasmic, calcine | −2.22 | 0.00786451 |
| pellino homolog 1 (*Drosophila*) | −2.23 | 0.00939357 |
| golgi autoantigen, golgin subfamily a-like pseudogene | −2.24 | 0.00603583 |
| chromosome 7 open reading frame 10 | −2.26 | 0.00738442 |
| golgi autoantigen, golgin subfamily a-like pseudogene | −2.27 | 0.00320764 |
| small Cajal body-specific RNA 17 | −2.27 | 0.0301336 |
| latent transforming growth factor beta binding protein 2 | −2.29 | 4.08E−05 |
| golgi autoantigen, golgin subfamily a, 8A | −2.29 | 0.0111179 |
| inhibin, beta A (activin A, activin AB alpha polypeptide) | −2.29 | 0.00877271 |
| solute carrier family 41, member 2 | −2.30 | 0.00453672 |
| forkhead box P1 | −2.30 | 0.0463138 |
| matrix metallopeptidase 14 (membrane-inserted) | −2.31 | 1.93E−05 |
| transcription factor 4 | −2.31 | 0.0367869 |
| jun oncogene | −2.32 | 7.21E−05 |
| neuroepithelial cell transforming gene 1 | −2.33 | 0.0109689 |
| asporin | −2.33 | 0.000659873 |
| v-fos FBJ murine osteosarcoma viral oncogene homolog | −2.35 | 0.0138624 |
| ephrin-B2 | −2.36 | 0.00611474 |
| WD repeat and SOCS box-containing 1 | −2.36 | 0.0387851 |
| similar to dJ402H5.2 (novel protein similar to wo | −2.36 | 0.00621503 |
| PX domain containing serine | −2.38 | 0.000927628 |
| collagen, type VII, alpha 1 (epidermolysis bullosa, dystr | −2.38 | 0.00109233 |
| AE binding protein 1 | −2.39 | 0.000105628 |
| peroxidasin homolog (*Drosophila*) | −2.40 | 0.00219049 |
| calcium channel, voltage-dependent, L type, alpha 1C sub | −2.41 | 0.0189661 |
| Prader-Willi syndrome chromosome region 1 | −2.45 | 0.0415526 |
| midline 1 (Opitz | −2.45 | 0.00130803 |
| nuclear pore complex interacting protein | −2.45 | 0.00354416 |
| chromosome 1 open reading frame 54 | −2.47 | 0.0186089 |
| transmembrane protein 16A | −2.48 | 0.0481085 |
| basic helix-loop-helix domain containing, class B, 2 | −2.49 | 0.00270257 |
| nuclear pore complex interacting protein | −2.50 | 0.00316496 |
| runt-related transcription factor 1 (acute myeloid leukemi | −2.50 | 0.000607387 |

TABLE 11-continued

Gene expression in Plurix cells (WO/2007/108003) compared to Celligen cells (teachings of the present invention)

| Gene | Celligen vs Plurix (fold change) | p-value (treat) |
|---|---|---|
| zinc finger protein 292 | −2.50 | 0.029832 |
| fibronectin leucine rich transmembrane protein 2 | −2.51 | 0.0135122 |
| nuclear pore complex interacting protein | −2.51 | 0.00283418 |
| potassium voltage-gated channel, subfamily G, member 1 | −2.54 | 0.0244306 |
| interleukin 19 | −2.54 | 0.0310328 |
| transforming growth factor, beta 3 | −2.54 | 0.0287865 |
| dihydropyrimidinase-like 3 | −2.55 | 0.0165203 |
| golgi autoantigen, golgin subfamily a, 8B | −2.56 | 0.0121417 |
| hypothetical protein PRO2012 | −2.57 | 0.00756704 |
| SATB homeobox 2 | −2.57 | 0.039781 |
| t-complex 11 (mouse)-like 2 | −2.57 | 0.0324227 |
| ring finger protein 122 | −2.57 | 0.0236621 |
| chromosome 8 open reading frame 57 | −2.59 | 0.00261522 |
| ADAM metallopeptidase with thrombospondin type 1 motif, | −2.60 | 0.0113968 |
| sushi, von Willebrand factor type A, EGF and pentraxin dom | −2.63 | 2.23E−05 |
| ST6 beta-galactosamide alpha-2,6-sialyltranferase 2 | −2.64 | 0.0216987 |
| sortilin-related VPS10 domain containing receptor 2 | −2.65 | 0.00936311 |
| protocadherin beta 9 | −2.66 | 0.0285124 |
| chromosome 5 open reading frame 13 | −2.67 | 0.00410172 |
| Enah | −2.68 | 0.0077547 |
| pyridoxal-dependent decarboxylase domain containing 2 | −2.69 | 0.00683647 |
| similar to nuclear pore complex interacting protein | −2.70 | 0.0187322 |
| nuclear pore complex interacting protein | −2.70 | 0.00368967 |
| transmembrane protein 119 | −2.70 | 0.00801387 |
| chromosome 14 open reading frame 37 | −2.70 | 0.0182453 |
| sushi-repeat-containing protein, X-linked 2 | −2.71 | 0.0253856 |
| PDZ domain containing RING finger 3 | −2.71 | 0.00931014 |
| collagen, type XII; alpha 1 | −2.72 | 0.000204664 |
| matrix-remodelling associated 5 | −2.72 | 0.000317637 |
| collagen, type V, alpha 1 | −2.72 | 0.0166427 |
| dystrophin related protein 2 | −2.72 | 0.0137557 |
| ATP-binding cassette, sub-family A (ABC1), member 1 | −2.73 | 0.00131361 |
| trophinin | −2.77 | 0.00298044 |
| cornichon homolog 3 (Drosophila) | −2.78 | 0.0261738 |
| formin binding protein 1-like | −2.78 | 0.00290401 |
| brain and acute leukemia, cytoplasmic | −2.78 | 0.0476919 |
| protein tyrosine phosphatase, receptor type, U | −2.80 | 0.0270428 |
| hypothetical protein MGC24103 | −2.82 | 0.0346673 |
| interferon induced with helicase C domain 1 | −2.83 | 0.0024839 |
| phospholipid transfer protein | −2.84 | 0.00999206 |
| immediate early response 3 | −2.87 | 0.0152127 |
| immediate early response 3 | −2.87 | 0.0152127 |
| ADAM metallopeptidase domain 12 (meltrin alpha) | −2.87 | 0.000870288 |
| synaptic vesicle glycoprotein 2A | −2.88 | 0.00704212 |
| chromosome 9 open reading frame 3 | −2.88 | 0.00410177 |
| thioredoxin interacting protein | −2.90 | 0.0135494 |
| early growth response 1 | −2.93 | 0.000425035 |
| small nucleolar RNA, C | −2.94 | 0.00666866 |
| small nucleolar RNA, C | −2.95 | 0.00765575 |
| immediate early response 3 | −2.99 | 0.0167309 |
| low density lipoprotein-related protein 1 (alpha-2-macroglo | −2.99 | 4.26E−05 |
| bicaudal C homolog 1 (Drosophila) | −2.99 | 0.0347162 |
| homeobox B2 | −3.03 | 0.00665994 |
| small nucleolar RNA, C | −3.10 | 0.0274043 |
| small nucleolar RNA, C | −3.10 | 0.0274043 |
| matrix metallopeptidase 2 (gelatinase A, 72 kDa gelatinase, | −3.13 | 5.59E−05 |
| KIAA1641 | −3.14 | 0.00659194 |
| collagen, type VI, alpha 3 | −3.14 | 2.09E−06 |
| homeobox A2 | −3.15 | 0.0435423 |
| SH3 and PX domains 2B | −3.15 | 0.0244357 |
| collagen, type VI, alpha 2 | −3.16 | 0.0149554 |
| chromosome 9 open reading frame 3 | −3.21 | 0.0233723 |
| small nucleolar RNA, C | −3.24 | 0.0104491 |
| small nucleolar RNA, C | −3.24 | 0.0104491 |
| — | −3.27 | 0.00488845 |
| UDP-N-acetyl-alpha-D-galactosamine:polypeptide N-acetylga | −3.35 | 0.00964109 |
| cholesterol 25-hydroxylase | −3.38 | 0.0445558 |
| KIAA1641 | −3.40 | 0.013175 |

TABLE 11-continued

Gene expression in Plurix cells (WO/2007/108003) compared to Celligen cells (teachings of the present invention)

| Gene | Celligen vs Plurix (fold change) | p-value (treat) |
|---|---|---|
| ring finger protein 144 | −3.40 | 0.0135334 |
| versican | −3.41 | 0.023885 |
| angiopoietin-like 2 | −3.42 | 0.0245161 |
| KIAA1641 | −3.44 | 0.0170531 |
| FBJ murine osteosarcoma viral oncogene homolog B | −3.54 | 0.00025573 |
| similar to RIKEN cDNA 1110018M03 | −3.59 | 0.00516476 |
| early growth response 2 (Krox-20 homolog, Drosophila) | −3.62 | 0.00821813 |
| dachsous 1 (*Drosophila*) | −3.63 | 0.00697244 |
| kinesin family member 26B | −3.64 | 0.00363199 |
| distal-less homeobox 5 | −3.66 | 0.000640157 |
| similar to Protein KIAA0220 | −3.69 | 0.0302619 |
| insulin-like growth factor 1 receptor | −3.71 | 3.42E−05 |
| protein tyrosine phosphatase, receptor type, N | −3.77 | 0.0294569 |
| KIAA1641 | −3.85 | 0.0191782 |
| sushi-repeat-containing protein, X-linked | −3.85 | 0.00370941 |
| microfibrillar-associated protein 2 | −3.91 | 0.0152901 |
| complement component 1, s subcomponent | −3.97 | 0.0395863 |
| CD24 molecule | −3.99 | 0.0340122 |
| homeobox B3 | −4.02 | 0.0354368 |
| trichorhinophalangeal syndrome I | −4.02 | 0.00557712 |
| Kallmann syndrome 1 sequence | −4.04 | 0.000548703 |
| leucine rich repeat containing 17 | −4.09 | 0.0263961 |
| plexin domain containing 2 | −4.32 | 0.031799 |
| PTK7 protein tyrosine kinase 7 | −4.42 | 0.000116114 |
| supervillin | −4.43 | 0.0412717 |
| zinc finger protein 521 | −4.58 | 0.00668815 |
| calbindin 2, 29 kDa (calretinin) | −4.77 | 0.0290743 |
| ras homolog gene family, member J | −4.79 | 0.00197982 |
| integrin, alpha 11 | −4.80 | 0.000390317 |
| odz, odd Oz | −5.05 | 0.00172671 |
| F-box protein 32 | −5.52 | 0.0212957 |
| raftlin family member 2 | −5.72 | 0.0260454 |
| clusterin | −5.74 | 0.0303973 |
| neurotrimin | −5.79 | 3.78E−06 |
| WNT1 inducible signaling pathway protein 1 | −5.86 | 0.000672342 |
| insulin-like growth factor binding protein 5 | −6.34 | 0.011614 |
| sulfatase 2 | −6.34 | 5.88E−05 |
| microfibrillar-associated protein 4 | −6.93 | 0.00155578 |
| junctional adhesion molecule 2 | −7.07 | 0.0306758 |
| fibronectin type III domain containing 1 | −7.29 | 0.0334696 |
| sarcoglycan, delta (35 kDa dystrophin-associated glycoprotei | −7.37 | 0.000881984 |
| hephaestin | −7.53 | 0.0123141 |
| serpin peptidase inhibitor, clade F (alpha-2 antiplasmi | −7.66 | 0.00362941 |
| cystatin SN | −7.96 | 0.0496433 |
| hemicentin 1 | −8.18 | 0.0461603 |
| tenascin C (hexabrachion) | −8.32 | 8.26E−05 |
| biglycan | −8.62 | 0.00161284 |
| transmembrane, prostate androgen induced RNA | −11.20 | 0.000100935 |
| carboxypeptidase E | −11.22 | 0.00738131 |

Expression of Cellular Markers on PLX-C Cells

The surface antigens expressed by PLX-C were examined using monoclonal antibodies. Results indicated that PLX-C cells were characterized by the positive markers: CD73, CD29 and CD105 and the negative markers: CD34, CD45, CD19, CD14 and HLA-DR (data not shown). The immune phenotype test specifications were set as: ≥90% for all positive markers and ≤3% for all negative markers.

Figures 7A, 7B, 7C:
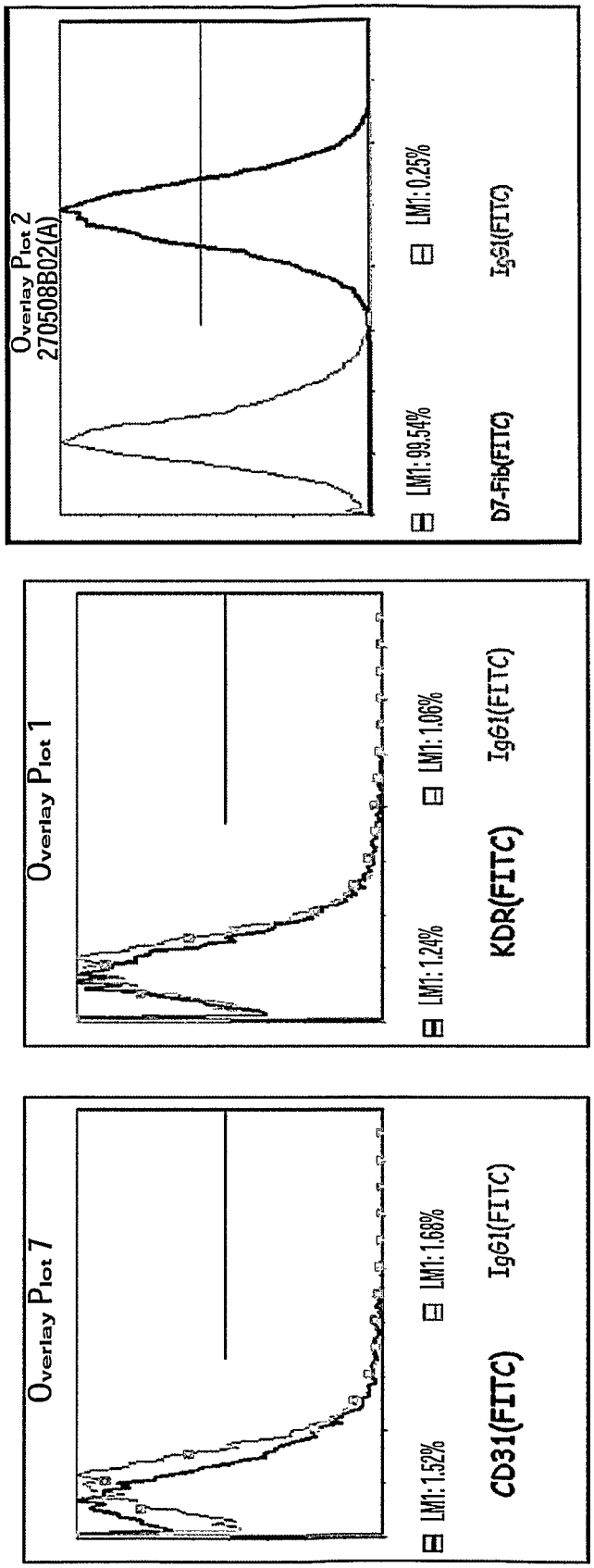
FIGS. 7A-C depict expression of fibroblast-typical markers but not expression of endothelial typical markers on PLX-C.

Furthermore, as shown in FIGS. 7A-B, PLX-C cultures did not express endothelial markers as shown by negative staining for the two endothelial markers CD31 and KDR. However, PLX-C expression of a fibroblast-typical marker was evident (expression of D7-fib, FIG. 7C).

Immunogenecity and Immunomodulatory Properties of PLX-C Cells

As PLX-C is comprised of adherent cells derived from placenta, it is expected to express HLA type I, which is expressed by all cells of the body and is known to induce an alloreactive immune response. HLA type II and other co-stimulatory molecules are typically expressed only on the surface of Antigen Presenting Cells (APCs).

Figure 8A:
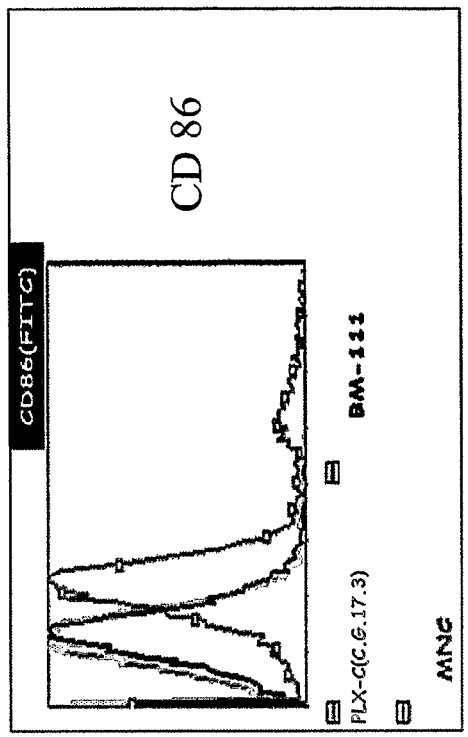
FIGS. 8A-D depict expression of stimulatory and co-stimulatory molecules on PLX-C cells.
Figure 8B:
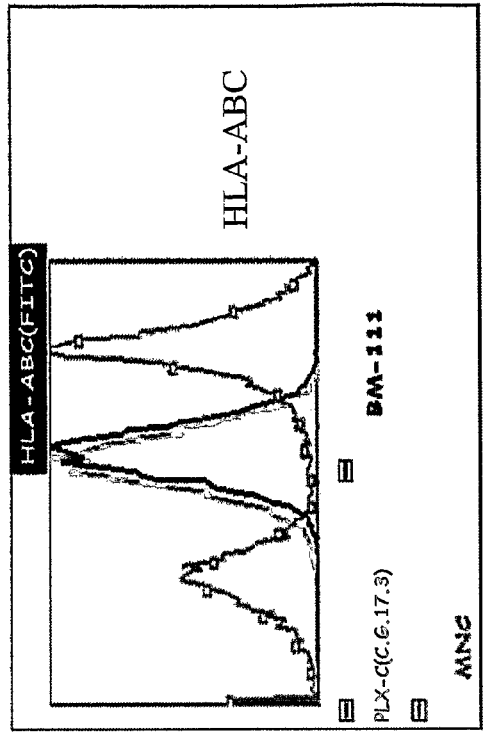
Figure 8C:
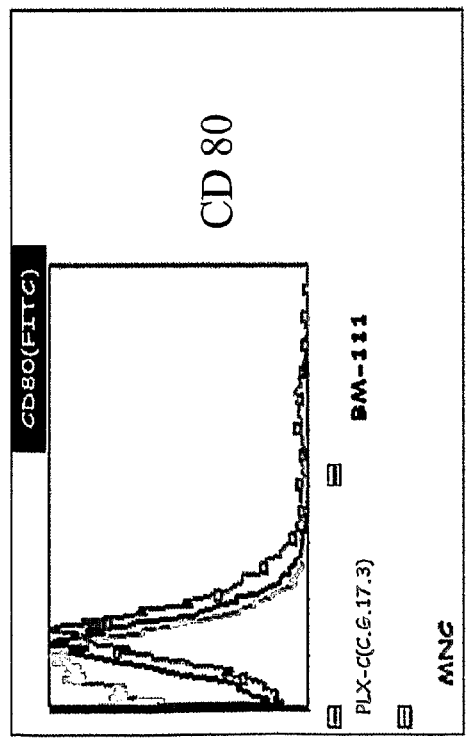
Figure 8D:
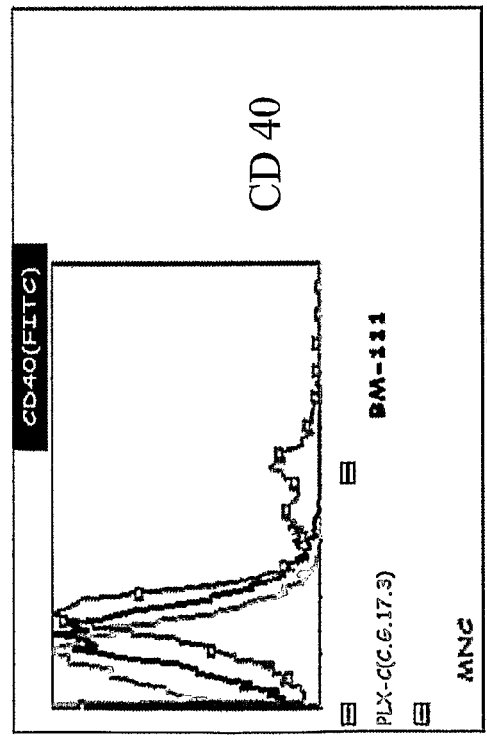

In order to examine the immunogenicity of the obtained PLX-C cells, the expression of co-stimulatory molecules on the surface of these cell membranes were performed. FACS analysis demonstrated the absence of CD80, CD86 and CD40 on the PLX-C cell membranes (FIGS. 8A-C). Moreover, PLX-C expressed low levels HLA class I as detected by staining for HLA A/B/C (FIG. 8D). The expression of stimulatory and co-stimulatory molecules was similar to bone marrow (BM) derived MSCs (as shown in FIGS. 8A-D).

Figures 9A, 9B:
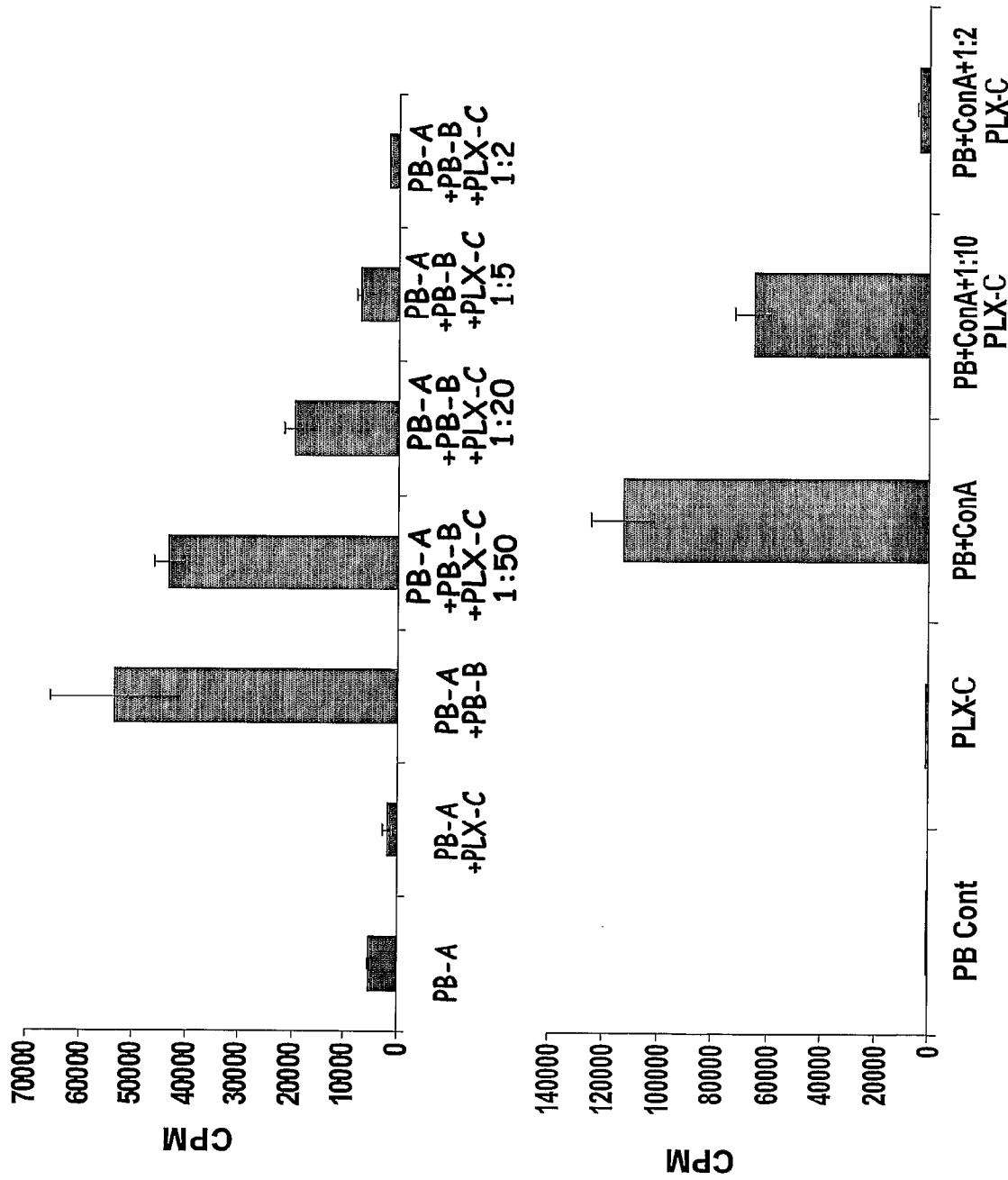
FIGS. 9A-B depict inhibition of lymphocyte proliferation by PLX-C.

To further investigate the immunogenecity as well as the immunomodulation properties of PLX-C cells, Mix Lymphocyte Reaction (MLR) tests were performed. As shown in FIGS. 9A-B, PLX-C cells both escape allorecognition and reduce T cell response, as measured by Thymidine incorporation. Furthermore, the reduction in lymphocytes proliferation (evaluated by CPM measurement) was higher as the number of PLX-C cells increased (in a dose dependent manner). PLX-C also reduced lymphocyte proliferation following mitogenic stimuli, such as Concavalin A (Con A, FIG. 9B) and Phytohemagglutinin (PHA), and non-specific stimulation by anti-CD3, anti-CD28 (data not shown).

In order to investigate the mechanism of action by which PLX-C immunomodulate lymphocyte proliferation, and to see if this action is mediated via cell to cell interaction or cytokines secretion, PB derived Mononuclear cells (MNCs) were stimulated by PHA using the transwell method (which prevents cell to cell contact but enables the diffusion of cytokines between the two compartments). Results showed that the inhibition of proliferation maintained even when cell to cell contact was inhibited (data not shown).

Cytokines Secretion

Figure 10A:
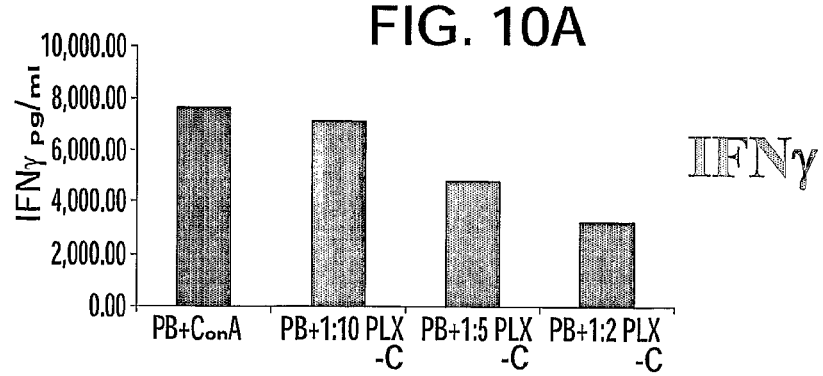
FIGS. 10A-C depict PLX-C regulation of pro-inflammatory and anti-inflammatory cytokine secretion following co-culture with peripheral blood cells.
Figure 10B:
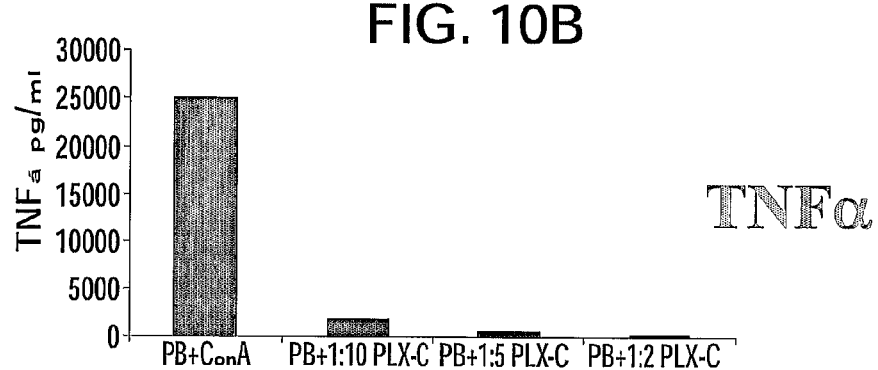
Figure 10C:
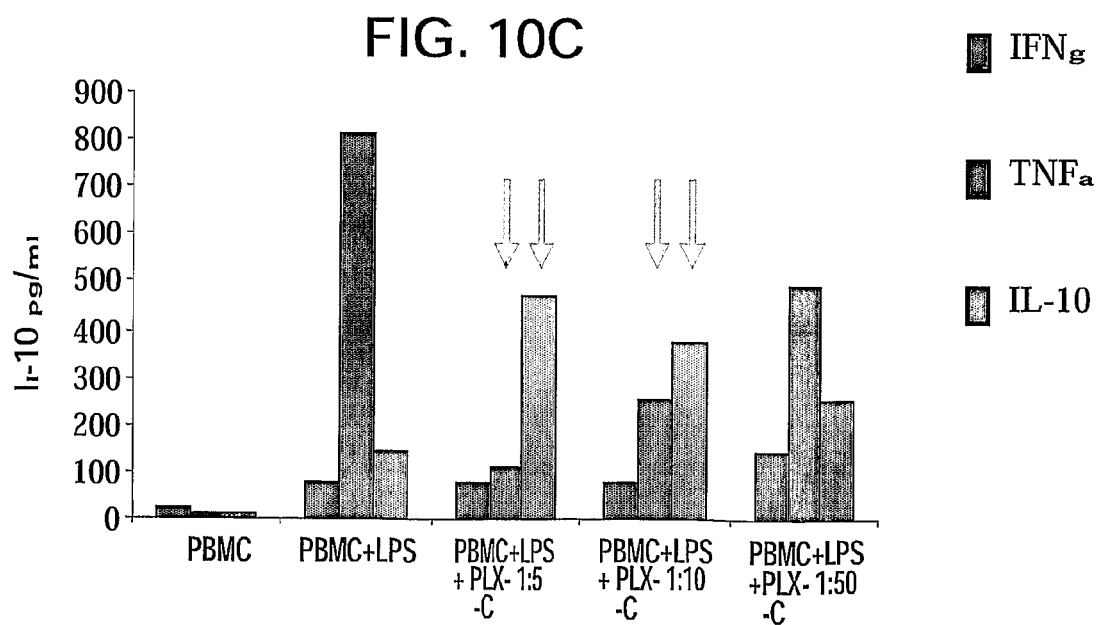

As depicted hereinabove, PLX-C reduce the proliferation rate of lymphocytes, probably through soluble factors. Further investigation of the cytokines secreted by lymphocytes in response to PLX-C was performed to elucidate the mechanism of action of PLX-C. As depicted in FIGS. 10A-B, culturing of mononuclear cells with PLX-C slightly reduced the secretion of the pro-inflammatory cytokine INFγ and dramatically reduced the secretion of TNFα (even in the presence of low amounts of PLX-C). In addition, following lipopolysaccharide (LPS) stimulation, PB derived MNCs secretion of IL-10 increased in the presence of PLX-C, while the secretion level of TNFα decreased, in a dose dependent manner (FIG. 10C).

It will be appreciated that the PLX-C cells of the present teachings were also capable of homing to ischemic tissues following intramuscular or intravenous injection into mice (data not shown).

Example 4

The Anti-Inflammatory Effect of PLX-C Cells in an in vivo Murine Model of Acute Colitis Materials and Experimental Procedures
TNBS Model of Intestinal Inflammation Colitis was induced in susceptible strains of rodents by intrarectal instillation of the haptenating substance TNBS (Trinitrobenzyl sulphonic acid) in ethanol. The use of TNBS in Ethanol was based on previous reports that ethanol is required to break the mucosal barrier whereas TNBS haptenizes colonic autologous or microbiota proteins rendering them immunogenic to the host immune system [Wirtz et al., Nature Protocols (2007) 2(3): 541-546].

Briefly, for colitis induction, mice were anesthetized for 90-120 minutes and received an intrarectal administration of TNBS (40 μl, 150 mg/kg) dissolved in a 1:1 mixture of 0.9% NaCl in 100% ethanol. Control mice received a 1:1 mixture of 0.9% NaCl in 100% ethanol or a saline solution using the same technique.

Mice were sacrificed 5 days post TNBS administration to assess the anti-inflammatory effect of the therapeutic cells (PLX-C cells) of the present invention. PLX-C administration was evaluated by intravenous (iv) administration or by intraperitoneal (ip) injection of the cells 1 day post colitis induction.

Animals

C57bl6 mice were used in these experiments. A total of 90 mice were used which were divided into 9 groups as follows:
1) 10 control mice (received no treatment)
2) 10 control mice+PLX-C-I batch 1 by ip ($2*10^6$ cells)
3) 10 control mice+PLX-C-I batch 1 by iv ($1*10^6$ cells)
4) 10 TNBS mice (colitis model mice)
5) 10 TNBS mice+5-aminosalicylic acid (5-ASA)
6) 10 TNBS mice+PLX-C-I batch 1 by iv ($1*10^6$ cells)
7) 10 TNBS mice+PLX-C-I batch 1 by ip ($2*10^6$ cells)
8) 10 TNBS mice+PLX-C-I batch 2 by iv ($1*10^6$ cells)
9) 10 TNBS mice+PLX-C-I batch 2 by ip ($2*10^6$ cells)

Production of the 2D Placenta Derived Adherent Cells
As depicted in detail in Example 2, hereinabove.
Production of the 3D Placenta Derived Adherent Cells (PLX-C Cells)
As depicted in detail in Example 3, hereinabove.
Vehicle
PlasmaLyte containing 5% Albumin was used as a vehicle control.
Tests and Evaluation Macroscopic and histological assessments of colitis were performed on colon specimens collected from the different mice experimental groups 5 days post TNBS administration. Macroscopic and histological assessments were conducted blindly by two investigators.

Macroscopical Analysis

The colon of each mouse was examined under a dissecting microscope (magnification, ×5) to evaluate the macroscopic lesions according to the Wallace criteria. The Wallace score rated the macroscopic lesions on a scale from 0 to 10 based on features reflecting inflammation, such as hyperemia, thickening of the bowel, and extent of ulceration.

TABLE 12

Wallace score

| Score | Criteria of macroscopic evaluation |
|---|---|
| 0 | No Inflammation |
| 1 | Hyperemia without ulcerations |
| 2 | Hyperemia with thickening of the mucosa without ulcerations |
| 3 | 1 ulceration without thickening of the colonic wall |
| 4 | 2 or more of ulcerative or inflammatory sites |
| 5 | 2 or more of ulcerative or inflammatory sites with an extent of more than 1 cm |
| 6 | 1 ulcerative or inflammatory site of more than 2 cm |
| 7 | 1 ulcerative or inflammatory site of more than 3 cm |
| 8 | 1 ulcerative or inflammatory site of more than 4 cm |
| 9 | 1 ulcerative or inflammatory site of more than 5 cm |
| 10 | 1 ulcerative or inflammatory site of more than 6 cm |

Histological Analysis

A colon specimen located precisely 2 cm above the anal canal was used for the histological evaluation according to the Ameho criteria. This grading (on a scale from 0 to 6) took into account the degree of inflammation infiltrate, the presence of erosion, ulceration, or necrosis, and the depth and surface extension of lesions.

TABLE 13

Ameho criteria

| Score | Criteria of histological evaluation |
|---|---|
| 0 | No alterations |
| 1 | Middle mucosal and/or sub-mucosal inflammatory infiltrates with oedema. Few mucosal erosions. Integrity of the muscularis mucosae. |
| 2 | Same criteria as score 1 but more than 50% of the section |

TABLE 13-continued

Ameho criteria

| Score | Criteria of histological evaluation |
|---|---|
| 3 | Large inflammatory infiltrate with ulceration area trough all the colonic |
| 4 | Same criteria as score 3 but more than 50% of the section |
| 5 | Wide ulcerations with cellular necrosis |
| 6 | Wide ulcerations with cellular necrosis but more than 50% of the section |

Molecular Analysis of Colitis

Quantification of mRNA Expression of IL-1 Beta

Total RNA was isolated from whole mice colonic tissues using Rneasy kit (Macherey Nagel, Hoerdt, France) according to the manufacturer's instructions. RNA quantification was performed using spectrophotometry. After treatment at 37° C. for 30 minutes with 20-50 units of RNase-free DNase I (Roche Diagnostics Corporation, Indianapolis, Ind., USA), oligo-dT primers (Roche Diagnostics Corporation, Indianapolis, USA) were used to synthesize single-stranded cDNA. mRNAs were quantified using SYBR green Master Mix (Applera, Courtaboeuf, France) with mouse specific oligonucleotides for IL-1β: S: 5'-gATCCACACTCTCCAgCT-gCA-3' (SEQ ID NO: 1) and AS: 5'-CAACCAACAAgT-gATATTCTCCATg-3' (SEQ ID NO: 2) in a GeneAmp Abiprism 7000 (Applera, Courtaboeuf, France). Each assay was calibrated and no-template controls were included. Each sample was run in triplicate. SYBR green dye intensity was analyzed using the Abiprism 7000 SDS software (Applera, Courtaboeuf, France). All results were normalized to the unaffected housekeeping gene β-actin (oligonucleotides for β-actin: S: 5'-gggTCAgAAggATTCCTATg-3' SEQ ID NO: 3; AS: 5' ggTCTCAAACATgATCTggg-3' SEQ ID NO: 4).

Results

As described in detail hereinabove, mice were sacrificed on day 5 following induction of colitis by intra-rectal injection of TNBS on day 0 and adherent cell administration on day 1. Mice were administered with either 2D adherent cells (hereinafter batch 1) or PLX-C adherent cells (hereinafter batch 2) obtained from placenta 1 or placenta 2, respectively. After the mice were sacrificed, macroscopic and microscopic evaluations of the colon were performed.

As demonstrated in FIG. 11, mice treated by an iv injection of 2D and PLX-C cells (batch 1 or 2, respectively) exhibited a major improvement in the inflammatory condition of the colon tissue as represented by the Wallace score. This anti-inflammatory effect was as efficient as the 5-ASA gold standard treatment). It will be appreciated that ip administration of 2D adherent cells (batch 1) also resulted in a satisfactory improvement in the Wallace score of the colitis model mice.

Microscopic evaluation of the colon revealed that administration of PLX-C cells (batch 2) by either ip or iv routes significantly reduced colonic inflammation at the histological level compared to TNBS mice (as represented by the Ameho score, FIG. 12). A considerable improvement was also observed for TNBS mice who received 2D cells (batch 1) by iv administration (FIG. 12). The improvement in these treatment groups was significantly better compared to the 5-ASA treated TNBS group.

Figure 13:
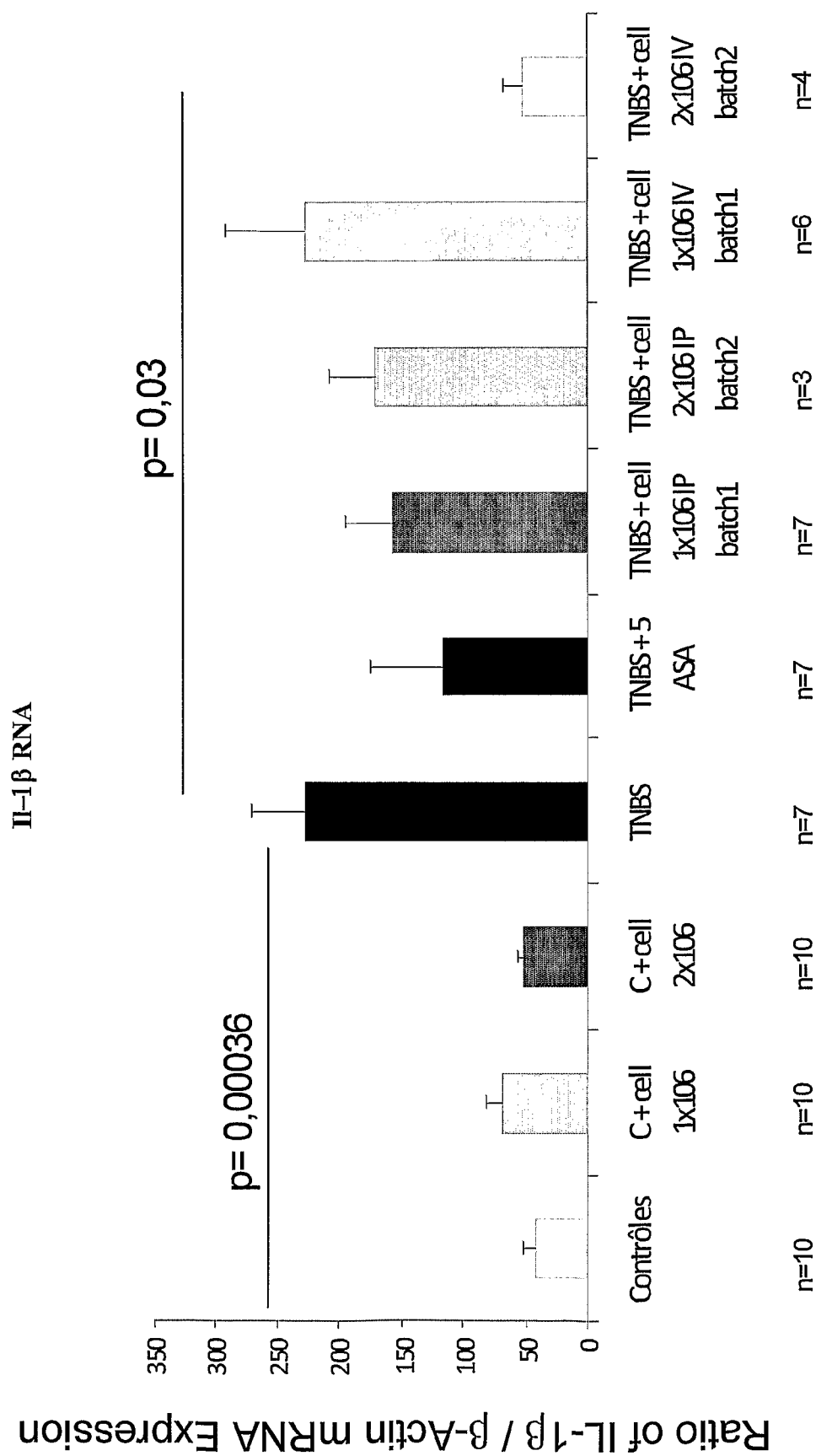
FIG. 13 is a graph depicting IL-1β mRNA expression level in colonic tissues of colitic mice. Mice were rendered colitic by intrarectal administration of TNBS and were administered 2D or 3D (PLX-C) adherent cells via intraperitoneal or intravenous routes. Total RNA was isolated from colonic tissues of the different experimental groups and IL-1β expression levels were evaluated by RT-PCR.

Furthermore, total RNA was isolated from colonic tissues and IL-1β expression levels were evaluated by RT-PCR (as described in detail hereinabove). As evident from the results (FIG. 13), administration of PLX-C cells (batch 2) by iv significantly reduced the expression level of IL-1β in colonic tissues. It will be appreciated that although IL-1β RNA expression levels were not significantly reduced by ip administration (2D or 3D adherent cells, batches 1 and 2, respectively) and iv administration (2D adherent cells, batch 1), administration of both PLX-C and 2D cells still resulted in significant reduction in inflammation based on macroscopic and microscopic evaluations in colitic mice.

Taken together these results demonstrated that administration of the placental adherent cells of the present invention (2D and 3D PLX-C cells) lead to a significant improvement in colon inflammation in a mouse model of acute colitis.

Example 5

The Anti-Inflammatory Effect of PLX-C Cells in an in-vivo Rat Model of Acute Colitis Materials and Experimental Procedures TNBS Model of Intestinal Inflammation Rats were rendered colitic by intracolonic administration of 22 mg of TNBS dissolved in 1:1 mixture of EtOH and water. 24 hours post colitis induction rats were administered according to the study treatment.

The rats used in this study were divided into three study groups (as depicted in detail below). Eleven days following colitis induction, all rats were sacrificed and colonic damage was evaluated both microscopically and macroscopically.

Administration of TNBS was designated as day 0, PLX-C cells were administrated on day 1 and rats were sacrificed on day 11.

Animals

12 Female Lewis rats (100-120 g) were used in these experiments. A total of 12 rats were used which were divided into 4 groups as follows:

1) 4 rats were administered ip with $5 \times 10^6$ PLX-C-I cells
2) 4 rats were administered iv with $5 \times 10^6$ PLX-C-I cells
3) 2 rats received PlasmaLyte by ip (control group)
4) 2 rats received PlasmaLyte by iv (control group)

Production of the Placenta Derived Adherent Cells (PLX-C Cells)

Cells were produced as depicted in detail in Example 3, hereinabove.

Macroscopic Assessment of Colonic Damage

Macroscopic assessment of colonic damage was evaluated according to the following criteria:

0—No damage
1—Hyperemia but no ulcers
2—Fibrosis but no ulcers
3—Ulceration/necrosis less than 1 cm
4—Ulceration/necrosis less than 2 cm
5—Ulceration/necrosis more than 2 cm Microscopic (Histological) Assessment of Colonic Damage Microscopic assessment of colonic damage was evaluated according to all of the following criteria (A+B+C+D):

A. Extent of ulceration:
  0—No ulcer
  1-2—Small ulcers (less than 3 mm)
  3-5—Large ulcers (more than 3 mm)
B. Submucosal infiltration:
  0—None
  1—Mild
  2-3—Moderate
  4-5—Severe
C. Crypt abscesses:
  0—None
  1-2—Rare
  3-5—Diffuse D. Wall thickness (μm)
0—less than 470
1—less than 600
2—less than 700
3—less than 800
4—less than 900
5—more than 900
Results As evident from FIG. 14, administration of the 3D adherent cells of the present invention (PLX-C cells) lead to a significant improvement in the microscopic scores (histological assessment) of acute colitis in rats.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating inflammation of intestinal tissue in conditions of ulcerative colitis or Crohn's disease in a subject in need thereof, the method comprising administering to said subject a therapeutically effective amount of adherent, non-autologous cells derived from placenta, thereby treating the inflammation of intestinal tissue in conditions of ulcerative colitis or Crohn's disease, wherein said adherent, non-autologous cells do not exhibit osteogenic differentiation as assessed by Alizarin Red staining, when subjected to conditions that induce bone marrow cells to undergo osteogenic differentiation.

2. The method of claim 1, wherein said adherent cells express one or more of CD73, CD90, CD29, or CD105.

3. The method of claim 1, wherein said adherent cells do not express CD3, CD4, CD45, CD80, HLA-DR, CD11b, CD14, CD19, or CD79.

4. The method of claim 1, wherein said adherent cells suppress an immune reaction by suppressing T cell activity.

5. The method of claim 1, wherein said adherent cells are obtained from a three-dimensional (3D) culture.

6. The method wherein said three-dimensional (3D) culture comprises a 3D bioreactor.

7. The method wherein culturing of said adherent cells in said 3D culture comprises perfusion of the adherent cells with a continuous flow of a culture medium.

8. The method wherein culturing of said adherent cells occurs for at least 3 days.

9. The method of claim 1, wherein said adherent cells comprise cells cultured from the placenta under 2 dimensional (2D) culturing conditions.

10. The method wherein at least 12% of said adherent cells are at a S and/or G2/M proliferative phase.

11. The method of claim 1, wherein said adherent cells are less committed to an adipogenic lineage as compared to adherent cells from bone marrow grown and allowed to differentiate under the same conditions.

12. The method of claim 1, further comprising co-administering an immunosuppressant agent or an anti-inflammatory agent.

13. The method of claim 1, wherein the adherent, non-autologous cells are administered via one of an intravenous, intramuscular, or intraperitoneal injection.

14. The method of claim 1, wherein said adherent, non-autologous cells do not express CD34.

* * * * *